(12) United States Patent
Liu et al.

(10) Patent No.: US 7,951,552 B2
(45) Date of Patent: May 31, 2011

(54) METHOD OF PREPARING NON-HUMAN TISSUES FOR XENOTRANSPLANTATION USING α-GALACTOSIDASE

(75) Inventors: Qiyong Peter Liu, Newton, MA (US); Henrik Clausen, Holte (DK)

(73) Assignee: Velico Medical, Inc., Beverly, MA (US)

( * ) Notice: Subject to any disclaimer, the term of this patent is extended or adjusted under 35 U.S.C. 154(b) by 0 days.

(21) Appl. No.: 12/091,818

(22) PCT Filed: Oct. 31, 2006

(86) PCT No.: PCT/US2006/042350
§ 371 (c)(1),
(2), (4) Date: Jan. 12, 2009

(87) PCT Pub. No.: WO2007/053565
PCT Pub. Date: May 10, 2007

(65) Prior Publication Data
US 2009/0220474 A1  Sep. 3, 2009

Related U.S. Application Data

(60) Provisional application No. 60/731,845, filed on Oct. 31, 2005, provisional application No. 60/836,000, filed on Aug. 7, 2006.

(51) Int. Cl.
*A61K 35/36* (2006.01)
*C12Q 1/34* (2006.01)
*C12N 9/40* (2006.01)
*C12P 21/00* (2006.01)
*C07K 14/00* (2006.01)

(52) U.S. Cl. ......... 435/18; 435/208; 435/69.1; 424/572; 530/350

(58) Field of Classification Search .................. 435/208, 435/18, 69.1, 1.1; 530/350; 536/23.2
See application file for complete search history.

(56) References Cited

U.S. PATENT DOCUMENTS

| | | | |
|---|---|---|---|
| 4,427,777 A | 1/1984 | Goldstein | |
| 5,606,042 A | 2/1997 | Smith et al. | |
| 5,633,130 A | 5/1997 | Smith et al. | |
| 5,731,426 A | 3/1998 | Smith et al. | |
| 5,984,858 A | 11/1999 | Stone | |
| 6,093,204 A | 7/2000 | Stone | |
| 6,184,017 B1 | 2/2001 | Smith et al. | |
| 6,267,786 B1 | 7/2001 | Stone | |
| 6,383,732 B1 | 5/2002 | Stone | |
| 6,402,783 B1 | 6/2002 | Stone | |
| 6,455,309 B2 | 9/2002 | Stone | |
| 6,758,865 B1 | 7/2004 | Stone et al. | |
| 6,933,326 B1 | 8/2005 | Griffey et al. | |
| 6,972,041 B1 | 12/2005 | Stone | |
| 7,064,187 B2 | 6/2006 | Stone | |
| 2003/0157474 A1 | 8/2003 | Clausen et al. | |
| 2005/0028228 A1 | 2/2005 | McQuillan et al. | |
| 2005/0159822 A1 | 7/2005 | Griffey et al. | |

OTHER PUBLICATIONS

Berg et al., Applied and Environmental Microbiology 40(1):40-47, 1980.*
LaVecchio et al., Transplantation 60(8):841-847, 1995.*
Supplementary Partial European Search Report —(EP 06827104) Date of Completion Dec. 14, 2009.
Kuwahara et al., "Conserved Hypothetical Protein [Bacteroides Fragilis YCH46]", Database Genbank [Online], Apr. 20, 2004, retrieved from NCBI, database accession No. BAD51191.
Kenji Kondoh, et al., "Cloning and Expression of the Gene Encoding Streptomyces Coelicolor A3(2) [alpha]-Galactosidase belonging to Family 36", Biotechnology Letters, Kluwer Academic Publishers, DO, 2005, vol. 27, pp. 641-647.
Goldstein J, et al., "Group B Erythrocytes Enzymatically Conserved to Group O Survive Normally in A B and O Individuals", Science, (Washington D C), 1982, pp. 168-170.
Olsson M L, et al., "Universal Red Blood Cells-Enzymatic Conversion of Blood Group A and B Antigens//Globules Rouges Universels-Conversion Enzymatique Des Antigens De Groups Sanguins A et B", Transfusion Clinique et Biologique, Arnette-Blackwell, Paris, FR, 2004, vol. 11, pp. 33-39.
International Search Report (PCT/US06/42350); Date of Mailing: Apr. 30, 2008; 1 page.
Partial European Search Report—(EP 10165154) Date of completion of the search Sep. 21, 2010.
Partial European Search Report—(EP 10165152) Date of completion of the search Sep. 21, 2010.
Database Uniport [Online], Liu et al., Jun. 1, 2003, nucleotide sequence, retrieved from EBI, Database accession No. Q826C5.
Ezzelarab et al., "Reducing Gal expression on the pig organ—a retrospective review", Xenotransplantation, vol. 12, No. 4, Jul. 2005, pp. 278-285.
Luo et al., "Pig xenogeneic antigen modification with green coffee bean alpha-galactosidase", Xenotransplantation, vol. 6, No. 4, Nov. 1999, pp. 238-248.
Stone et al., "Porcine cartilage transplants in the cynomolgus monkey III. Transplantation of alpha-galactosidase-treated porcine cartilage", Transplantation, vol. 65, No. 12, Jun. 1998, pp. 1577-1583.

* cited by examiner

*Primary Examiner* — Delia M Ramirez
(74) *Attorney, Agent, or Firm* — Foley & Lardner LLP; Michel Morency; James F. Ewing

(57) ABSTRACT

This invention relates to novel α-galactosidases for the enzymatic removal of the immunodominant monosaccharides on blood products and tissues. Specifically this invention provides a novel family of α3 glycosidases, used for the enzymatic removal of type B antigens from blood group B and AB reactive blood products, and the Galili antigen from non-human animal tissues, thereby converting these to non-immunogenic cells and tissues suitable for transplantation.

2 Claims, 21 Drawing Sheets

FIG. 10.

```
  1  MAHGCSGGAM SRFVFLGVAL ALLGGATSPA AAAPRVTPvV VDVcDYGADP TGRtDStpAV AAALrHAKSV DRPVRIVFSK
 81  GTYQLYPERA ETRELYMSNT VGADQRYRDK KIGLLVEDMH DVTVDGGGAK LVHHGLQTAF ASIRSTDVTF QNFSFDYAAP
161  EVIDATVATT GVTDGHAYRV LKIPAGSPYR VNGTHITWLG ETSPATGQPY WSGVDGLQYT QIHDPEAQRT WRGDNPLFND
241  VAAVTDLGGR RIRIDYTTAA RPADAGLVYQ MRLIERTEPG AFIWESKNVT MRSMNAYYLQ SFGVVGQFSE NLSIDKVNFA
321  PDPRSGRSTA SFADFVQMSG VKGKVSITRS LFDGPHDDPI NIHGTYLEVV GKPGPSTLTL AYKHPQTAGF PQFAPGDEVE
401  FATKRTMTPL ADAHAQVTAV DGPSGMDHTK RPVPAGVETG GTVVENITAT PSVVISGNVF RNVPTRGILV
481  TTRKPVLITG NRFDGMSMAS IYVSADAYQW IRGNSFTRPS GPVIFVEPTN QVIDPATPVH HNISVEHNSF
561  DIGDVTVVNA KSVGGFAFTG NTVRRLDGAD HPPYTSPLFV FHGSSGIRIA RNHYDKGLNT SVVTD
```

FIG.12.

```
                      10         20         30         40         50         60         70         80         90        100        110        120
                      |          |          |          |          |          |          |          |          |          |          |          |
SA         MAHGCSGGAMSRFVFLGVALALLGGATSPAAAAPRVTPVVVDVDDYGADPTGRTDSTPAVAAALR---HAKSVDRPVRIVFSKGTYQLYPERAETRELYMSN-TVGADQRYRDKKIGLLIV
BTalpha    ----------MMSVWFIQLAIFAQS---------RIIEVTPEQ---G-----KDIENIALALKK---AADCKGRPVTVKFSPGIYQLDRAKSSQVLYYISNTTSELDDPDPTKHIGLYI
BFalpha1   ----------MKKYLHILPACFLFYAAAH-----AQQKDITVVTDFGAVPYSYENCVTQIQAAID----ECKRTGAKVLSLPEGRYDIWPEGATRKEYYISNTSTEQECPSKVKTVGLML
BFalpha2   ----------MKKYLHILPACFLFYAAAH-----AQQKDITVVTDFGAVPYSYENCVTQIQAAID----ECKRTGAKVLSLPEGRYDIWPEGAIRKEYYISNTSTEQECPSKVKTVGLML
BFbeta2    ----------MKTTILLFALSLLLSLSVSD-----VCAQERVYDISQFGLKANSKKNASPVVRKAIAKIKAECRDGEKVILRFPAGRYNFHEAGSTVREYYISNHD-----QDNPKKVGIAL
BFbeta1    ----------MKTILLFALSLLLSLSVSD-----VCAQERVYDISQFGLKANSKKNASPVVRKAIAKIKAECRDGEKVILRFPAGRYNFHEAGSTVREYYISNHD-----QDNPKKVGLAL
BTbeta     ----------MRTFLSLKTCLLSALLLCVN----SIAASKIILSVSDFGLKPDSRINAVPFIQKAID----ACKQHPGSTLVFPKGRYDFWAQHALEKDYYETNTY-----DVNPKILAVLL
                      *  :                :                                                                  *  :  *    :    * :::
Prim.cons. MAHGCSGGAMKT3L3I2LAL2L2L2A222AAAAV3AQE3VVDVSDFG2KP2S3KNAVP22QAAIDKIKAECK2G33V3L3FP3GRYDFWP2GAT22EYYISNT3TEQ2CPDNPKKVGL3L 130        140        150        160        170        180        190        200        210        220        230        240
                      |          |          |          |          |          |          |          |          |          |          |          |
SA         EDMHDVTVDGGGAKLVHHGLQTAFASIRSTDVTFQNFSFDYAAPEVIDATVATTGVTDGHAYRVLKIPAGSPYRVNGT-HITWLGETSPATGQPYWSGVDGLQYTQIHDPEAQRITWRGDN
BTalpha    NTLKNITIDGCGSTLLMNGEMTSFVLDKCEGIVLKNFNLDYKHPTQTEVLEE----GNDYLIVQVHPTSQYRIVDA-QLEWYGDG------WSFKN--GIAQSYDRISEMTWRSWS
BFalpha1   HEIDDLTIEGNGATLMYHGKMTTIALEHCNGVRINNLHIDFERPAGSEIQYRKV---TGGE-TEVTLHRDTRYEIVNG-KIRLYGEGWRSN-KNHCIEYDPDTESFTYSQGW-NTLSASD
BFalpha2   HEIDDLTIEGNGATLMYHGKMTTIALEHCNGVRINNLHIDFERPAGSEIQYRKV---TGGE-TEVTLHRDTRYEIVNG-KIRLYGEGWRSN-RNHCIEYDPDTESFTYSQGW-NTLSASD
BFbeta2    EDMKNLTIDGQGSEFVFYGRMIPVSLLRSENCVLKNFSIDFEQPHIAQVQVVEN---DPEKGITFEPAPWVDYRISKDSVFEGLGEGWVMR-YSWGIAFDGKIKHVVYNTSD-IGCPTKG
BFbeta1    EDMKNLTIDGQGSEFVFYGRMIPVSLLRSENCVLKNFSIDFEQPHIAQVQVVEN---DPEKGITFEPAPWVDYRISKDSVFEGLGEGWVMR-YSWGIAFDGKIKHVVYNTSD-IGCPTKG
BTbeta     EQINDLTIDGNGSEFIMGRMQPFTLDHCRNITLKNFSVDWEIPLTAQGIVTQS---TSEY-LELEIDSHQYPYIIENKRLTFVGEGWKSS-LWAIMQFDPDTHLVLPNTGDNLGWRSYD
               :::*:*:.:  *.  :   .   :.       ::*:. .*::   *     :           .    :     *:                   *:
Prim.cons. ED2KDLTIDGNGS2LV3HGRMTPFAL32CE2VVLKNFSIDFE2P22A2VQV2E2GVT2GE223EVE33HP232YRIV22S2IE32GEGW2S2GY223I2FD2DT22V2YNTGD32TWR32D 250        260        270        280        290        300        310        320        330        340        350        360
                      |          |          |          |          |          |          |          |          |          |          |          |
SA         PLFNDVAAVTDLGGRRIRIDYTTAARPADAGLVYQMRLLERTEPGAFIWESKNVTMRSMNAYYLQSFGVVGQFSENISIDKVNFAPD-PRSGRSTASFADFVQMSGVKGKVSITRSLFDG
BTalpha    PMEN-LLRTVELRPNVLYLQYKEKPQ-VGLHTTIFQMRDSFRDEVSGFVNRSKGILLENINFYYLGNFGVVCYQYSENETVDRCNFAPR-PGSGRTNAGFADFIQVSGCRGMIDIKNSRFIG
BFalpha1   AREIAPGIVRFNTP----AEFMPKAG-----NTLTVRDIIRDQVGFFILESKNITLSRLQMHYMHGLGIVSQYTENITMDRVKCAPR-PDSGRLLAASADMMHFSGCKGKVIIDSCYFAG
BFalpha2   AREIAPGIVRFNTP----AEFMPKAG-----NTLTVRDIIRDQVGLFILESKNITLSRLQMHYMHGLGIVSQYTENITMDRVKCAPR-PDSGRLLAASADMMHFSGCKGKVIIDSCYFAG
BFbeta2    AFEVAP--RRICSPKWKDARLVPG-------TVVAMRGWGRPTPGIFMSHDVNTSLLDVKVHYAEGMGLLAQLCEDITLDGFGVCLKGDNDPRYFTTQADATHFSGCKGKIVSKNGLYEG
BFbeta1    AFEVAP--RRICSPKWKDARLVPG-------TVVAMRGWGRPTPGIFMSHDVNTSLLDVKVHYAEGMGLLAQLCEDITLDGFGVCLKGNNDPRYFTTQADATHFSGCKGKIVSKNGLYEG
BTbeta     ATEINPGLIRLSDPKKEADKFFPAPG-----TVLVLRHSTRDHAGIFIYHSMDTKLENVKLPHTCGLGIISQYSKNISFNDVHIIPN-TSKKRVLSGHDDGFHFMGCSGLLKIENCSWAG
                   .  .    :                 :*: :    : .    ..       :  : :             .            .           : .      .
Prim.cons. A2EIAPGIVR232PKWKDA2F2PKAGP2222TVL3MRDI2RD32GIFI22SKN2TL33VK2HY32GLGIVSQYSENIT2DRV33APRGP2SGR2LA33AD32HFSGCKGK22IKNCLFAG
```

FIG.12. continued

```
                 370        380        390        400        410        420        430        440        450        460        470       480
SA          PHDDPINIHGTYLEVVGKPGPSTLTLAYKHPQTAGFPQFAPGDEVEFATKRTMTPLADAHAQVTAVDGPSGMDHTKPLTTMTVTFDRPVP-AGVETGGTVVENITATPSVVLSGNVFRNV
BTalpha     AHDDPINIHGTHLRVIEFLSDNRLKLRFMHDQTFGFEAFFKGDDIELVDSRSLLVVGKCKVKEAKLVTPREMELTLSSPLSSEVMQQ------KDLVIENVTWTPEVRITNNYFARV
BFalpha1    AQDDPVNVHGTNLRALEKIDAQTLKLRFMHGQSYGFNAYFKGDTVAFIRAATMERFASA----TVR------DVRRLSDRIVEVRFDRDIP-TSLELNHDCVENMTCTPEVEIRNSYFTRT
BFalpha2    AQDDPVNVHGTNLRALEKIDAQTLKLRFMHGQSYGFNAYFKGDTVAFVRAATMERFASA----TVR------DVRRLSDRIVEVRFDRDIP-TSLELNHDCVENMTCTPEVEIRNCYFTRT
BFbeta2     MMDDAINVHGTYLKVIKRVDDHTLIGRYMHDQSWGFEWGRPGDDVQFVRSETMELIGKQNQITAIRP--YDKGEIRGAREFSITFKEAIDPAINEKSGFGIENLTWTPEVLFAGNTIRNN
BFbeta1     MMDDAINVHGTYLKVIKRVDDHTLIGRYMHDQSWGFEWGRPGDDVQFVRSETMELIGKQNQITAIRP--YDKGEIQGAREFSITFKEAIDPAINEKSGFGIENLTWTPEVLFAGNTIRNN
BTbeta      LMDDPINIHGTCSRIMEVLSPTRIKCKFMQDMSEGMEWGRPDETIGFIEHKTMRIVATG----KMN------KFEALNKAEFIIELSVPLP--AGVEAGVIENLTCTPDAEIRNCHFGSC
              **:.*:***   . .   :   **                          :            :  **  .                                  :::.       .:
Prim.cons.  AMDDPINVHGTYLRVIEK3DD2TLKLRFMHDQS2GFE2G2PGD2V3FVRS3TME23AKANQIT22RP2PYDK2E32S2REFS2TFDR3IPPA22E22G2VIENLT2TPEVEIRNNYFR23

490        500        510        520        530        540        550        560        570        580        590       600
SA          PTRGLLVTTRKPVLITGNRFDGMSMASIYVSADAYQWYESGPVADLTIRGNSFTR--------PSGPVIFVEPTNQVIDPATPVHHN-----ISVEHNSFDIGDVTVVNAKSVGGFAFTG
BTalpha     PTRGILITTRRKSLIEGNTFYGMQMSGIFVADDGLSWYESGPVHDLTIRQNTFLN--------CGEPIISIDPENREYKGAVHKNIT-----IEENYFYMRKNSSCAIRAKAVDGLMIRH
BFalpha1    STRGTLVTTPRKVVIENNTYKTGMSAILIEADAEGWYESGPVKDVLIKGNTFID--CAYNGGPGHAVIAIHPSNKIIDAERPVHQN-----IRIEDNTFRTFDYPVLYAKSTAGLLFRN
BFalpha2    STRGTLVTTPRKVVIENNTYKTGMSAILIEADAEGWYESGPVKDVLIKGNTFID--CAYNGGPGHAVIAIHPSNKIIDAERPVHQN-----IRIEDNTFRTFDYPVLYAKSTAGLLFRN
BFbeta2     RARGTLFSTPKKTVVEDNLFDHTSGTAILLCGDCNGWFETGACRDVTIRRNRFIN-ALTNMFQFTNAVISIYPEIPNLKDQQKYFHGGKDGGIVIEDNEFDTFDAPILYAKSVDGLIFRN
BFbeta1     RARGTLFSTPKKTVVEDNLFDHTSGTAILLCGDCNGWFETGACRDVTIRRNRFIN-ALTNMFQFTNAVISIYPEIPNLKDQQKYFHGGKDGGIVIEDNEFDTFDAPILYAKSVDGLIFRN
BTbeta      RARGLLVSTPGKVIIENNVFE-SSGSAILIAGDANAWYESGAVKDVLIRNNDFRXPCNSSIYQFCEAVISIDPEITPEQKYPYHRN-----IRIMDNTFHLFDYPILFARSVNGLTFSS
              :**  *:*     ::  ::  * ** : :.. :  **::    .  :  *:*    *                :                     * :    .   :   ..*   .
Prim.cons.  RTRGTLVTTP2KVVIENNTP23TSMSALLI32DANGWYESGPVKDVTIRGNTFINPA22222Q2G3AVISI3PENP2I2232P2HHNGKDGIRIEDNTF2TFDYP2LYAKSVDGL2FRN 610        620        630        640        650        660
SA          NTVRRLDGADHPPYTSPLFVFHGSSGIRIARNHYDKGLNTSVVTD---------
BTalpha     NLIYSLDTEKNK--ESDFIQMNCNEVTIKENRVQLHHLFK--------------
BFalpha1    NTIVRTETFPAASGNPYVFYLNGCKKAVIEGTVFKGETPRQSIKTENMKRKDLKTIK-------
BFalpha2    NTIVRTETFPAVSGNPYVFYLNGCKKAVIEGTVFEGETPRQSIKTENMKRKDLKTYIK------
BFbeta2     NVIKTNTEFKPFHWNKDRFLLERVTNVKISE-----------------------
BFbeta1     NVIKTNTEFKPFHWNKDRFLLERVTNVKISE-----------------------
BTbeta      NTLIRDTTYQFYHYRKEGITLEACKSVVISNNKLEGDVLGRIVTIEKMKPSDVLISKNPFFKLKK
              *                                      *
Prim.cons.  NTI2R3TTFKPFH3NKD2F2LEGCK2VVISENVFEGET2RQS22TENMKRKDLKTTIKPFFKLKK
```

```
  1  MGTATAQPAL RPQTSTVIGG LHGAAVLDNT GRTVIDVTDF GADPSGKADS
 51  AAAVSAAMAH AKTVGGPTTL HFPTGTYHIW PERTPKRELY VSNTVGSDQA
101  FRTKNIGILV EDMRDVVVDG GGSRIVNHGF QTVFAAIRSS DVRFTNFSQT
151  WVAPKTVDIT VADAGVVSGQ AYRIIDIPET YDYAVEGTSV RWNGERGPAT
201  GQPYWTGTNS FDYSQVHDPA TNRTWRTSNP VFPERHEDHR PRRRQVRITY
251  GDSTAPGDRG YVYQMREVTR DTPGALFWES SRVTVDHLRL GYLHG
301  DIG         DRGSG RVTSGFADHI QMSGVKGTVR ITNSVEDNPQ
351  DDPINIHGTY LQATAAERET LQLRYMHNET SGFPQFYPGD TIELVDKRTM
401  LAAPGATAKV VSVTGPTGSG VPAGTDPDTY LRTMTVVLDR TLPAAVLAAP
451  GDYVAENTTY TPTVEITGNT FQAVPTRGIL VTTRRPVRIE NNRFDGMSMA
501  SIYISSDARS WYESGPVRNV TIRGNVFDRP ASPVIFFDPT NQDFVAGQ
551        EDND FNLTGGTILS GRGVGGLTFR DNRVERYPHL RLTGPSRALR
601  VGDTTTVTTD APPPSHTSPL FTFDGADDIT LANNTYGNGF NKRVNTANMD
651  VSEITVTADG LALNADSISS APVAVSYSSS RPKVATVDSE GVVKALSGGT
701  TSITARATIG GVRVTSNPVK VVVATER
```

Fig. 20.
A. Substrate specificity of BFα2 (FragA) α-galactosidase.
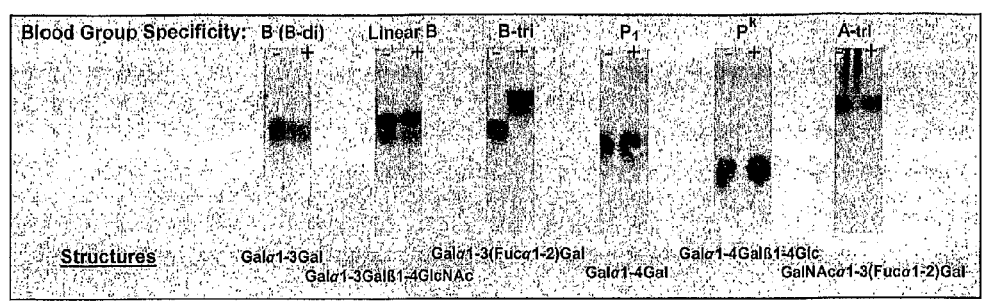
B. Substrate specificity of BFβ1 (FragB) α-galactosidase.
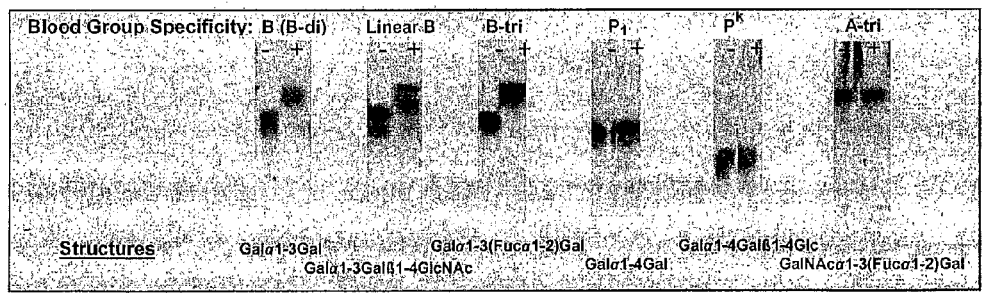

SEQUENCE LISTING

<160> NUMBER OF SEQ ID NOS: 29

<210> SEQ ID NO 1
<211> LENGTH: 8
<212> TYPE: PRT
<213> ORGANISM: Streptomyces griseoplanus -continued

```
<400> SEQUENCE: 1

Phe Ala Asn Gly Leu Leu Leu Thr
1               5

<210> SEQ ID NO 2
<211> LENGTH: 625
<212> TYPE: PRT
<213> ORGANISM: Streptomyces avermitilis

<400> SEQUENCE: 2

Met Ala His Gly Cys Ser Gly Gly Ala Met Ser Arg Phe Val Phe Leu
1               5                   10                  15

Gly Val Ala Leu Ala Leu Leu Gly Gly Ala Thr Ser Pro Ala Ala Ala
            20                  25                  30

Ala Pro Arg Val Thr Pro Val Val Asp Val Asp Asp Tyr Gly Ala
        35                  40                  45

Asp Pro Thr Gly Arg Thr Asp Ser Thr Pro Ala Val Ala Ala Leu
    50                  55                  60

Arg His Ala Lys Ser Val Asp Arg Pro Val Arg Ile Val Phe Ser Lys
65                  70                  75                  80

Gly Thr Tyr Gln Leu Tyr Pro Glu Arg Ala Glu Thr Arg Glu Leu Tyr
                85                  90                  95

Met Ser Asn Thr Val Gly Ala Asp Gln Arg Tyr Arg Asp Lys Lys Ile
            100                 105                 110

Gly Leu Leu Val Glu Asp Met His Asp Val Thr Val Asp Gly Gly Gly
        115                 120                 125

Ala Lys Leu Val His His Gly Leu Gln Thr Ala Phe Ala Ser Ile Arg
    130                 135                 140

Ser Thr Asp Val Thr Phe Gln Asn Phe Ser Phe Asp Tyr Ala Ala Pro
145                 150                 155                 160

Glu Val Ile Asp Ala Thr Val Ala Thr Gly Val Thr Asp Gly His
                165                 170                 175

Ala Tyr Arg Val Leu Lys Ile Pro Ala Gly Ser Pro Tyr Arg Val Asn
            180                 185                 190

Gly Thr His Ile Thr Trp Leu Gly Glu Thr Ser Pro Ala Thr Gly Gln
        195                 200                 205

Pro Tyr Trp Ser Gly Val Asp Gly Leu Gln Tyr Thr Gln Ile His Asp
    210                 215                 220

Pro Glu Ala Gln Arg Thr Trp Arg Gly Asp Asn Pro Leu Phe Asn Asp
225                 230                 235                 240

Val Ala Ala Val Thr Asp Leu Gly Gly Arg Arg Ile Arg Ile Asp Tyr
                245                 250                 255

Thr Thr Ala Ala Arg Pro Ala Asp Ala Gly Leu Val Tyr Gln Met Arg
            260                 265                 270

Leu Ile Glu Arg Thr Glu Pro Gly Ala Phe Ile Trp Glu Ser Lys Asn
        275                 280                 285

Val Thr Met Arg Ser Met Asn Ala Tyr Tyr Leu Gln Ser Phe Gly Val
    290                 295                 300

Val Gly Gln Phe Ser Glu Asn Ile Ser Ile Asp Lys Val Asn Phe Ala
305                 310                 315                 320

Pro Asp Pro Arg Ser Gly Arg Ser Thr Ala Ser Phe Ala Asp Phe Val
                325                 330                 335

Gln Met Ser Gly Val Lys Gly Lys Val Ser Ile Thr Arg Ser Leu Phe
            340                 345                 350

Asp Gly Pro His Asp Asp Pro Ile Asn Ile His Gly Thr Tyr Leu Glu
```

```
                 355                 360                 365
Val Val Gly Lys Pro Gly Pro Ser Thr Leu Thr Leu Ala Tyr Lys His
        370                 375                 380

Pro Gln Thr Ala Gly Phe Pro Gln Phe Ala Pro Gly Asp Glu Val Glu
385                 390                 395                 400

Phe Ala Thr Lys Arg Thr Met Thr Pro Leu Ala Asp Ala His Ala Gln
                405                 410                 415

Val Thr Ala Val Asp Gly Pro Ser Gly Met Asp His Thr Lys Pro Leu
            420                 425                 430

Thr Thr Met Thr Val Thr Phe Asp Arg Pro Val Pro Ala Gly Val Glu
        435                 440                 445

Thr Gly Gly Thr Val Val Glu Asn Ile Thr Ala Thr Pro Ser Val Val
    450                 455                 460

Ile Ser Gly Asn Val Phe Arg Asn Val Pro Thr Arg Gly Ile Leu Val
465                 470                 475                 480

Thr Thr Arg Lys Pro Val Leu Ile Thr Gly Asn Arg Phe Asp Gly Met
                485                 490                 495

Ser Met Ala Ser Ile Tyr Val Ser Ala Asp Ala Tyr Gln Trp Tyr Glu
            500                 505                 510

Ser Gly Pro Val Ala Asp Leu Thr Ile Arg Gly Asn Ser Phe Thr Arg
        515                 520                 525

Pro Ser Gly Pro Val Ile Phe Val Glu Pro Thr Asn Gln Val Ile Asp
    530                 535                 540

Pro Ala Thr Pro Val His His Asn Ile Ser Val Glu His Asn Ser Phe
545                 550                 555                 560

Asp Ile Gly Asp Val Thr Val Val Asn Ala Lys Ser Val Gly Gly Phe
                565                 570                 575

Ala Phe Thr Gly Asn Thr Val Arg Arg Leu Asp Gly Ala Asp His Pro
            580                 585                 590

Pro Tyr Thr Ser Pro Leu Phe Val Phe His Gly Ser Ser Gly Ile Arg
        595                 600                 605

Ile Ala Arg Asn His Tyr Asp Lys Gly Leu Asn Thr Ser Val Val Thr
    610                 615                 620

Asp
625

<210> SEQ ID NO 3
<211> LENGTH: 568
<212> TYPE: PRT
<213> ORGANISM: Bacteroides thetaotaomicron

<400> SEQUENCE: 3

Met Met Ser Val Trp Phe Ile Gln Leu Ala Ile Phe Ala Gln Ser Arg
1               5                   10                  15

Ile Ile Glu Val Phe Pro Glu Gln Gly Lys Asp Ile Glu Asn Ile Ala
            20                  25                  30

Leu Ala Leu Lys Lys Ala Ala Asp Cys Lys Gly Arg Pro Val Thr Val
        35                  40                  45

Lys Phe Ser Pro Gly Ile Tyr Gln Leu Asp Arg Ala Lys Ser Ser Gln
    50                  55                  60

Val Leu Tyr Tyr Ile Ser Asn Thr Thr Ser Glu Leu Asp Asp Pro Asp
65                  70                  75                  80

Pro Thr Lys His Ile Gly Leu Tyr Leu Asn Thr Leu Lys Asn Ile Thr
                85                  90                  95

Ile Asp Gly Cys Gly Ser Thr Leu Leu Met Asn Gly Glu Met Thr Ser
```

-continued

```
                100             105             110
Phe Val Leu Asp Lys Cys Glu Gly Ile Val Leu Lys Asn Phe Asn Ile
            115             120             125
Asp Tyr Lys His Pro Thr Gln Thr Glu Val Glu Val Leu Glu Glu Gly
            130             135             140
Asn Asp Tyr Leu Ile Val Gln Val His Pro Thr Ser Gln Tyr Arg Ile
145             150             155             160
Val Asp Ala Gln Leu Glu Trp Tyr Gly Asp Gly Trp Ser Phe Lys Asn
            165             170             175
Gly Ile Ala Gln Ser Tyr Asp Arg Ile Ser Glu Met Thr Trp Arg Ser
            180             185             190
Trp Ser Pro Met Glu Asn Leu Leu Arg Thr Val Glu Leu Arg Pro Asn
            195             200             205
Val Leu Tyr Leu Gln Tyr Lys Glu Lys Pro Gln Val Gly Leu His Thr
            210             215             220
Ile Phe Gln Met Arg Asp Ser Phe Arg Asp Glu Val Ser Gly Phe Val
225             230             235             240
Asn Arg Ser Lys Gly Ile Leu Leu Glu Asn Ile Asn Phe Tyr Tyr Leu
            245             250             255
Gly Asn Phe Gly Val Val Cys Gln Tyr Ser Glu Asn Ile Thr Val Asp
            260             265             270
Arg Cys Asn Phe Ala Pro Arg Pro Gly Ser Gly Arg Thr Asn Ala Gly
            275             280             285
Phe Ala Asp Phe Ile Gln Val Ser Gly Cys Arg Gly Met Ile Asp Ile
            290             295             300
Lys Asn Ser Arg Phe Ile Gly Ala His Asp Asp Pro Ile Asn Ile His
305             310             315             320
Gly Thr His Leu Arg Val Ile Glu Phe Leu Ser Asp Asn Arg Leu Lys
            325             330             335
Leu Arg Phe Met His Asp Gln Thr Phe Gly Phe Glu Ala Phe Phe Lys
            340             345             350
Gly Asp Asp Ile Glu Leu Val Asp Ser Arg Ser Leu Leu Val Val Gly
            355             360             365
Lys Cys Lys Val Lys Glu Ala Lys Leu Val Thr Pro Arg Glu Met Glu
            370             375             380
Leu Thr Leu Ser Ser Pro Leu Ser Ser Glu Val Met Gln Gln Lys Asp
385             390             395             400
Leu Val Ile Glu Asn Val Thr Trp Thr Pro Glu Val Arg Ile Thr Asn
            405             410             415
Asn Tyr Phe Ala Arg Val Pro Thr Arg Gly Ile Leu Ile Thr Thr Arg
            420             425             430
Arg Lys Ser Leu Ile Glu Gly Asn Thr Phe Tyr Gly Met Gln Met Ser
            435             440             445
Gly Ile Phe Val Ala Asp Asp Gly Leu Ser Trp Tyr Glu Ser Gly Pro
            450             455             460
Val His Asp Leu Thr Ile Arg Gln Asn Thr Phe Leu Asn Cys Gly Glu
465             470             475             480
Pro Ile Ile Ser Ile Asp Pro Glu Asn Arg Glu Tyr Lys Gly Ala Val
            485             490             495
His Lys Asn Ile Thr Ile Glu Glu Asn Tyr Phe Tyr Met Arg Lys Asn
            500             505             510
Ser Ser Cys Ala Ile Arg Ala Lys Ala Val Asp Gly Leu Met Ile Arg
            515             520             525
```

-continued

```
His Asn Leu Ile Tyr Ser Leu Asp Thr Glu Lys Asn Lys Glu Ser Asp
            530                 535                 540

Phe Ile Gln Met Tyr Asn Cys Asn Glu Val Thr Ile Lys Glu Asn Arg
545                 550                 555                 560

Val Gln Leu His His Leu Phe Lys
                565

<210> SEQ ID NO 4
<211> LENGTH: 605
<212> TYPE: PRT
<213> ORGANISM: Bacteroides fragilis

<400> SEQUENCE: 4

Met Lys Lys Tyr Leu His Ile Leu Pro Ala Cys Phe Leu Phe Tyr Ala
1               5                   10                  15

Ala Ala His Ala Gln Gln Lys Asp Thr Val Tyr Val Thr Asp Phe Gly
            20                  25                  30

Ala Val Pro Tyr Ser Tyr Glu Asn Cys Val Thr Gln Ile Gln Ala Ala
            35                  40                  45

Ile Asp Glu Cys Lys Arg Thr Gly Ala Lys Val Leu Ser Leu Pro Glu
50                  55                  60

Gly Arg Tyr Asp Ile Trp Pro Glu Gly Ala Thr Arg Lys Glu Tyr Tyr
65                  70                  75                  80

Ile Ser Asn Thr Ser Thr Glu Gln Glu Cys Pro Ser Lys Val Lys Thr
                85                  90                  95

Val Gly Leu Met Leu His Glu Ile Asp Asp Leu Thr Ile Glu Gly Asn
            100                 105                 110

Gly Ala Thr Leu Met Tyr His Gly Lys Met Thr Thr Ile Ala Leu Glu
            115                 120                 125

His Cys Asn Gly Val Arg Ile Asn Asn Leu His Ile Asp Phe Glu Arg
130                 135                 140

Pro Ala Gly Ser Glu Ile Gln Tyr Arg Lys Val Thr Gly Gly Glu Thr
145                 150                 155                 160

Glu Val Thr Leu His Arg Asp Thr Arg Tyr Glu Ile Val Asn Gly Lys
                165                 170                 175

Ile Arg Leu Tyr Gly Glu Gly Trp Arg Ser Asn Lys Asn His Cys Ile
            180                 185                 190

Glu Tyr Asp Pro Asp Thr Glu Ser Phe Thr Tyr Ser Gln Gly Trp Asn
            195                 200                 205

Thr Leu Ser Ala Ser Asp Ala Arg Glu Ile Ala Pro Gly Ile Val Arg
210                 215                 220

Phe Asn Thr Pro Ala Glu Phe Met Pro Lys Ala Gly Asn Thr Leu Thr
225                 230                 235                 240

Val Arg Asp Ile Ile Arg Asp Gln Val Gly Phe Phe Ile Leu Glu Ser
                245                 250                 255

Lys Asn Ile Thr Leu Ser Arg Leu Gln Met His Tyr Met His Gly Leu
            260                 265                 270

Gly Ile Val Ser Gln Tyr Thr Glu Asn Ile Thr Met Asp Arg Val Lys
            275                 280                 285

Cys Ala Pro Arg Pro Asp Ser Gly Arg Leu Leu Ala Ala Ser Ala Asp
290                 295                 300

Met Met His Phe Ser Gly Cys Lys Gly Lys Val Ile Ile Asp Ser Cys
305                 310                 315                 320

Tyr Phe Ala Gly Ala Gln Asp Asp Pro Val Asn Val His Gly Thr Asn
                325                 330                 335
```

-continued

Leu Arg Ala Leu Glu Lys Ile Asp Ala Gln Thr Leu Lys Leu Arg Phe
            340                 345                 350

Met His Gly Gln Ser Tyr Gly Phe Asn Ala Tyr Phe Lys Gly Asp Thr
        355                 360                 365

Val Ala Phe Ile Arg Ala Ala Thr Met Glu Arg Phe Ala Ser Ala Thr
370                 375                 380

Val Arg Asp Val Arg Arg Ile Ser Asp Arg Ile Val Glu Val Arg Phe
385                 390                 395                 400

Asp Arg Asp Ile Pro Thr Ser Leu Glu Leu Asn His Asp Cys Val Glu
                405                 410                 415

Asn Met Thr Cys Thr Pro Glu Val Glu Ile Arg Asn Ser Tyr Phe Thr
            420                 425                 430

Arg Thr Ser Thr Arg Gly Thr Leu Val Thr Thr Pro Arg Lys Val Val
        435                 440                 445

Ile Glu Asn Asn Thr Tyr Tyr Lys Thr Gly Met Ser Ala Ile Leu Ile
    450                 455                 460

Glu Ala Asp Ala Glu Gly Trp Tyr Glu Ser Gly Pro Val Lys Asp Val
465                 470                 475                 480

Leu Ile Lys Gly Asn Thr Phe Ile Asp Cys Ala Tyr Asn Gly Gly Pro
                485                 490                 495

Gly His Ala Val Ile Ala Ile His Pro Ser Asn Lys Ile Ile Asp Ala
            500                 505                 510

Glu Arg Pro Val His Gln Asn Ile Arg Ile Glu Asp Asn Thr Phe Arg
        515                 520                 525

Thr Phe Asp Tyr Pro Val Leu Tyr Ala Lys Ser Thr Ala Gly Leu Leu
    530                 535                 540

Phe Arg Asn Asn Thr Ile Val Arg Thr Glu Thr Phe Pro Ala Ala Ser
545                 550                 555                 560

Gly Asn Pro Tyr Val Phe Tyr Leu Asn Gly Cys Lys Lys Ala Val Ile
                565                 570                 575

Glu Gly Thr Val Phe Lys Gly Glu Thr Pro Arg Gln Ser Ile Lys Thr
            580                 585                 590

Glu Asn Met Lys Arg Lys Asp Leu Lys Thr Thr Ile Lys
        595                 600                 605

<210> SEQ ID NO 5
<211> LENGTH: 605
<212> TYPE: PRT
<213> ORGANISM: Bacteroides fragilis

<400> SEQUENCE: 5

Met Lys Lys Tyr Leu His Ile Leu Pro Ala Cys Phe Leu Phe Tyr Ala
1               5                   10                  15

Ala Ala His Ala Gln Gln Lys Asp Thr Val Tyr Val Thr Asp Phe Gly
            20                  25                  30

Ala Val Pro Tyr Ser Tyr Glu Asn Cys Val Thr Gln Ile Gln Ala Ala
        35                  40                  45

Ile Asp Glu Cys Lys Arg Thr Gly Ala Lys Val Leu Ser Leu Pro Glu
    50                  55                  60

Gly Arg Tyr Asp Ile Trp Pro Glu Gly Ala Ile Arg Lys Glu Tyr Tyr
65                  70                  75                  80

Ile Ser Asn Thr Ser Thr Glu Gln Glu Cys Pro Ser Lys Val Lys Thr
                85                  90                  95

Val Gly Leu Met Leu His Glu Ile Asp Asp Leu Thr Ile Glu Gly Asn
            100                 105                 110

```
Gly Ala Thr Leu Met Tyr His Gly Lys Met Thr Thr Ile Ala Leu Glu
            115                 120                 125

His Cys Asn Gly Val Arg Ile Asn Asn Leu His Ile Asp Phe Glu Arg
130                 135                 140

Pro Ala Gly Ser Glu Ile Gln Tyr Arg Lys Val Thr Gly Gly Glu Thr
145                 150                 155                 160

Glu Val Thr Leu His Arg Asp Thr Arg Tyr Glu Ile Val Asn Gly Lys
                165                 170                 175

Ile Arg Leu Tyr Gly Glu Gly Trp Arg Ser Asn Arg Asn His Cys Ile
            180                 185                 190

Glu Tyr Asp Pro Asp Thr Glu Ser Phe Thr Tyr Ser Gln Gly Trp Asn
        195                 200                 205

Thr Leu Ser Ala Ser Asp Ala Arg Glu Ile Ala Pro Gly Ile Val Arg
    210                 215                 220

Phe Asn Thr Pro Ala Glu Phe Met Pro Lys Ala Gly Asn Thr Leu Thr
225                 230                 235                 240

Val Arg Asp Ile Ile Arg Asp Gln Val Gly Leu Phe Ile Leu Glu Ser
                245                 250                 255

Lys Asn Ile Thr Leu Ser Arg Leu Gln Met His Tyr Met His Gly Leu
            260                 265                 270

Gly Ile Val Ser Gln Tyr Thr Glu Asn Ile Thr Met Asp Arg Val Lys
        275                 280                 285

Cys Ala Pro Arg Pro Asp Ser Gly Arg Leu Leu Ala Ala Ser Ala Asp
    290                 295                 300

Met Met His Phe Ser Gly Cys Lys Gly Lys Val Ile Ile Asp Ser Cys
305                 310                 315                 320

Tyr Phe Ala Gly Ala Gln Asp Asp Pro Val Asn Val His Gly Thr Asn
                325                 330                 335

Leu Arg Ala Leu Glu Lys Ile Asp Ala Gln Thr Leu Lys Leu Arg Phe
            340                 345                 350

Met His Gly Gln Ser Tyr Gly Phe Asn Ala Tyr Phe Lys Gly Asp Thr
        355                 360                 365

Val Ala Phe Val Arg Ala Ala Thr Met Glu Arg Phe Ala Ser Ala Thr
    370                 375                 380

Val Arg Asp Val Arg Arg Ile Ser Asp Arg Ile Val Glu Val Arg Phe
385                 390                 395                 400

Asp Arg Asp Ile Pro Thr Ser Leu Glu Leu Asn His Asp Cys Val Glu
                405                 410                 415

Asn Met Thr Cys Thr Pro Glu Val Glu Ile Arg Asn Cys Tyr Phe Thr
            420                 425                 430

Arg Thr Ser Thr Arg Gly Thr Leu Val Thr Thr Pro Arg Lys Val Val
        435                 440                 445

Ile Glu Asn Asn Thr Tyr Tyr Lys Thr Gly Met Ser Ala Ile Leu Ile
    450                 455                 460

Glu Ala Asp Ala Glu Gly Trp Tyr Glu Ser Gly Pro Val Lys Asp Val
465                 470                 475                 480

Leu Ile Lys Gly Asn Thr Phe Ile Asp Cys Ala Tyr Asn Gly Gly Pro
                485                 490                 495

Gly His Ala Val Ile Ala Ile His Pro Ser Asn Lys Ile Ile Asp Ala
            500                 505                 510

Glu Arg Pro Val His Gln Asn Ile Arg Ile Glu Asp Asn Thr Phe Arg
        515                 520                 525

Thr Phe Asp Tyr Pro Val Leu Tyr Ala Lys Ser Thr Ala Gly Leu Leu
    530                 535                 540
```

```
Phe Arg Asn Asn Thr Ile Val Arg Thr Glu Thr Phe Pro Ala Val Ser
545                 550                 555                 560

Gly Asn Pro Tyr Val Phe Tyr Leu Asn Gly Cys Lys Lys Ala Val Ile
            565                 570                 575

Glu Gly Thr Val Phe Glu Gly Thr Pro Arg Gln Ser Ile Lys Thr
                580                 585                 590

Glu Asn Met Lys Arg Lys Asp Leu Lys Thr Thr Ile Lys
        595                 600                 605
```

<210> SEQ ID NO 6
<211> LENGTH: 595
<212> TYPE: PRT
<213> ORGANISM: Bacteroides fragilis

<400> SEQUENCE: 6

```
Met Lys Thr Ile Leu Leu Phe Ala Leu Ser Leu Leu Ser Leu Ser
1               5                   10                  15

Val Ser Asp Val Cys Ala Gln Glu Arg Val Tyr Asp Ile Ser Gln Phe
                20                  25                  30

Gly Leu Lys Ala Asn Ser Lys Lys Asn Ala Ser Pro Val Val Arg Lys
            35                  40                  45

Ala Ile Ala Lys Ile Lys Ala Glu Cys Arg Asp Gly Glu Lys Val Ile
        50                  55                  60

Leu Arg Phe Pro Ala Gly Arg Tyr Asn Phe His Glu Ala Gly Ser Thr
65                  70                  75                  80

Val Arg Glu Tyr Tyr Ile Ser Asn His Asp Gln Asp Asn Pro Lys Lys
                85                  90                  95

Val Gly Ile Ala Leu Glu Asp Met Lys Asn Leu Thr Ile Asp Gly Gln
            100                 105                 110

Gly Ser Glu Phe Val Phe Tyr Gly Arg Met Ile Pro Val Ser Leu Leu
        115                 120                 125

Arg Ser Glu Asn Cys Val Leu Lys Asn Phe Ser Ile Asp Phe Glu Gln
    130                 135                 140

Pro His Ile Ala Gln Val Gln Val Val Glu Asn Asp Pro Glu Lys Gly
145                 150                 155                 160

Ile Thr Phe Glu Pro Ala Pro Trp Val Asp Tyr Arg Ile Ser Lys Asp
                165                 170                 175

Ser Val Phe Glu Gly Leu Gly Glu Gly Trp Val Met Arg Tyr Ser Trp
            180                 185                 190

Gly Ile Ala Phe Asp Gly Lys Thr Lys His Val Val Tyr Asn Thr Ser
        195                 200                 205

Asp Ile Gly Cys Pro Thr Lys Gly Ala Phe Glu Val Ala Pro Arg Arg
    210                 215                 220

Ile Cys Ser Pro Lys Trp Lys Asp Ala Arg Leu Val Pro Gly Thr Val
225                 230                 235                 240

Val Ala Met Arg Gly Trp Gly Arg Pro Thr Pro Gly Ile Phe Met Ser
                245                 250                 255

His Asp Val Asn Thr Ser Leu Leu Asp Val Lys Val His Tyr Ala Glu
            260                 265                 270

Gly Met Gly Leu Leu Ala Gln Leu Cys Glu Asp Ile Thr Leu Asp Gly
        275                 280                 285

Phe Gly Val Cys Leu Lys Gly Asn Asn Asp Pro Arg Tyr Phe Thr Thr
    290                 295                 300

Gln Ala Asp Ala Thr His Phe Ser Gly Cys Lys Gly Lys Ile Val Ser
305                 310                 315                 320
```

```
Lys Asn Gly Leu Tyr Glu Gly Met Met Asp Asp Ala Ile Asn Val His
                325                 330                 335

Gly Thr Tyr Leu Lys Val Ile Lys Arg Val Asp Asp His Thr Leu Ile
                340                 345                 350

Gly Arg Tyr Met His Asp Gln Ser Trp Gly Phe Glu Trp Gly Arg Pro
                355                 360                 365

Gly Asp Asp Val Gln Phe Val Arg Ser Glu Thr Met Glu Leu Ile Gly
                370                 375                 380

Lys Gln Asn Gln Ile Thr Ala Ile Arg Pro Tyr Asp Lys Gly Glu Ile
385                 390                 395                 400

Gln Gly Ala Arg Glu Phe Ser Ile Thr Phe Lys Glu Ala Ile Asp Pro
                405                 410                 415

Ala Ile Asn Glu Lys Ser Gly Phe Gly Ile Glu Asn Leu Thr Trp Thr
                420                 425                 430

Pro Glu Val Leu Phe Ala Gly Asn Thr Ile Arg Asn Asn Arg Ala Arg
                435                 440                 445

Gly Thr Leu Phe Ser Thr Pro Lys Lys Thr Val Val Glu Asp Asn Leu
                450                 455                 460

Phe Asp His Thr Ser Gly Thr Ala Ile Leu Leu Cys Gly Asp Cys Asn
465                 470                 475                 480

Gly Trp Phe Glu Thr Gly Ala Cys Arg Asp Val Thr Ile Arg Arg Asn
                485                 490                 495

Arg Phe Ile Asn Ala Leu Thr Asn Met Phe Gln Phe Thr Asn Ala Val
                500                 505                 510

Ile Ser Ile Tyr Pro Glu Ile Pro Asn Leu Lys Asp Gln Gln Lys Tyr
                515                 520                 525

Phe His Gly Gly Lys Asp Gly Gly Ile Val Ile Glu Asp Asn Glu Phe
                530                 535                 540

Asp Thr Phe Asp Ala Pro Ile Leu Tyr Ala Lys Ser Val Asp Gly Leu
545                 550                 555                 560

Ile Phe Arg Asn Asn Val Ile Lys Thr Asn Thr Glu Phe Lys Pro Phe
                565                 570                 575

His Trp Asn Lys Asp Arg Phe Leu Leu Glu Arg Val Thr Asn Val Lys
                580                 585                 590

Ile Ser Glu
        595

<210> SEQ ID NO 7
<211> LENGTH: 595
<212> TYPE: PRT
<213> ORGANISM: Bacteroides fragilis

<400> SEQUENCE: 7

Met Lys Thr Ile Leu Leu Phe Ala Leu Ser Leu Leu Leu Ser Leu Ser
1               5                   10                  15

Val Ser Asp Val Cys Ala Gln Glu Arg Val Tyr Asp Ile Ser Gln Phe
                20                  25                  30

Gly Leu Lys Ala Asn Ser Lys Lys Asn Ala Ser Pro Val Val Arg Lys
                35                  40                  45

Ala Ile Ala Lys Ile Lys Ala Glu Cys Arg Asp Gly Glu Lys Val Ile
                50                  55                  60

Leu Arg Phe Pro Ala Gly Arg Tyr Asn Phe His Glu Ala Gly Ser Thr
65                  70                  75                  80

Val Arg Glu Tyr Tyr Ile Ser Asn His Asp Gln Asp Asn Pro Lys Lys
                85                  90                  95
```

```
Val Gly Ile Ala Leu Glu Asp Met Lys Asn Leu Thr Ile Asp Gly Gln
            100                 105                 110

Gly Ser Glu Phe Val Phe Tyr Gly Arg Met Ile Pro Val Ser Leu Leu
        115                 120                 125

Arg Ser Glu Asn Cys Val Leu Lys Asn Phe Ser Ile Asp Phe Glu Gln
130                 135                 140

Pro His Ile Ala Gln Val Gln Val Val Glu Asn Asp Pro Glu Lys Gly
145                 150                 155                 160

Ile Thr Phe Glu Pro Ala Pro Trp Val Asp Tyr Arg Ile Ser Lys Asp
                165                 170                 175

Ser Val Phe Glu Gly Leu Gly Glu Gly Trp Val Met Arg Tyr Ser Trp
            180                 185                 190

Gly Ile Ala Phe Asp Gly Lys Thr Lys His Val Val Tyr Asn Thr Ser
        195                 200                 205

Asp Ile Gly Cys Pro Thr Lys Gly Ala Phe Glu Val Ala Pro Arg Arg
    210                 215                 220

Ile Cys Ser Pro Lys Trp Lys Asp Ala Arg Leu Val Pro Gly Thr Val
225                 230                 235                 240

Val Ala Met Arg Gly Trp Gly Arg Pro Thr Pro Gly Ile Phe Met Ser
                245                 250                 255

His Asp Val Asn Thr Ser Leu Leu Asp Val Lys Val His Tyr Ala Glu
            260                 265                 270

Gly Met Gly Leu Leu Ala Gln Leu Cys Glu Asp Ile Thr Leu Asp Gly
        275                 280                 285

Phe Gly Val Cys Leu Lys Gly Asp Asn Asp Pro Arg Tyr Phe Thr Thr
    290                 295                 300

Gln Ala Asp Ala Thr His Phe Ser Gly Cys Lys Gly Lys Ile Val Ser
305                 310                 315                 320

Lys Asn Gly Leu Tyr Glu Gly Met Met Asp Asp Ala Ile Asn Val His
                325                 330                 335

Gly Thr Tyr Leu Lys Val Ile Lys Arg Val Asp Asp His Thr Leu Ile
            340                 345                 350

Gly Arg Tyr Met His Asp Gln Ser Trp Gly Phe Glu Trp Gly Arg Pro
        355                 360                 365

Gly Asp Asp Val Gln Phe Val Arg Ser Glu Thr Met Glu Leu Ile Gly
    370                 375                 380

Lys Gln Asn Gln Ile Thr Ala Ile Arg Pro Tyr Asp Lys Gly Glu Ile
385                 390                 395                 400

Arg Gly Ala Arg Glu Phe Ser Ile Thr Phe Lys Glu Ala Ile Asp Pro
                405                 410                 415

Ala Ile Asn Glu Lys Ser Gly Phe Gly Ile Glu Asn Leu Thr Trp Thr
            420                 425                 430

Pro Glu Val Leu Phe Ala Gly Asn Thr Ile Arg Asn Asn Arg Ala Arg
        435                 440                 445

Gly Thr Leu Phe Ser Thr Pro Lys Lys Thr Val Val Glu Asp Asn Leu
    450                 455                 460

Phe Asp His Thr Ser Gly Thr Ala Ile Leu Leu Cys Gly Asp Cys Asn
465                 470                 475                 480

Gly Trp Phe Glu Thr Gly Ala Cys Arg Asp Val Thr Ile Arg Arg Asn
                485                 490                 495

Arg Phe Ile Asn Ala Leu Thr Asn Met Phe Gln Phe Thr Asn Ala Val
            500                 505                 510

Ile Ser Ile Tyr Pro Glu Ile Pro Asn Leu Lys Asp Gln Gln Lys Tyr
```

```
                515                 520                 525
Phe His Gly Gly Lys Asp Gly Ile Val Ile Glu Asp Asn Glu Phe
530                 535                 540

Asp Thr Phe Asp Ala Pro Ile Leu Tyr Ala Lys Ser Val Asp Gly Leu
545                 550                 555                 560

Ile Phe Arg Asn Asn Val Ile Lys Thr Asn Thr Glu Phe Lys Pro Phe
                565                 570                 575

His Trp Asn Lys Asp Arg Phe Leu Leu Glu Arg Val Thr Asn Val Lys
            580                 585                 590

Ile Ser Glu
        595

<210> SEQ ID NO 8
<211> LENGTH: 615
<212> TYPE: PRT
<213> ORGANISM: Bacteroides thetaotaomicron

<400> SEQUENCE: 8

Met Arg Thr Phe Leu Ser Leu Lys Thr Cys Leu Leu Ser Ala Leu Leu
1               5                   10                  15

Leu Cys Val Asn Ser Ile Ala Ala Ser Lys Ile Ile Ser Val Ser Asp
                20                  25                  30

Phe Gly Leu Lys Pro Asp Ser Arg Ile Asn Ala Val Pro Phe Ile Gln
            35                  40                  45

Lys Ala Ile Asp Ala Cys Lys Gln His Pro Gly Ser Thr Leu Val Phe
        50                  55                  60

Pro Lys Gly Arg Tyr Asp Phe Trp Ala Gln His Ala Ile Glu Lys Asp
65                  70                  75                  80

Tyr Tyr Glu Thr Asn Thr Tyr Asp Val Asn Pro Lys Ile Leu Ala Val
                85                  90                  95

Leu Leu Glu Gln Ile Asn Asp Leu Thr Ile Asp Gly Asn Gly Ser Glu
            100                 105                 110

Phe Ile Met His Gly Arg Met Gln Pro Phe Thr Leu Asp His Cys Arg
        115                 120                 125

Asn Ile Thr Leu Lys Asn Phe Ser Val Asp Trp Glu Ile Pro Leu Thr
130                 135                 140

Ala Gln Gly Ile Val Thr Gln Ser Thr Ser Glu Tyr Leu Glu Ile Glu
145                 150                 155                 160

Ile Asp Ser His Gln Tyr Pro Tyr Ile Ile Glu Asn Lys Arg Leu Thr
                165                 170                 175

Phe Val Gly Glu Gly Trp Lys Ser Ser Leu Trp Ala Ile Met Gln Phe
            180                 185                 190

Asp Pro Asp Thr His Leu Val Leu Pro Asn Thr Gly Asp Asn Leu Gly
        195                 200                 205

Trp Arg Ser Tyr Asp Ala Thr Glu Ile Asn Pro Gly Leu Ile Arg Leu
210                 215                 220

Ser Asp Pro Lys Lys Glu Ala Asp Lys Phe Phe Pro Ala Pro Gly Thr
225                 230                 235                 240

Val Leu Val Leu Arg His Ser Thr Arg Asp His Ala Gly Ile Phe Ile
                245                 250                 255

Tyr His Ser Met Asp Thr Lys Leu Glu Asn Val Lys Leu Phe His Thr
            260                 265                 270

Cys Gly Leu Gly Ile Leu Ser Gln Tyr Ser Lys Asn Ile Ser Phe Asn
        275                 280                 285

Asp Val His Ile Ile Pro Asn Thr Ser Lys Lys Arg Val Leu Ser Gly
```

-continued

```
                    290                 295                 300
His Asp Asp Gly Phe His Phe Met Gly Cys Ser Gly Leu Leu Lys Ile
305                 310                 315                 320

Glu Asn Cys Ser Trp Ala Gly Leu Met Asp Asp Pro Ile Asn Ile His
                325                 330                 335

Gly Thr Cys Ser Arg Ile Met Glu Val Leu Ser Pro Thr Arg Ile Lys
            340                 345                 350

Cys Lys Phe Met Gln Asp Met Ser Glu Gly Met Glu Trp Gly Arg Pro
            355                 360                 365

Asp Glu Thr Ile Gly Phe Ile Glu His Lys Thr Met Arg Thr Val Ala
        370                 375                 380

Thr Gly Lys Met Asn Lys Phe Glu Ala Leu Asn Lys Ala Glu Phe Ile
385                 390                 395                 400

Ile Glu Leu Ser Val Pro Leu Pro Ala Gly Val Glu Ala Gly Tyr Val
                405                 410                 415

Ile Glu Asn Leu Thr Cys Thr Pro Asp Ala Glu Ile Arg Asn Cys His
            420                 425                 430

Phe Gly Ser Cys Arg Ala Arg Gly Leu Leu Val Ser Thr Pro Gly Lys
        435                 440                 445

Val Ile Ile Glu Asn Asn Val Phe Glu Ser Ser Gly Ser Ala Ile Leu
    450                 455                 460

Ile Ala Gly Asp Ala Asn Ala Trp Tyr Glu Gly Ala Val Lys Asp
465                 470                 475                 480

Val Leu Ile Arg Asn Asn Asp Phe Arg Tyr Pro Cys Asn Ser Ser Ile
                485                 490                 495

Tyr Gln Phe Cys Glu Ala Val Ile Ser Ile Asp Pro Glu Ile Pro Thr
            500                 505                 510

Pro Glu Gln Lys Tyr Pro Tyr His Arg Asn Ile Arg Ile Met Asp Asn
        515                 520                 525

Thr Phe His Leu Phe Asp Tyr Pro Ile Leu Phe Ala Arg Ser Val Asn
    530                 535                 540

Gly Leu Thr Phe Ser Ser Asn Thr Leu Ile Arg Asp Thr Thr Tyr Gln
545                 550                 555                 560

Pro Tyr His Tyr Arg Lys Glu Gly Ile Thr Leu Glu Ala Cys Lys Ser
                565                 570                 575

Val Val Ile Ser Asn Asn Lys Ile Glu Gly Asp Val Leu Gly Arg Ile
            580                 585                 590

Val Thr Ile Glu Lys Met Lys Pro Ser Asp Val Lys Ile Ser Lys Asn
        595                 600                 605

Pro Phe Phe Lys Leu Lys Lys
    610                 615
```

<210> SEQ ID NO 9
<211> LENGTH: 665
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (13)..(13)
<223> OTHER INFORMATION: Phe, Val, Tyr or Ile
<220> FEATURE:
<221> NAME/KEY: MOD_RES
<222> LOCATION: (15)..(15)
<223> OTHER INFORMATION: Phe, His, Leu or Ser
<220> FEATURE:
<221> NAME/KEY: MOD_RES -continued

```
<222> LOCATION: (17)..(17)
<223> OTHER INFORMATION: Gly, Gln, Leu, Ala or Lys
<220> FEATURE:
<221> NAME/KEY: MOD_RES
<222> LOCATION: (21)..(21)
<223> OTHER INFORMATION: Ala, Phe or Leu
<220> FEATURE:
<221> NAME/KEY: MOD_RES
<222> LOCATION: (23)..(23)
<223> OTHER INFORMATION: Leu, Gln, Phe, Ser or Ala
<220> FEATURE:
<221> NAME/KEY: MOD_RES
<222> LOCATION: (25)..(25)
<223> OTHER INFORMATION: Gly, Ala, Ser or Leu
<220> FEATURE:
<221> NAME/KEY: MOD_RES
<222> LOCATION: (27)..(27)
<223> OTHER INFORMATION: Thr, Ala, Ser or Cys
<220> FEATURE:
<221> NAME/KEY: MOD_RES
<222> LOCATION: (28)..(28)
<223> OTHER INFORMATION: Ser, His, Asp or Val
<220> FEATURE:
<221> NAME/KEY: MOD_RES
<222> LOCATION: (29)..(29)
<223> OTHER INFORMATION: Pro or Asn
<220> FEATURE:
<221> NAME/KEY: MOD_RES
<222> LOCATION: (35)..(35)
<223> OTHER INFORMATION: Arg, Ala, Cys or Ile
<220> FEATURE:
<221> NAME/KEY: MOD_RES
<222> LOCATION: (39)..(39)
<223> OTHER INFORMATION: Val, Asp, Arg or Lys
<220> FEATURE:
<221> NAME/KEY: MOD_RES
<222> LOCATION: (48)..(48)
<223> OTHER INFORMATION: Ala or Leu
<220> FEATURE:
<221> NAME/KEY: MOD_RES
<222> LOCATION: (51)..(51)
<223> OTHER INFORMATION: Thr, Tyr, Asn or Asp
<220> FEATURE:
<221> NAME/KEY: MOD_RES
<222> LOCATION: (53)..(53)
<223> OTHER INFORMATION: Arg, Tyr or Lys
<220> FEATURE:
<221> NAME/KEY: MOD_RES
<222> LOCATION: (59)..(59)
<223> OTHER INFORMATION: Ala, Ile, Gln, Val or Phe
<220> FEATURE:
<221> NAME/KEY: MOD_RES
<222> LOCATION: (60)..(60)
<223> OTHER INFORMATION: Val, Ala or Ile
<220> FEATURE:
<221> NAME/KEY: MOD_RES
<222> LOCATION: (73)..(73)
<223> OTHER INFORMATION: Val, Lys, Arg, Asp or Gln
<220> FEATURE:
<221> NAME/KEY: MOD_RES
<222> LOCATION: (75)..(75)
<223> OTHER INFORMATION: Arg, Gly, Glu or Pro
<220> FEATURE:
<221> NAME/KEY: MOD_RES
<222> LOCATION: (76)..(76)
<223> OTHER INFORMATION: Pro, Ala, Lys or Gly
<220> FEATURE:
<221> NAME/KEY: MOD_RES
<222> LOCATION: (78)..(78)
<223> OTHER INFORMATION: Arg, Thr, Val or Ile
<220> FEATURE:
<221> NAME/KEY: MOD_RES
<222> LOCATION: (80)..(80)
<223> OTHER INFORMATION: Val, Lys, Ser or Arg
<220> FEATURE:
<221> NAME/KEY: MOD_RES
<222> LOCATION: (83)..(83)
<223> OTHER INFORMATION: Lys, Glu, Pro or Ala
<220> FEATURE:
<221> NAME/KEY: MOD_RES
```

```
<222> LOCATION: (91)..(91)
<223> OTHER INFORMATION: Glu, Ala or Gln
<220> FEATURE:
<221> NAME/KEY: MOD_RES
<222> LOCATION: (95)..(95)
<223> OTHER INFORMATION: Thr, Gln, Arg, Val or Glu
<220> FEATURE:
<221> NAME/KEY: MOD_RES
<222> LOCATION: (96)..(96)
<223> OTHER INFORMATION: Arg, Val or Lys
<220> FEATURE:
<221> NAME/KEY: MOD_RES
<222> LOCATION: (104)..(104)
<223> OTHER INFORMATION: Thr, Ser, Asp or Tyr
<220> FEATURE:
<221> NAME/KEY: MOD_RES
<222> LOCATION: (108)..(108)
<223> OTHER INFORMATION: Asp or Glu
<220> FEATURE:
<221> NAME/KEY: MOD_RES
<222> LOCATION: (119)..(119)
<223> OTHER INFORMATION: Tyr, Leu, Met or Ala
<220> FEATURE:
<221> NAME/KEY: MOD_RES
<222> LOCATION: (123)..(123)
<223> OTHER INFORMATION: Met, Leu or Ile
<220> FEATURE:
<221> NAME/KEY: MOD_RES
<222> LOCATION: (134)..(134)
<223> OTHER INFORMATION: Lys, Thr or Glu
<220> FEATURE:
<221> NAME/KEY: MOD_RES
<222> LOCATION: (137)..(137)
<223> OTHER INFORMATION: His, Met, Tyr or Phe
<220> FEATURE:
<221> NAME/KEY: MOD_RES
<222> LOCATION: (147)..(147)
<223> OTHER INFORMATION: Ile, Asp, Glu or Leu
<220> FEATURE:
<221> NAME/KEY: MOD_RES
<222> LOCATION: (148)..(148)
<223> OTHER INFORMATION: Arg, Lys or His
<220> FEATURE:
<221> NAME/KEY: MOD_RES
<222> LOCATION: (151)..(151)
<223> OTHER INFORMATION: Asp, Gly or Asn
<220> FEATURE:
<221> NAME/KEY: MOD_RES
<222> LOCATION: (163)..(163)
<223> OTHER INFORMATION: Ala, His, Arg, Gln or Ile
<220> FEATURE:
<221> NAME/KEY: MOD_RES
<222> LOCATION: (165)..(165)
<223> OTHER INFORMATION: Glu, Thr, Ala, His or Leu
<220> FEATURE:
<221> NAME/KEY: MOD_RES
<222> LOCATION: (166)..(166)
<223> OTHER INFORMATION: Val, Gln, Gly, Ile or Thr
<220> FEATURE:
<221> NAME/KEY: MOD_RES
<222> LOCATION: (168)..(168)
<223> OTHER INFORMATION: Asp, Glu or Gln
<220> FEATURE:
<221> NAME/KEY: MOD_RES
<222> LOCATION: (172)..(172)
<223> OTHER INFORMATION: Ala, Leu, Arg, Val or Thr
<220> FEATURE:
<221> NAME/KEY: MOD_RES
<222> LOCATION: (174)..(174)
<223> OTHER INFORMATION: Thr, Glu, Val, Asn or Ser
<220> FEATURE:
<221> NAME/KEY: MOD_RES
<222> LOCATION: (178)..(178)
<223> OTHER INFORMATION: Asp or Thr
<220> FEATURE:
<221> NAME/KEY: MOD_RES
<222> LOCATION: (181)..(181)
<223> OTHER INFORMATION: Ala, Asp, Glu, Lys or Tyr
<220> FEATURE:
<221> NAME/KEY: MOD_RES
```

```
<222> LOCATION: (182)..(182)
<223> OTHER INFORMATION: Tyr or Gly
<220> FEATURE:
<221> NAME/KEY: MOD_RES
<222> LOCATION: (183)..(183)
<223> OTHER INFORMATION: Arg, Leu, Thr or Ile
<220> FEATURE:
<221> NAME/KEY: MOD_RES
<222> LOCATION: (187)..(187)
<223> OTHER INFORMATION: Ile, Val, Leu or Pro
<220> FEATURE:
<221> NAME/KEY: MOD_RES
<222> LOCATION: (190)..(190)
<223> OTHER INFORMATION: Gly, Thr, Asp, Trp or His
<220> FEATURE:
<221> NAME/KEY: MOD_RES
<222> LOCATION: (191)..(191)
<223> OTHER INFORMATION: Ser, Thr, Val or Gln
<220> FEATURE:
<221> NAME/KEY: MOD_RES
<222> LOCATION: (192)..(192)
<223> OTHER INFORMATION: Pro, Gln, Arg, Asp or Tyr
<220> FEATURE:
<221> NAME/KEY: MOD_RES
<222> LOCATION: (197)..(197)
<223> OTHER INFORMATION: Gly, Asp, Asn, Lys or Glu
<220> FEATURE:
<221> NAME/KEY: MOD_RES
<222> LOCATION: (198)..(198)
<223> OTHER INFORMATION: Thr, Ala, Gly, Asp or Asn
<220> FEATURE:
<221> NAME/KEY: MOD_RES
<222> LOCATION: (200)..(200)
<223> OTHER INFORMATION: His, Gln, Lys, Val or Arg
<220> FEATURE:
<221> NAME/KEY: MOD_RES
<222> LOCATION: (203)..(203)
<223> OTHER INFORMATION: Trp, Leu, Gly or Phe
<220> FEATURE:
<221> NAME/KEY: MOD_RES
<222> LOCATION: (204)..(204)
<223> OTHER INFORMATION: Leu, Tyr or Val
<220> FEATURE:
<221> NAME/KEY: MOD_RES
<222> LOCATION: (209)..(209)
<223> OTHER INFORMATION: Pro, Arg, Val or Lys
<220> FEATURE:
<221> NAME/KEY: MOD_RES
<222> LOCATION: (211)..(211)
<223> OTHER INFORMATION: Thr, Asn, Arg or Ser
<220> FEATURE:
<221> NAME/KEY: MOD_RES
<222> LOCATION: (214)..(214)
<223> OTHER INFORMATION: Pro, Asn, Ser or Trp
<220> FEATURE:
<221> NAME/KEY: MOD_RES
<222> LOCATION: (215)..(215)
<223> OTHER INFORMATION: Tyr, His, Trp or Ala
<220> FEATURE:
<221> NAME/KEY: MOD_RES
<222> LOCATION: (216)..(216)
<223> OTHER INFORMATION: Trp, Cys, Gly or Ile
<220> FEATURE:
<221> NAME/KEY: MOD_RES
<222> LOCATION: (218)..(218)
<223> OTHER INFORMATION: Gly, Phe, Glu, Ala or Gln
<220> FEATURE:
<221> NAME/KEY: MOD_RES
<222> LOCATION: (221)..(221)
<223> OTHER INFORMATION: Gly or Pro
<220> FEATURE:
<221> NAME/KEY: MOD_RES
<222> LOCATION: (224)..(224)
<223> OTHER INFORMATION: Tyr, Ile, Glu, Lys or His
<220> FEATURE:
<221> NAME/KEY: MOD_RES
<222> LOCATION: (225)..(225)
<223> OTHER INFORMATION: Thr, Ala, Ser, His or Leu
<220> FEATURE:
<221> NAME/KEY: MOD_RES
```

```
<222> LOCATION: (227)..(227)
<223> OTHER INFORMATION: Ile, Ser, Thr, Val or Leu
<220> FEATURE:
<221> NAME/KEY: MOD_RES
<222> LOCATION: (233)..(233)
<223> OTHER INFORMATION: Gln, Glu or Asn
<220> FEATURE:
<221> NAME/KEY: MOD_RES
<222> LOCATION: (234)..(234)
<223> OTHER INFORMATION: Arg, Met, Asn, Ile or Leu
<220> FEATURE:
<221> NAME/KEY: MOD_RES
<222> LOCATION: (238)..(238)
<223> OTHER INFORMATION: Gly, Ser, Ala or Thr
<220> FEATURE:
<221> NAME/KEY: MOD_RES
<222> LOCATION: (239)..(239)
<223> OTHER INFORMATION: Asp, Trp, Ser, Lys or Tyr
<220> FEATURE:
<221> NAME/KEY: MOD_RES
<222> LOCATION: (242)..(242)
<223> OTHER INFORMATION: Leu, Met, Arg, Phe or Thr
<220> FEATURE:
<221> NAME/KEY: MOD_RES
<222> LOCATION: (251)..(251)
<223> OTHER INFORMATION: Asp, Glu, Phe, Ile or Leu
<220> FEATURE:
<221> NAME/KEY: MOD_RES
<222> LOCATION: (252)..(252)
<223> OTHER INFORMATION: Leu, Asn, Cys or Ser
<220> FEATURE:
<221> NAME/KEY: MOD_RES
<222> LOCATION: (253)..(253)
<223> OTHER INFORMATION: Gly, Arg, Thr, Ser or Asp
<220> FEATURE:
<221> NAME/KEY: MOD_RES
<222> LOCATION: (260)..(260)
<223> OTHER INFORMATION: Asp, Gln, Glu, Arg or Lys
<220> FEATURE:
<221> NAME/KEY: MOD_RES
<222> LOCATION: (262)..(262)
<223> OTHER INFORMATION: Thr, Lys, Met, Val or Phe
<220> FEATURE:
<221> NAME/KEY: MOD_RES
<222> LOCATION: (268)..(268)
<223> OTHER INFORMATION: Ala or Val
<220> FEATURE:
<221> NAME/KEY: MOD_RES
<222> LOCATION: (269)..(269)
<223> OTHER INFORMATION: Asp or Gly
<220> FEATURE:
<221> NAME/KEY: MOD_RES
<222> LOCATION: (270)..(270)
<223> OTHER INFORMATION: Ala or Leu
<220> FEATURE:
<221> NAME/KEY: MOD_RES
<222> LOCATION: (271)..(271)
<223> OTHER INFORMATION: Gly or His
<220> FEATURE:
<221> NAME/KEY: MOD_RES
<222> LOCATION: (275)..(275)
<223> OTHER INFORMATION: Gln, Thr, Ala or Val
<220> FEATURE:
<221> NAME/KEY: MOD_RES
<222> LOCATION: (280)..(280)
<223> OTHER INFORMATION: Glu, Phe, Ile, Gly or Thr
<220> FEATURE:
<221> NAME/KEY: MOD_RES
<222> LOCATION: (283)..(283)
<223> OTHER INFORMATION: Glu, Gln, Thr or His
<220> FEATURE:
<221> NAME/KEY: MOD_RES
<222> LOCATION: (284)..(284)
<223> OTHER INFORMATION: Pro, Val or Ala
<220> FEATURE:
<221> NAME/KEY: MOD_RES
<222> LOCATION: (289)..(289)
<223> OTHER INFORMATION: Trp, Asn, Leu, Ser or Tyr
<220> FEATURE:
<221> NAME/KEY: MOD_RES
```

```
<222> LOCATION: (290)..(290)
<223> OTHER INFORMATION: Glu, Arg or His
<220> FEATURE:
<221> NAME/KEY: MOD_RES
<222> LOCATION: (294)..(294)
<223> OTHER INFORMATION: Val, Ile or Thr
<220> FEATURE:
<221> NAME/KEY: MOD_RES
<222> LOCATION: (297)..(297)
<223> OTHER INFORMATION: Arg, Glu, Ser or Leu
<220> FEATURE:
<221> NAME/KEY: MOD_RES
<222> LOCATION: (298)..(298)
<223> OTHER INFORMATION: Ser, Asn, Arg or Asp
<220> FEATURE:
<221> NAME/KEY: MOD_RES
<222> LOCATION: (301)..(301)
<223> OTHER INFORMATION: Ala, Phe, Met, Val or Leu
<220> FEATURE:
<221> NAME/KEY: MOD_RES
<222> LOCATION: (304)..(304)
<223> OTHER INFORMATION: Leu, Met, Ala or Thr
<220> FEATURE:
<221> NAME/KEY: MOD_RES
<222> LOCATION: (305)..(305)
<223> OTHER INFORMATION: Gln, Gly, His, Glu or Cys
<220> FEATURE:
<221> NAME/KEY: MOD_RES
<222> LOCATION: (319)..(319)
<223> OTHER INFORMATION: Ile, Val, Met, Leu or Phe
<220> FEATURE:
<221> NAME/KEY: MOD_RES
<222> LOCATION: (323)..(323)
<223> OTHER INFORMATION: Asn, Lys, Gly or His
<220> FEATURE:
<221> NAME/KEY: MOD_RES
<222> LOCATION: (324)..(324)
<223> OTHER INFORMATION: Phe, Cys, Val or Ile
<220> FEATURE:
<221> NAME/KEY: MOD_RES
<222> LOCATION: (330)..(330)
<223> OTHER INFORMATION: Arg, Gly, Asp, Asn or Ser
<220> FEATURE:
<221> NAME/KEY: MOD_RES
<222> LOCATION: (334)..(334)
<223> OTHER INFORMATION: Ser, Thr, Leu, Tyr or Val
<220> FEATURE:
<221> NAME/KEY: MOD_RES
<222> LOCATION: (337)..(337)
<223> OTHER INFORMATION: Ser, Gly, Ala or Thr
<220> FEATURE:
<221> NAME/KEY: MOD_RES
<222> LOCATION: (338)..(338)
<223> OTHER INFORMATION: Phe, Ser, Gln or His
<220> FEATURE:
<221> NAME/KEY: MOD_RES
<222> LOCATION: (341)..(341)
<223> OTHER INFORMATION: Phe, Met, Ala or Gly
<220> FEATURE:
<221> NAME/KEY: MOD_RES
<222> LOCATION: (343)..(342)
<223> OTHER INFORMATION: Val, Ile, Met, Thr or Phe
<220> FEATURE:
<221> NAME/KEY: MOD_RES
<222> LOCATION: (351)..(351)
<223> OTHER INFORMATION: Val, Ile or Leu
<220> FEATURE:
<221> NAME/KEY: MOD_RES
<222> LOCATION: (352)..(352)
<223> OTHER INFORMATION: Ser, Asp, Ile, Val or Lys
<220> FEATURE:
<221> NAME/KEY: MOD_RES
<222> LOCATION: (379)..(379)
<223> OTHER INFORMATION: Pro, Leu, Ile or Val
<220> FEATURE:
<221> NAME/KEY: MOD_RES
<222> LOCATION: (382)..(382)
<223> OTHER INFORMATION: Ser, Asn, Gln, His or Thr
<220> FEATURE:
<221> NAME/KEY: MOD_RES
```

-continued

```
<222> LOCATION: (394)..(394)
<223> OTHER INFORMATION: Ala, Phe, Tyr, Trp or Glu
<220> FEATURE:
<221> NAME/KEY: MOD_RES
<222> LOCATION: (398)..(398)
<223> OTHER INFORMATION: Gln, Ala or Trp
<220> FEATURE:
<221> NAME/KEY: MOD_RES
<222> LOCATION: (400)..(400)
<223> OTHER INFORMATION: Ala, Phe or Arg
<220> FEATURE:
<221> NAME/KEY: MOD_RES
<222> LOCATION: (404)..(404)
<223> OTHER INFORMATION: Glu, Asp or Thr
<220> FEATURE:
<221> NAME/KEY: MOD_RES
<222> LOCATION: (406)..(406)
<223> OTHER INFORMATION: Glu, Ala, Gln or Gly
<220> FEATURE:
<221> NAME/KEY: MOD_RES
<222> LOCATION: (411)..(411)
<223> OTHER INFORMATION: Arg, Ala, Glu or Lys
<220> FEATURE:
<221> NAME/KEY: MOD_RES
<222> LOCATION: (415)..(415)
<223> OTHER INFORMATION: Pro, Val, Arg, Leu or Thr
<220> FEATURE:
<221> NAME/KEY: MOD_RES
<222> LOCATION: (416)..(416)
<223> OTHER INFORMATION: Leu, Val, Phe or Ile
<220> FEATURE:
<221> NAME/KEY: MOD_RES
<222> LOCATION: (424)..(424)
<223> OTHER INFORMATION: Thr, Ala or Lys
<220> FEATURE:
<221> NAME/KEY: MOD_RES
<222> LOCATION: (425)..(425)
<223> OTHER INFORMATION: Ala, Lys, Val, Ile or Met
<220> FEATURE:
<221> NAME/KEY: MOD_RES
<222> LOCATION: (428)..(428)
<223> OTHER INFORMATION: Gly or Thr
<220> FEATURE:
<221> NAME/KEY: MOD_RES
<222> LOCATION: (433)..(433)
<223> OTHER INFORMATION: Asp, Glu, Val, Gly or Phe
<220> FEATURE:
<221> NAME/KEY: MOD_RES
<222> LOCATION: (435)..(435)
<223> OTHER INFORMATION: Thr, Arg, Ile or Ala
<220> FEATURE:
<221> NAME/KEY: MOD_RES
<222> LOCATION: (436)..(436)
<223> OTHER INFORMATION: Lys, Leu, Ile, Arg or Gln
<220> FEATURE:
<221> NAME/KEY: MOD_RES
<222> LOCATION: (438)..(438)
<223> OTHER INFORMATION: Leu, Ser, Asp, Ala or Lys
<220> FEATURE:
<221> NAME/KEY: MOD_RES
<222> LOCATION: (443)..(443)
<223> OTHER INFORMATION: Val, Glu or Ile
<220> FEATURE:
<221> NAME/KEY: MOD_RES
<222> LOCATION: (448)..(448)
<223> OTHER INFORMATION: Pro, Asp or Ala
<220> FEATURE:
<221> NAME/KEY: MOD_RES
<222> LOCATION: (453)..(453)
<223> OTHER INFORMATION: Gly, Ser, Ile or Ala
<220> FEATURE:
<221> NAME/KEY: MOD_RES
<222> LOCATION: (454)..(454)
<223> OTHER INFORMATION: Val, Leu, Asn or Gly
<220> FEATURE:
<221> NAME/KEY: MOD_RES
<222> LOCATION: (456)..(456)
<223> OTHER INFORMATION: Thr, Leu, Lys or Glu
<220> FEATURE:
<221> NAME/KEY: MOD_RES
```

```
<222> LOCATION: (457)..(457)
<223> OTHER INFORMATION: Gly, Lys, Asn, Ser or Ala
<220> FEATURE:
<221> NAME/KEY: MOD_RES
<222> LOCATION: (459)..(459)
<223> OTHER INFORMATION: Thr, Leu, Asp, Phe or Tyr
<220> FEATURE:
<221> NAME/KEY: MOD_RES
<222> LOCATION: (466)..(466)
<223> OTHER INFORMATION: Ala, Trp or Cys
<220> FEATURE:
<221> NAME/KEY: MOD_RES
<222> LOCATION: (479)..(479)
<223> OTHER INFORMATION: Asn, Arg or Ser
<220> FEATURE:
<221> NAME/KEY: MOD_RES
<222> LOCATION: (480)..(480)
<223> OTHER INFORMATION: Val, Thr, Asn or Cys
<220> FEATURE:
<221> NAME/KEY: MOD_RES
<222> LOCATION: (491)..(491)
<223> OTHER INFORMATION: Lys, Arg or Gly
<220> FEATURE:
<221> NAME/KEY: MOD_RES
<222> LOCATION: (501)..(501)
<223> OTHER INFORMATION: Asp, Tyr or Glu
<220> FEATURE:
<221> NAME/KEY: MOD_RES
<222> LOCATION: (502)..(502)
<223> OTHER INFORMATION: Gly, Lys or His
<220> FEATURE:
<221> NAME/KEY: MOD_RES
<222> LOCATION: (511)..(511)
<223> OTHER INFORMATION: Ser, Ala, Glu or Cys
<220> FEATURE:
<221> NAME/KEY: MOD_RES
<222> LOCATION: (512)..(512)
<223> OTHER INFORMATION: Ala, Asp or Gly
<220> FEATURE:
<221> NAME/KEY: MOD_RES
<222> LOCATION: (538)..(538)
<223> OTHER INFORMATION: Cys, Leu or Asn
<220> FEATURE:
<221> NAME/KEY: MOD_RES
<222> LOCATION: (539)..(539)
<223> OTHER INFORMATION: Ala, Thr or Ser
<220> FEATURE:
<221> NAME/KEY: MOD_RES
<222> LOCATION: (540)..(540)
<223> OTHER INFORMATION: Tyr, Asn or Ser
<220> FEATURE:
<221> NAME/KEY: MOD_RES
<222> LOCATION: (541)..(541)
<223> OTHER INFORMATION: Asn, Met or Ile
<220> FEATURE:
<221> NAME/KEY: MOD_RES
<222> LOCATION: (542)..(542)
<223> OTHER INFORMATION: Gly, Phe or Tyr
<220> FEATURE:
<221> NAME/KEY: MOD_RES
<222> LOCATION: (544)..(544)
<223> OTHER INFORMATION: Pro, Cys or Phe
<220> FEATURE:
<221> NAME/KEY: MOD_RES
<222> LOCATION: (546)..(546)
<223> OTHER INFORMATION: Gly, Glu, His or Asn
<220> FEATURE:
<221> NAME/KEY: MOD_RES
<222> LOCATION: (552)..(552)
<223> OTHER INFORMATION: Glu, Asp, His or Tyr
<220> FEATURE:
<221> NAME/KEY: MOD_RES
<222> LOCATION: (557)..(557)
<223> OTHER INFORMATION: Val, Glu, Ile, Asn or Thr
<220> FEATURE:
<221> NAME/KEY: MOD_RES
<222> LOCATION: (559)..(559)
<223> OTHER INFORMATION: Asp, Lys or Glu
<220> FEATURE:
<221> NAME/KEY: MOD_RES
```

```
<222> LOCATION: (560)..(560)
<223> OTHER INFORMATION: Pro, Gly, Asp or Gln
<220> FEATURE:
<221> NAME/KEY: MOD_RES
<222> LOCATION: (561)..(561)
<223> OTHER INFORMATION: Ala, Glu, Gln or Lys
<220> FEATURE:
<221> NAME/KEY: MOD_RES
<222> LOCATION: (562)..(562)
<223> OTHER INFORMATION: Thr, Val, Arg, Gln or Tyr
<220> FEATURE:
<221> NAME/KEY: MOD_RES
<222> LOCATION: (564)..(564)
<223> OTHER INFORMATION: Tyr, Lys or Val
<220> FEATURE:
<221> NAME/KEY: MOD_RES
<222> LOCATION: (581)..(581)
<223> OTHER INFORMATION: Asp, Arg or His
<220> FEATURE:
<221> NAME/KEY: MOD_RES
<222> LOCATION: (587)..(587)
<223> OTHER INFORMATION: Val, Ala or Ile
<220> FEATURE:
<221> NAME/KEY: MOD_RES
<222> LOCATION: (597)..(597)
<223> OTHER INFORMATION: Ala, Met, Leu, Ile or Thr
<220> FEATURE:
<221> NAME/KEY: MOD_RES
<222> LOCATION: (604)..(604)
<223> OTHER INFORMATION: Arg, Tyr, Val, Lys or Ile
<220> FEATURE:
<221> NAME/KEY: MOD_RES
<222> LOCATION: (606)..(606)
<223> OTHER INFORMATION: Leu, Thr, Asn or Asp
<220> FEATURE:
<221> NAME/KEY: MOD_RES
<222> LOCATION: (614)..(614)
<223> OTHER INFORMATION: Tyr, Gly or Trp
<220> FEATURE:
<221> NAME/KEY: MOD_RES
<222> LOCATION: (618)..(618)
<223> OTHER INFORMATION: Leu, Phe, Val, Arg or Gly
<220> FEATURE:
<221> NAME/KEY: MOD_RES
<222> LOCATION: (620)..(620)
<223> OTHER INFORMATION: Val, Gln, Tyr, Leu or Thr
<220> FEATURE:
<221> NAME/KEY: MOD_RES
<222> LOCATION: (626)..(626)
<223> OTHER INFORMATION: Gly, Glu, Lys, Asn or Ser
<220> FEATURE:
<221> NAME/KEY: MOD_RES
<222> LOCATION: (639)..(639)
<223> OTHER INFORMATION: Asn, Leu or Pro
<220> FEATURE:
<221> NAME/KEY: MOD_RES
<222> LOCATION: (643)..(643)
<223> OTHER INFORMATION: Val or Ile
<220> FEATURE:
<221> NAME/KEY: MOD_RES
<222> LOCATION: (644)..(644)
<223> OTHER INFORMATION: Thr or Lys

<400> SEQUENCE: 9

Met Ala His Gly Cys Ser Gly Gly Ala Met Lys Thr Xaa Leu Xaa Ile
1               5                   10                  15

Xaa Leu Ala Leu Xaa Leu Xaa Leu Xaa Ala Xaa Xaa Xaa Ala Ala Ala
            20                  25                  30

Ala Val Xaa Ala Gln Glu Xaa Val Val Asp Val Ser Asp Phe Gly Xaa
        35                  40                  45

Lys Pro Xaa Ser Xaa Lys Asn Ala Val Pro Xaa Xaa Gln Ala Ala Ile
    50                  55                  60

Asp Lys Ile Lys Ala Glu Cys Lys Xaa Gly Xaa Xaa Val Xaa Leu Xaa
65                  70                  75                  80
```

-continued

```
Phe Pro Xaa Gly Arg Tyr Asp Phe Trp Pro Xaa Gly Ala Thr Xaa Xaa
                85                  90                  95

Glu Tyr Tyr Ile Ser Asn Thr Xaa Thr Glu Gln Xaa Cys Pro Asp Asn
            100                 105                 110

Pro Lys Lys Val Gly Leu Xaa Leu Glu Asp Xaa Lys Asp Leu Thr Ile
        115                 120                 125

Asp Gly Asn Gly Ser Xaa Leu Val Xaa His Gly Arg Met Thr Pro Phe
    130                 135                 140

Ala Leu Xaa Xaa Cys Glu Xaa Val Val Leu Lys Asn Phe Ser Ile Asp
145                 150                 155                 160

Phe Glu Xaa Pro Xaa Xaa Ala Xaa Val Gln Val Xaa Glu Xaa Gly Val
                165                 170                 175

Thr Xaa Gly Glu Xaa Xaa Xaa Glu Val Glu Xaa His Pro Xaa Xaa Xaa
            180                 185                 190

Tyr Arg Ile Val Xaa Xaa Ser Xaa Ile Glu Xaa Xaa Gly Glu Gly Trp
        195                 200                 205

Xaa Ser Xaa Gly Tyr Xaa Xaa Xaa Ile Xaa Phe Asp Xaa Asp Thr Xaa
    210                 215                 220

Xaa Val Xaa Tyr Asn Thr Gly Asp Xaa Xaa Thr Trp Arg Xaa Xaa Asp
225                 230                 235                 240

Ala Xaa Glu Ile Ala Pro Gly Ile Val Arg Xaa Xaa Xaa Pro Lys Trp
                245                 250                 255

Lys Asp Ala Xaa Phe Xaa Pro Lys Ala Gly Pro Xaa Xaa Xaa Xaa Thr
            260                 265                 270

Val Leu Xaa Met Arg Asp Ile Xaa Arg Asp Xaa Xaa Gly Ile Phe Ile
        275                 280                 285

Xaa Xaa Ser Lys Asn Xaa Thr Leu Xaa Xaa Val Lys Xaa His Tyr Xaa
    290                 295                 300

Xaa Gly Leu Gly Ile Val Ser Gln Tyr Ser Glu Asn Ile Thr Xaa Asp
305                 310                 315                 320

Arg Val Xaa Xaa Ala Pro Arg Gly Pro Xaa Ser Gly Arg Xaa Leu Ala
                325                 330                 335

Xaa Xaa Ala Asp Xaa Xaa His Phe Ser Gly Cys Lys Gly Lys Xaa Xaa
            340                 345                 350

Ile Lys Asn Cys Leu Phe Ala Gly Ala Met Asp Asp Pro Ile Asn Val
        355                 360                 365

His Gly Thr Tyr Leu Arg Val Ile Glu Lys Xaa Asp Asp Xaa Thr Leu
    370                 375                 380

Lys Leu Arg Phe Met His Asp Gln Ser Xaa Gly Phe Glu Xaa Gly Xaa
385                 390                 395                 400

Pro Gly Asp Xaa Val Xaa Phe Val Arg Ser Xaa Thr Met Glu Xaa Xaa
                405                 410                 415

Ala Lys Ala Asn Gln Ile Thr Xaa Xaa Arg Pro Xaa Pro Tyr Asp Lys
            420                 425                 430

Xaa Glu Xaa Xaa Ser Xaa Arg Glu Phe Ser Xaa Thr Phe Asp Arg Xaa
        435                 440                 445

Ile Pro Pro Ala Xaa Xaa Glu Xaa Xaa Gly Xaa Val Ile Glu Asn Leu
    450                 455                 460

Thr Xaa Thr Pro Glu Val Glu Ile Arg Asn Asn Tyr Phe Arg Xaa Xaa
465                 470                 475                 480

Arg Thr Arg Gly Thr Leu Val Thr Thr Pro Xaa Lys Val Val Ile Glu
                485                 490                 495

Asn Asn Thr Phe Xaa Xaa Thr Ser Met Ser Ala Ile Leu Ile Xaa Xaa
            500                 505                 510
```

```
Asp Ala Asn Gly Trp Tyr Glu Ser Gly Pro Val Lys Asp Val Thr Ile
            515                 520                 525

Arg Gly Asn Thr Phe Ile Asn Pro Ala Xaa Xaa Xaa Xaa Gln Xaa
        530                 535                 540

Gly Xaa Ala Val Ile Ser Ile Xaa Pro Glu Asn Pro Xaa Ile Xaa Xaa
545                 550                 555                 560

Xaa Xaa Pro Xaa His His Asn Gly Lys Asp Gly Gly Ile Arg Ile Glu
            565                 570                 575

Asp Asn Thr Phe Xaa Thr Phe Asp Tyr Pro Xaa Leu Tyr Ala Lys Ser
            580                 585                 590

Val Asp Gly Leu Xaa Phe Arg Asn Asn Thr Ile Xaa Arg Xaa Thr Thr
            595                 600                 605

Phe Lys Pro Phe His Xaa Asn Lys Asp Xaa Phe Xaa Leu Glu Gly Cys
            610                 615                 620

Lys Xaa Val Val Ile Ser Glu Asn Val Phe Glu Gly Glu Thr Xaa Arg
625                 630                 635                 640

Gln Ser Xaa Xaa Thr Glu Asn Met Lys Arg Lys Asp Leu Lys Thr Thr
            645                 650                 655

Ile Lys Pro Phe Phe Lys Leu Lys Lys
            660                 665

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro or Ala
<220> FEATURE:
<221> NAME/KEY: MOD_RES
<222> LOCATION: (4)..(4)
<223> OTHER INFORMATION: Val or Ile
<220> FEATURE:
<221> NAME/KEY: MOD_RES
<222> LOCATION: (6)..(6)
<223> OTHER INFORMATION: Val or Ile

<400> SEQUENCE: 10

Asp Asp Xaa Xaa Asn Xaa His Gly Thr
1               5

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(6)
<223> OTHER INFORMATION: Tyr or Phe
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (10)..(12)
```

```
<223> OTHER INFORMATION: Any amino acid
<220> FEATURE:
<221> NAME/KEY: MOD_RES
<222> LOCATION: (14)..(14)
<223> OTHER INFORMATION: Leu or Val
<220> FEATURE:
<221> NAME/KEY: MOD_RES
<222> LOCATION: (15)..(15)
<223> OTHER INFORMATION: Leu or Thr
<220> FEATURE:
<221> NAME/KEY: MOD_RES
<222> LOCATION: (17)..(17)
<223> OTHER INFORMATION: Lys or Arg
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 11

Asp Xaa Xaa Xaa Trp Xaa Glu Xaa Gly Xaa Xaa Xaa Asp Xaa Xaa Ile
1               5                   10                  15

Xaa Xaa Asn Xaa Phe
            20

<210> SEQ ID NO 12
<211> LENGTH: 30
<212> TYPE: PRT
<213> ORGANISM: Streptomyces avermitilis

<400> SEQUENCE: 12

Thr Val Ile Asp Val Thr Asp Phe Gly Ala Asp Pro Ser Gly Lys Ala
1               5                   10                  15

Asp Ser Ala Ala Ala Val Ser Ala Ala Met Ala His Ala Lys
            20                  25                  30

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgaattccc atggctcacg gatgctccgg aggg                               34

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcctcgagaa gcttctagtc cgtgaccacg gaggtgttc                          39

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: MOD_RES
```

<222> LOCATION: (6)..(6)
<223> OTHER INFORMATION: Inosine
<220> FEATURE:
<221> NAME/KEY: MOD_RES
<222> LOCATION: (9)..(9)
<223> OTHER INFORMATION: Inosine
<220> FEATURE:
<221> NAME/KEY: MOD_RES
<222> LOCATION: (12)..(12)
<223> OTHER INFORMATION: Inosine
<220> FEATURE:
<221> NAME/KEY: MOD_RES
<222> LOCATION: (24)..(24)
<223> OTHER INFORMATION: Inosine

<400> SEQUENCE: 15
ttcggngtng tnkgkcagtw cagngagaa                                              29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: MOD_RES
<222> LOCATION: (3)..(3)
<223> OTHER INFORMATION: Inosine
<220> FEATURE:
<221> NAME/KEY: MOD_RES
<222> LOCATION: (6)..(6)
<223> OTHER INFORMATION: Inosine
<220> FEATURE:
<221> NAME/KEY: MOD_RES
<222> LOCATION: (9)..(9)
<223> OTHER INFORMATION: Inosine
<220> FEATURE:
<221> NAME/KEY: MOD_RES
<222> LOCATION: (12)..(12)
<223> OTHER INFORMATION: Inosine
<220> FEATURE:
<221> NAME/KEY: MOD_RES
<222> LOCATION: (15)..(15)
<223> OTHER INFORMATION: Inosine
<220> FEATURE:
<221> NAME/KEY: MOD_RES
<222> LOCATION: (18)..(18)
<223> OTHER INFORMATION: Inosine
<220> FEATURE:
<221> NAME/KEY: MOD_RES
<222> LOCATION: (21)..(21)
<223> OTHER INFORMATION: Inosine
<220> FEATURE:
<221> NAME/KEY: MOD_RES
<222> LOCATION: (24)..(24)
<223> OTHER INFORMATION: Inosine

<400> SEQUENCE: 16
gtnccntgna tnttnatngg ntcntcgtg                                              29

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atcgactcgg tcaccttcaa ggccgac                                                27

<210> SEQ ID NO 18
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aagacgctgt tggtgatgcg tacggtgc                                          28

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcgctcgaaa ttaaccctca ctaaagggga attcggtacc ctcgaggcgc                  50

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctcgagggta ccgaattccg gaa                                               23

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatcgcgcct cgagggtacc gaattccgga a                                      31

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgcttcggcg tccgttcggg ccag                                              24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccggtgcacc gcaacgtcct catc                                              24

<210> SEQ ID NO 24
<211> LENGTH: 46
<212> TYPE: DNA
<213> ORGANISM: Artificial Sequence
```

-continued

<220> FEATURE:
<223> OTHER INFORMATION: Description of Artificial Sequence: Synthetic
      primer

<400> SEQUENCE: 24
gcgggatccc gggatgggac gtgtttatga catttcccag tttggc                    46

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcctcgagaa gctttcactc tgaaatcttc acgtttgtca ctcg                      44

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
catggatccc aggcctccgg atg                                             23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gatccatccg gaggcctggg atc                                             23

<210> SEQ ID NO 28
<211> LENGTH: 727
<212> TYPE: PRT
<213> ORGANISM: Streptomyces griseoplanus

<400> SEQUENCE: 28

Met Gly Thr Ala Thr Ala Gln Pro Ala Leu Arg Pro Gln Thr Ser Thr
1               5                   10                  15

Val Ile Gly Gly Leu His Gly Ala Ala Val Leu Asp Asn Thr Gly Arg
            20                  25                  30

Thr Val Ile Asp Val Thr Asp Phe Gly Ala Asp Pro Ser Gly Lys Ala
        35                  40                  45

Asp Ser Ala Ala Ala Val Ser Ala Ala Met Ala His Ala Lys Thr Val
    50                  55                  60

Gly Gly Pro Thr Thr Leu His Phe Pro Thr Gly Thr Tyr His Ile Trp
65                  70                  75                  80

Pro Glu Arg Thr Pro Lys Arg Glu Leu Tyr Val Ser Asn Thr Val Gly
                85                  90                  95

Ser Asp Gln Ala Phe Arg Thr Lys Asn Ile Gly Ile Leu Val Glu Asp
            100                 105                 110

Met Arg Asp Val Val Val Asp Gly Gly Ser Arg Ile Val Asn His
        115                 120                 125

Gly Phe Gln Thr Val Phe Ala Ala Ile Arg Ser Ser Asp Val Arg Phe

```
            130                 135                 140
Thr Asn Phe Ser Gln Thr Trp Val Ala Pro Lys Thr Val Asp Ile Thr
145                 150                 155                 160

Val Ala Asp Ala Gly Val Val Ser Gly Gln Ala Tyr Arg Ile Ile Asp
                165                 170                 175

Ile Pro Glu Thr Tyr Asp Tyr Ala Val Glu Gly Thr Ser Val Arg Trp
                180                 185                 190

Asn Gly Glu Arg Gly Pro Ala Thr Gly Gln Pro Tyr Trp Thr Gly Thr
                195                 200                 205

Asn Ser Phe Asp Tyr Ser Gln Val His Asp Pro Ala Thr Asn Arg Thr
210                 215                 220

Trp Arg Thr Ser Asn Pro Val Phe Pro Glu Arg His Glu Asp His Arg
225                 230                 235                 240

Pro Arg Arg Arg Gln Val Arg Ile Thr Tyr Gly Asp Ser Thr Ala Pro
                245                 250                 255

Gly Asp Arg Gly Tyr Val Tyr Gln Met Arg Glu Val Thr Arg Asp Thr
                260                 265                 270

Pro Gly Ala Leu Phe Trp Glu Ser Ser Arg Val Thr Val Asp His Leu
                275                 280                 285

Arg Leu Gly Tyr Leu His Gly Phe Gly Ile Val Gly Gln Leu Ser Glu
290                 295                 300

Asp Ile Gly Ile Asp Ser Val Thr Phe Lys Ala Asp Arg Gly Ser Gly
305                 310                 315                 320

Arg Val Thr Ser Gly Phe Ala Asp His Ile Gln Met Ser Gly Val Lys
                325                 330                 335

Gly Thr Val Arg Ile Thr Asn Ser Val Phe Asp Asn Pro Gln Asp Asp
                340                 345                 350

Pro Ile Asn Ile His Gly Thr Tyr Leu Gln Ala Thr Ala Ala Glu Arg
                355                 360                 365

Glu Thr Leu Gln Leu Arg Tyr Met His Asn Glu Thr Ser Gly Phe Pro
370                 375                 380

Gln Phe Tyr Pro Gly Asp Thr Ile Glu Leu Val Asp Lys Arg Thr Met
385                 390                 395                 400

Leu Ala Ala Pro Gly Ala Thr Ala Lys Val Val Ser Val Thr Gly Pro
                405                 410                 415

Thr Gly Ser Gly Val Pro Ala Gly Thr Asp Pro Asp Thr Tyr Leu Arg
                420                 425                 430

Thr Met Thr Val Val Leu Asp Arg Thr Leu Pro Ala Ala Val Leu Ala
                435                 440                 445

Ala Pro Gly Asp Tyr Val Ala Glu Asn Thr Thr Tyr Thr Pro Thr Val
450                 455                 460

Glu Ile Thr Gly Asn Thr Phe Gln Ala Val Pro Thr Arg Gly Ile Leu
465                 470                 475                 480

Val Thr Thr Arg Arg Pro Val Arg Ile Glu Asn Asn Arg Phe Asp Gly
                485                 490                 495

Met Ser Met Ala Ser Ile Tyr Ile Ser Ser Asp Ala Arg Ser Trp Tyr
                500                 505                 510

Glu Ser Gly Pro Val Arg Asn Val Thr Ile Arg Gly Asn Val Phe Asp
                515                 520                 525

Arg Pro Ala Ser Pro Val Ile Phe Phe Asp Pro Thr Asn Gln Asp Phe
                530                 535                 540

Val Ala Gly Gln Pro Val His Arg Asn Val Leu Ile Glu Asp Asn Asp
545                 550                 555                 560
```

```
Phe Asn Leu Thr Gly Gly Thr Ile Leu Ser Gly Arg Val Gly Gly
                565                 570                 575

Leu Thr Phe Arg Asp Asn Arg Val Glu Arg Tyr Pro His Leu Arg Leu
            580                 585                 590

Thr Gly Pro Ser Arg Ala Leu Arg Val Gly Asp Thr Thr Thr Val Thr
            595                 600                 605

Thr Asp Ala Pro Pro Pro Ser His Thr Ser Pro Leu Phe Thr Phe Asp
            610                 615                 620

Gly Ala Asp Asp Ile Thr Leu Ala Asn Asn Thr Tyr Gly Asn Gly Phe
625                 630                 635                 640

Asn Lys Arg Val Asn Thr Ala Asn Met Asp Val Ser Glu Ile Thr Val
                645                 650                 655

Thr Ala Asp Gly Leu Ala Leu Asn Ala Asp Ser Ile Ser Ser Ala Pro
                660                 665                 670

Val Ala Val Ser Tyr Ser Ser Ser Arg Pro Lys Val Ala Thr Val Asp
                675                 680                 685

Ser Glu Gly Val Val Lys Ala Leu Ser Gly Gly Thr Thr Ser Ile Thr
            690                 695                 700

Ala Arg Ala Thr Ile Gly Gly Val Arg Val Thr Ser Asn Pro Val Lys
705                 710                 715                 720

Val Val Val Ala Thr Glu Arg
                725

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 29

His His His His His His
1               5
```

METHOD OF PREPARING NON-HUMAN TISSUES FOR XENOTRANSPLANTATION USING α-GALACTOSIDASE

RELATED APPLICATIONS

This application is a National Stage application of PCT/US2006/042350, filed Oct. 31, 2006, which claims priority to U.S. Provisional Application No. 60/731,845, filed Oct. 31, 2005, and U.S. Provisional Application No. 60/836,000, filed Aug. 7, 2006. The entire contents of each of the aforementioned applications are incorporated herein by reference.

FIELD OF THE INVENTION

This invention relates to a novel family of polypeptides having α-galactosidase activities, demonstrating unique substrate specificities and superior kinetic properties, that are used for removal of the immunodominant monosaccharides on blood products and tissues. Specifically this invention provides a novel family of α3 glycosidases, used for the enzymatic removal of type B antigens from blood group B and AB reactive blood products, and the GaIili antigen from non-human animal tissues, thereby converting these to non-immunogenic cells and tissues suitable for transplantation.

BACKGROUND OF THE INVENTION

As used herein, the term "blood products" includes whole blood and cellular components derived from blood, including erythrocytes (red blood cells) and platelets.

There are more than thirty blood group (or type) systems, one of the most important of which is the ABO system. This system is based on the presence or absence of antigens A and/or B. These antigens are found on the surface of erythrocytes and platelets as well as on the surface of endothelial and most epithelial cells. The major blood product used for transfusion is erythrocytes, which are red blood cells containing hemoglobin, the principal function of which is the transport of oxygen. Blood of group A contains antigen A on its erythrocytes. Similarly, blood of group B contains antigen B on its erythrocytes. Blood of group AB contains both antigens, and blood of group O contains neither antigen.

The blood group structures are glycoproteins or glycolipids and considerable work has been done to identify the specific structures making up the A and B determinants or antigens. The ABH blood group specificity is determined by the nature and linkage of monosaccharides at the ends of the carbohydrate chains. The carbohydrate chains are attached to a peptide (glycoprotein) or lipid (glycosphingolipid) backbone, which are attached to the cell membrane of the cells. The immunodominant monosaccharide determining type A specificity is a terminal α1-3 linked N-acetylgalactosamine (GalNAc), while the corresponding monosaccharide of B type specificity is an α1-3 linked galactose (Gal). Type O cells lack either of these monosaccharides at the termini of oligosaccharide chains, which instead are terminated with α1-2 linked fucose (Fuc) residues.

A great diversity of blood group ABH carbohydrate structures are found due to structural variations in the oligosaccharide chains that carry ABH immunodominant saccharides. Table 1 lists structures reported in man and those that have been found on human red cells or in blood extracts. For a review, see, Clausen & Hakomori, Vox Sang 56(1): 1-20, 1989). Red cells contain ABH antigens on N-linked glycoproteins and glycosphingolipids, while it is generally believed that O-linked glycans on erythrocytes glycoproteins, mainly glycophorins, are terminated by sialic acid and not with ABH antigens. Type 1 chain glycosphingolipids are not endogenous products of red cells, but rather adsorbed from plasma.

TABLE I

Histo-Blood Group ABH Immunoreactive Determinants of Human Cells[1]

| Name | Hapten Structure | Type of Glycoconjugate | Found on RBC | No |
|---|---|---|---|---|
| A type 1, ALe[d] | GalNAcα1-3Galβ1-3GlcNAcβ1-R<br>2<br>Fucα1 | Glycolipid<br>N-linked<br>O-linked | Glycolipid | 1 |
| A type 1, ALe[b] | GalNAcα1-3Galβ1-3GlcNAcβ1-R<br>2    4<br>Fucα1  Fucα1 | Glycolipid<br>N-linked<br>O-linked | Glycolipid | 2 |
| A type 2, A | GalNAcα1-3Galβ1-4GlcNAcβ1-R<br>2<br>Fucα1 | Glycolipid<br>N-linked<br>O-linked | Glycolipid<br>N-linked | 3 |
| A type 2, ALe[y] | GalNAcα1-3Galβ1-4GlcNAcβ1-R<br>2    3<br>Fucα1  Fucα1 | Glycolipid<br>N-linked<br>O-linked | Glycolipid? | 4 |
| A type 3, O-linked | GalNAcα1-3Galβ1-3GalNAcα1-O-Ser/Thr<br>2<br>Fucα1 | O-linked | | 5 |
| A type 3, Repetitive | GalNAcα1-3Galβ1-3GalNAcα1-3Galβ1-4GlcNAcβ1-R<br>2             2<br>Fucα1         Fucα1 | Glycolipid | Glycolipid | 6 |
| A type 4, Globo | GalNAcα1-3Galβ1-3GalNAcβ1-3Galα1-R<br>2<br>Fucα1 | Glycolipid | Glycolipid? | 7 |

TABLE I-continued

Histo-Blood Group ABH Immunoreactive Determinants of Human Cells[1]

| Name | Hapten Structure | Type of Glycoconjugate | Found on RBC | No |
|---|---|---|---|---|
| A type 4, Ganglio | GalNAcα1-3Galβ1-3GalNAcβ1-3Galβ1-R<br>　　　　　　　2<br>　　　　　　Fucα1 | Glycolipid | | 8 |
| B type 1, BLe$^d$ | Galα1-3Galβ1-3GlcNAcβ1-R<br>　　　　　2<br>　　　Fucα1 | Glycolipid<br>N-linked<br>O-linked | Glycolipid | 9 |
| B type 1, BLe$^b$ | Galα1-3Galβ1-3GlcNAcβ1-R<br>　　　　　2　　　4<br>　　　Fucα1　　Fucα1 | Glycolipid<br>N-linked<br>O-linked | Glycolipid | 10 |
| B type 2, B | Galα1-3Galβ1-4GlcNAcβ1-R<br>　　　　　2<br>　　　Fucα1 | Glycolipid<br>N-linked<br>O-linked | Glycolipid<br>N-linked | 11 |
| B type 2, BLe$^y$ | Galα1-3Galβ1-4GlcNAcβ1-R<br>　　　　　2　　　3<br>　　　Fucα1　　Fucα1 | Glycolipid<br>N-linked<br>O-linked | Glycolipid? | 12 |
| B type 3, O-linked | Galα1-3Galβ1-3GalNAcα1-O-Ser/Thr<br>　　　　　2<br>　　　Fucα1 | O-linked | | 13 |
| B type 4, Globo | Galα1-3Galβ1-3GalNAcβ1-3Galα1-R<br>　　　　　2<br>　　　Fucα1 | Glycolipid? | Glycolipid? | 14 |
| B type 4, Ganglio | Galα1-3Galβ1-3GalNAcβ1-3Galβ1-R<br>　　　　　2<br>　　　Fucα1 | Glycolipid? | | 15 |
| H type 1, Le$^d$ | Galβ1-3GlcNAcβ1-R<br>　　2<br>Fucα1 | Glycolipid<br>N-linked<br>O-linked | Glycolipid | 16 |
| H type 1, Le$^b$ | Galβ1-3GlcNAcβ1-R<br>　　2　　　4<br>Fucα1　　Fucα1 | Glycolipid<br>N-linked<br>O-linked | Glycolipid | 17 |
| H type 2, H | Galβ1-4GlcNAcβ1-R<br>　　2<br>Fucα1 | Glycolipid<br>N-linked<br>O-linked | Glycolipid<br>N-linked | 18 |
| H type 2, Le$^y$ | Galβ1-4GlcNAcβ1-R<br>　　2　　　3<br>Fucα1　　Fucα1 | Glycolipid<br>N-linked<br>O-linked | Glycolipid? | 19 |
| H type 3, O-linked | Galβ1-3GalNAcβ1-O-Ser/Thr<br>　　2<br>Fucα1 | O-linked | | 20 |
| H type 3, H-A | Galβ1-3GalNAcβ1-3Galβ1-4GlcNAcβ1-R<br>　　2　　　　　　　　　　2<br>Fucα1　　　　　　　　Fucα1 | Glycolipid | Glycolipid<br>(A RBC) | 21 |
| H type 4, Globo | Galβ1-3GalNAcβ1-3Galα1-R<br>　　2<br>Fucα1 | Glycolipid | Glycolipid | 22 |
| H type 4, Ganglio | Galβ1-3GalNAcβ1-3Galβ1-R<br>　　2<br>Fucα1 | Glycolipid | | 23 |
| Thomsen-Friedenrich Tf, T | Galβ1-3GalNAcα1-O-Ser/Thr | O-linked | O-linked<br>(+SA) | 24 |

TABLE I-continued

Histo-Blood Group ABH Immunoreactive Determinants of Human Cells[1]

| Name | Hapten Structure | Type of Glycoconjugate | Found on RBC | No |
|---|---|---|---|---|
| Gal-A, T cross-react. | Galβ1-3GalNAcα1-3Galβ1-4GlcNAcβ1-R<br>    2<br>Fucα1 | Glycolipid | Glycolipid (A RBC) | 25 |
| Tn, A cross-react. | GalNAcα1-O-Ser/Thr | O-linked | O-linked (+SA) | 26 |

[1]Adapted from Clausen and Hakomori, Vox Sang 56(1): 1-20, 1989. Designations: "?" indicates potential glycolipid structures which have not been reported to date.

Blood group A and B exist in several subtypes. Blood group A subtypes are the most frequent, and there are three recognized major sub-types of blood type A. These sub-types are known as $A_1$, A intermediate ($A_{int}$) and $A_2$. There are both quantitative and qualitative differences that distinguish these three sub-types. Quantitatively, $A_1$ erythrocytes have more antigenic A sites, i.e., terminal N-acetylgalactosamine residues, than $A_{int}$ erythrocytes which in turn have more antigenic A sites than $A_2$ erythrocytes. Qualitatively, $A_1$ erythrocytes have a dual repeated A structure on a subset of glycosphingolipids, while $A_2$ cells have an H structure on an internal A structure on a similar subset of glycolipids (Clausen et al., Proc. Natl. Acad. Sci. USA 82(4): 1199-203, 1985, Clausen et al., J. Biol. Chem. 261(3): 1380-7, 1986). These differences between $A_1$ and weak A subtypes are thought to relate to differences in the kinetic properties of blood group A isoenzyme variants responsible for the formation of A antigens (Clausen et al., J. Biol. Chem. 261(3): 1388-92, 1986). The differences of group B subtypes are believed to be solely of quantitative nature.

Blood of group A contains antibodies to antigen B. Conversely, blood of group B contains antibodies to antigen A. Blood of group AB has neither antibody, and blood group O has both. Antibodies to these and other carbohydrate defined blood group antigens are believed to be elicited by continuous exposure to microbial organism carrying related carbohydrate structures. An individual whose blood contains either (or both) of the anti-A or anti-B antibodies cannot receive a transfusion of blood containing the corresponding incompatible antigen(s). If an individual receives a transfusion of blood of an incompatible group, the blood transfusion recipient's antibodies coat the red blood cells of the transfused incompatible group and cause the transfused red blood cells to agglutinate, or stick together. Transfusion reactions and/or hemolysis (the destruction of red blood cells) may result therefrom.

In order to avoid severe transfusion reactions due to the presence of antibodies to the A and B blood group antigens the blood group of the donor and the recipient are matched before blood transfusions by typing methods. For example, a blood type A recipient can be safely transfused with type A blood, which contains compatible antigens, but not type B blood, which would trigger an adverse immune response in the recipient. Because type O blood contains no A or B antigens, it can be transfused into any recipient with any blood type, i.e., recipients with blood types A, B, AB or O. Thus, type O blood is considered "universal", and may be used for all transfusions. Hence, it is desirable for blood banks to maintain large quantities of type O blood. However, there is a paucity of blood type O donors. Therefore, it is desirable and useful to remove the immunodominant A and B antigens on types A, B and AB blood in order to maintain large quantities of universal blood products.

In an attempt to increase the supply of type O blood, methods have been developed for converting type A, B and AB blood to type O blood. Although, enzymatic conversion of both group B and group A red cells have been achieved in the past, these older processes have several disadvantages, particularly that they require excessive quantities of enzyme, and the specificities of many glycan modifying enzymes are not restricted to cleavage of only the blood group A or B antigens.

As will be explained below, the present invention provides for a family of polypeptides having highly refined substrate specificities, and better kinetic properties, that can be used to generate tissues and blood products lacking immunodominant antigens, thereby providing an efficient and cost-effective commercial process to supply, e.g. universal (non-immunogenic) blood cells for transplant, and even animal tissues for xenotransplantation into humans.

Conversion of Blood Group B Cells:

Enzymatic conversion of type B blood using purified or recombinant Coffee bean (Coffea canephora) α-galactosidase has been achieved using 100-200 U/ml (U.S. Pat. No. 4,427,777; Zhu et al., Arch Biochem Biophys 1996; 327(2): 324-9; Kruskall et al., Transfusion 2000; 40(11): 1290-8). The specific activity of Coffee bean α-galactosidase was reported to be 32 U/mg using p-nitrophenyl α-D-Gal with one unit (U) defined as one μmole substrate hydrolyzed per minute (Zhu et al., Arch Biochem Biophys 1996; 327(2): 324-9). Enzymatic conversions were done at pH 5.5 with approximately 6 mg/ml enzyme at 80-90% hematocrit, and the resulting converted O cells functioned normally in transfusion experiments and no significant adverse clinical parameters were observed (Kruskall et al., Transfusion 2000; 40(11): 1290-8). This data along with earlier publications, clearly demonstrate that enzymatic conversion of red blood cells is feasible and that such enzyme group B converted O (B-ECO) cells can function as well as matched type untreated cells in transfusion medicine. Nevertheless, the quantities of enzymes required for seroconversion in these studies, even with recombinant production of the enzyme, renders this method for generating ECO cells impractical mainly for economical reasons.

Claims of protocols for improved conversion of B cells using recombinant *Glycine max* α-galactosidase with a specific activity of approximately 200 U/mg have been reported using 5-10 units of enzyme/ml blood (with 16% hematocrit) (see, U.S. Pat. Nos. 5,606,042; 5,633,130; 5,731,426; 6,184, 017). The *Glycine max* α-galactosidase was thus used at 25-50 μg/ml, which represents a significant reduction in enzyme protein quantities required (50-200 fold) (Davis et al., Biochemistry and Molecular Biology International, 39(3): 471-485, 1996). This reduction is partly due to the higher specific activity of the *Glycine max* α-galactosidase (approximately 6 fold) as well as different methods used for conversion and evaluation. The 200 U/ml enzyme used in the study of Kruskall et al., (Transfusion, 40(11): 1290-8, 2000) was worked out for full unit (approximately 220 ml packed cells) conversions at 80-90% hematocrits and thoroughly analyzed by standard blood bank typing as well as by more sensitive cross-match analysis. Furthermore, the efficiency of conversion was evaluated by analysis of survival and induced immunity in patients receiving multiple transfusions of converted cells. The enzymatic conversions were done in test tubes in ml scale at 16% hematocrit, as described in U.S. Pat. No. 5,606,042 (and U.S. Pat. Nos. 5,633,130; 5,731,426; 6,184,017) with *Glycine max* α-galactosidase, and the conversion efficiency not evaluated by cross-match analysis. Conversion of cells at 16% hematocrit required 10 U/ml, while conversions at 8% required 5 U/ml, indicating that converting at increased hematocrit requires more enzyme although higher cell concentrations were not tested. Thus, part of the reduction in enzyme protein quantities required compared to protocols reported by Kruskall et al., (Transfusion 2000; 40(11): 1290-8), is related to the concentration (hematocrit) of cells used in conversion, and this may represent more than 5-10 fold, although direct comparison is not possible without further experimentation. The U.S. Pat. No. 5,606,042 (and U.S. Pat. Nos. 5,633,130; 5,731,426; 6,184, 017) further provides improvements in the conversion buffer using Na citrate and glycine at less acidic pH (preferably pH 5.8) and including additional protein in the form of BSA (bovine serum albumin) for stabilization. Interestingly, the conversion buffer developed for the *Glycine max* α-galactosidase was found not to be applicable to Coffee bean α-galactosidase. Although, some improvement in the conversion of B cells may be provided by U.S. Pat. No. 5,606,042 (and U.S. Pat. Nos. 5,633,130; 5,731,426; 6,184,017), it is clear that at least more than 0.5 mg of enzyme is required per ml packed type B red cells using the disclosed protocol. It is likely that considerable more enzyme than this is required to obtain cells fully converted to O cells by the most sensitive typing procedures used in standard blood bank typing protocols. Furthermore, the protocol requires introduction of additional extraneous protein (BSA or human serum albumin) as well as exposing blood products to a significant acidic pH.

Bakunina et al. (Bakunina et al. Biochemistry (Moscow) 1998, p1420) has claimed the identification and isolation of a novel α-galactosidase from the marine bacterium *Pseudoalteromonas* spp. (KMM 701). The isolated enzyme preparation was purified to a specific activity of 9.8 U/mg using the substrate pNP-Gal and had an apparent molecular weight by gel filtration of 195 kD. The enzyme preparation efficiently cleaved the monosaccharide substrate pNP-Gal with an apparent Km for pNP-Gal of 0.29 mM as well as several unbranched disaccharides with terminal α-galactose including melibiose and Galα1-3Gal, and hence does not show high specificity for blood group B. This enzyme will therefore cleave unbranched oligosaccharides with terminal α-Gal such as the linear B structure as well as the $P_1$ antigen. The enzyme was reported to have a neutral pH optimum (i.e., a pH optimum ranging from about 6.5 to about 7.7) and to convert blood group B cells with 24 h incubation reaction time to cells typing as group O cells. However, details of the conversion procedure and enzyme consumption were not described, and the efficiency of conversion evaluated by standard typing procedures with licensed typing reagents remains to be tested. Purification to homogeneity, cloning and recombinant expression of the enzyme will likely be required to provide the quantities and quality of enzyme protein required for enzymatic conversion of red cells.

We have disclosed (U.S. Ser. No. 10/251,271) the identification and partial characterization of a novel α-galactosidase activity with high specific activity and highly restricted substrate specificity for the blood group B antigen. The enzyme activity was identified by screening more than 2,400 bacterial and fungal isolates and found in only a few bacteria. The enzyme was partly purified from cell lysates of *Streptomyces griseoplanus* strain #2357 (ATCC deposit No. PTA-4077) and partial amino acid sequence information was obtained.

It is evident from the above that further improvements in conversion of B cells is required in order to make this a practical and commercially applicable technology. Necessary improvements include obtaining more efficient and specific α-galactosidase enzymes, which allow conversion to take place preferable at neutral pH and without extraneous protein added.

Assays to Determine αGal Cleaving Glycosidase Activities:

Past methods for searching, identification and characterization of exo-glycosidases have generally relied on the use of simple monosaccharide derivatives as substrates to identify saccharide and potential linkage specificity. Derivatized monosaccharide, or rarely oligosaccharide, substrates include without limitation p-nitrophenyl (pNP), benzyl (Bz), 4-methyl-umbrelliferyl (Umb), and 7-amino-4-methyl-coumarin (AMC). The use of such substrates provides easy, fast, and inexpensive tools to identify glycosidase activities, and makes large scale screening of diverse sources of enzymes practically applicable. However, the kinetic properties and fine substrate specificities of glycosidase enzymes may not necessarily be reflected in assays with such simple structures. It is also possible that novel enzymes with high degree of specificity and/or selective efficiency for complex oligosaccharide and unique glycoconjugate structures exists, but that these may have been overlooked and remain unrecognized due to methods of analysis. Thus, in order to identify and select the optimal exo-glycosidase for a particular complex oligosaccharide or glycoconjugate structure it is preferable to use such complex structures in assays used for screening sources of enzymes. Furthermore, preferred assays used for screening include selection for preferable kinetic properties such as pH requirement and performance on substrates, e.g., attached to the membrane of cells.

In prior studies, all α-galactosidases (EC 3.2.1.22) and α-N-acetylgalactosaminidases (EC 3.2.1.49) used for removing the B and A antigens of blood cells had been identified and characterized using primarily p-nitrophenyl monosaccharide derivatives. Interestingly, most of these α-galactosidase and α-N-acetylgalactosaminidase enzymes used in past studies are evolutionary homologs as evidenced by significant DNA and amino acid sequence similarities. Thus, the human α-galactosidase and α-N-acetylgalactosaminidase are close homologs (Wang et al., J Biol Chem, 265: 21859-66,1990), and other enzymes previously used in blood cell conversion including the chicken liver α-N-acetylgalactosaminidase, fungal *acremonium* α-N-acetylgalactosaminidase, and bacterial α-galactosidases all exhibit significant sequence similarities. Sequence analysis of all known 0-glycoside hydrolases have been grouped in 85 distinct families based on sequence analysis, and the above mentioned α-galactosidases and α-N-acetylgalactosaminidases are grouped in family 27. These enzymes are characterized by having a retaining mechanism of catalysis and use aspartic acid as the catalytic nucleophile (Henrissat, Biochem Soc Trans, 26(2): 153-6, 1998; Rye & Withers, Curr Opin Chem Biol, 4(5): 573-80, 2000). The primary structure of a bacterial α-N-acetylgalactosaminidase from *Clostridium perfringens* was reported to be dissimilar and non-homologous to eukaryote α-N-acetyl-galactosaminidases (Calcutt et al. FEMS Micro Left 214:77-80, 2002), and is grouped in a distantly related glycosidase family 36, which also contains α-galactosidases and α-N-acetylgalactosaminidases. The catalytic mechanism of this group of enzymes is predicted to be similar to that of enzymes from family 27 because some sequence similarity exists between enzymes of the two families.

SUMMARY OF THE INVENTION

The present invention provides compositions and methods for the enzymatic removal of type B antigens from blood group B and AB reactive blood products. Specifically, this invention provides compositions and methods for the specific enzymatic removal of the immunodominant monosaccharides specifying the blood group B antigens, namely α1,3-D-galactose.

In one embodiment, this invention provides a novel family of homologous polypeptides, which have 20% or more overall amino acid sequence identity with SEQ NO. 2). These polypeptides exhibit α-galactosidase activity across a neutral pH optimum, and demonstrate high substrate specificity for blood group B or GaIiIIi antigen structures. and no or insignificant activity with αGal or αGalNAc-pNP monosaccharide substrates. Certain members of this family show no or insignificant activity with linear α1-3 linked Gal. Other polypeptides in this family will cleave linear structures, but show no or insignificant activity with P antigens and Galα1-4 linkages. The novel polypeptides and gene family disclosed by the present invention has applications for use in the removal of immunodominant monosaccharides, αGal and GaIiIIi, from complex oligosaccharide targets such as those close to the true A and B carbohydrate antigens of the surface of cells in blood products, and the GaIiIIi antigen from animal tissues.

In another aspect, this invention provides methods for the sero-conversion of all blood group AB and B red cells, resulting in the removal of immunodominant B antigens from type B and AB cells. The removal of B antigens can be determined, for example by standard blood bank serological typing. According to the methods of this invention, the B antigens are removed using the polypeptides described, that (i) have highly restricted specificity for blood group B antigens, (ii) have optimal performance at neutral pH with blood group oligosaccharides; and (iii) are active in red blood cell conversion at a slightly acidic to slightly basic, and preferably a neutral pH (pH from about 6 to about 8). These methods comprise the steps of: (a) contacting a blood product with one or more of these polypeptides, under approximately neutral pH conditions, for a period of time sufficient to remove the immunodominant B antigens, and (b) removing the polypeptide and digested antigen fragments from the seroconverted blood product.

In another embodiment, this invention provides methods for the removal of all detectable B antigens from group B or AB red cells, using α-galactosidases that (I) have highly restricted specificity for blood group B antigens; and (ii) are active in red blood cell conversion with blood group oligosaccharides, over an approximately neutral pH range (pH about 6 to about 8).

In another aspect of the present invention, there are provided sero-converted erythrocytes. In one embodiment, the sero-converted erythrocytes are characterized as: (i) having been converted from a type B or type AB erythrocyte to a non-B erythrocyte (having no detectable B antigens, as determined by standard blood bank serological typing) seroconverted using a polypeptide of the family described herein.

In yet another aspect, the invention includes a modified red blood cell comprising: a group B erythrocyte or a group AB erythrocyte that lacks immunodominant B epitopes but displays α1-4Gal epitopes, including the P1 and $P^k$ blood group antigens. In one embodiment, the blood cell substantially lacks immunodominant B epitopes as determined by serological typing or hemagglutination assays, and also lacks linear α1-3 linked Gal structures. In another embodiment, the blood cell substantially lacks immunodominant B epitopes as determined by serological typing or hemagglutination assays, but retains linear α1-3 linked Gal structures.

In yet another aspect, the invention includes a modified red blood cell prepared by the method comprising: obtaining a group B erythrocyte or a group AB erythrocyte, suspending the erythrocyte in a buffer solution having an approximately neutral pH (about pH 6 to about pH 8), and contacting the erythrocyte with an alpha galactosidase polypeptide thereby substantially cleaving from the erythrocyte the immunodominant B epitopes. In various embodiment, the enzyme used to process the erythrocyte includes at least 10 contiguous amino acids of the polypeptide (or the nucleotide sequence encoding same) as specified by: SEQ ID NO: 2, SEQ ID NO: 3, SEQ ID NO: 4, SEQ ID NO: 5, SEQ ID NO: 6, SEQ ID NO: 7, or SEQ ID NO: 8. In certain embodiments, the enzymatic processing of the erythrocyte is performed at from about pH 6.0 to about pH 8.0, preferably about pH 6.5 to about pH 7.5, or more preferably about pH 7.0 to about pH 7.5. In currently preferred embodiments, enzymatic processing of the erythrocyte is performed using 0.01-1000 μg of enzyme per ml blood cells, preferably 0.1-500 μg of enzyme per ml blood cells, more preferably 1-100 μg of enzyme per ml blood cells. Most preferably enzymatic processing of antigens from the erythrocyte preparation is accomplished using 1-10 μg enzyme/ml blood cells.

In yet another aspect, the invention includes a method of modifying a red blood cell, comprising: obtaining a group B or group AB erythrocyte, suspending it in a buffer solution having an approximately neutral pH, and contacting it with an enzyme having at least 10 contiguous amino acids of the polypeptide sequence specified as or encoded by: SEQ ID NO: 2, SEQ ID NO: 3, SEQ ID NO: 4, SEQ ID NO: 5, SEQ ID NO: 6, SEQ ID NO: 7, or SEQ ID NO: 8, thereby cleaving the immunodominant B epitopes on the group B or group AB erythrocyte as determined by serological typing or hemagglutination assays. In one embodiment, the blood cell substantially lacks immunodominant B epitopes as determined by serological typing or hemagglutination assays, and also lacks linear α1-3 linked Gal structures. In another embodiment, the blood cell substantially lacks immunodominant B epitopes as determined by serological typing or hemagglutination assays, but retains linear α1-3 linked Gal structures.

In yet another aspect, the invention includes a method of treating a subject, comprising: identifying a subject in need of type A, O or AB blood, the subject being seropositive for anti-B antibodies; obtaining a modified blood cell preparation of seroconverted B cells, or obtaining the same by the methods described herein, and; transfusing the modified blood cell preparation into the subject, wherein the subject does not immunologically reject the transfused blood cells.

In yet another aspect, the invention includes a purified polypeptide, the polypeptide having at least 10 contiguous amino acids of the sequences: SEQ ID NO: 2, SEQ ID NO: 3, SEQ ID NO: 4, SEQ ID NO: 5, SEQ ID NO: 6, SEQ ID NO: 7, or SEQ ID NO: 8, wherein the enzyme displays α3 galactosidase activity, and a neutral pH optima. In certain embodiments, the purified enzyme, comprises: a polypeptide having at least 10 amino acids of the following sequence numbered accordingly when aligned with SEQ ID. NO:2: M at residue 10; G at residue 47; G at residue 84; Y at residue 86; Y at residue 99; N at residue 102; K at residue 114; T at residue 127; G at residue 130; G at residue 132; G at residue 139; N at residue 156; D at residue 160; P at residue 164; G at residue 205; R at residue 277; R at residue 281; F at residue 287; G at residue 308; Q at residue 312; I at residue 317; R at residue 333; D at residue 340; G at residue 346; G at residue 349; G at residue 360; D at residue 363; D at residue 364; N at residue 367; H at residue 369; G at residue 370; T at residue 371; G at residue 396; E at residue 462; N at residue 463; T at residue 465; T at residue 467; P at residue 468; R at residue 483; G at residue 484; L at residue 486; T at residue 489; N at residue 498; I at residue 508; D at residue 513; W at residue 517; E at residue 519; G at residue 521; D at residue 525; I at residue 528; N at residue 531; F at residue 533; I at residue 549; P at residue 553; I at residue 573; A at residue 590; G at residue 595; N at residue 601; and, I at residue 629; where the polypeptide has at least 20% identity with SEQ ID NO: 2, and where the polypeptide also has α3 galactosidase activity. In one embodiment, the polypeptide demonstrates specificity for branched alpha galactose structures but not linear alpha galactose structures. In another embodiment, the polypeptide demonstrates specificity for linear alpha galactose structures but not α1-4 gal structures. In one embodiment, the purified enzyme comprises a polypeptide including nine contiguous amino acids having the sequence DD(P/A)(V/I)N(V/I)HGT (SEQ ID NO: 10). In another embodiment, the purified enzyme comprises a polypeptide including twenty-one contiguous amino acids having the sequence: DXXXW(Y/F)E(S/T)GXXXD(L/V)(L/T)I(K/R)XNXF, (SEQ ID NO: 11) where X can be any amino acid. In one embodiment, the purified enzyme includes functional equivalents thereof having α3 galactosidase activity. In certain embodiments, the polypeptide includes a truncated variant lacking a signal sequence.

In another aspect, the invention includes a method of producing a recombinant enzyme, comprising: obtaining a nucleic acid encoding: SEQ ID NO: 2, SEQ ID NO: 3, SEQ ID NO: 4, SEQ ID NO: 5, SEQ ID NO: 6, SEQ ID NO: 7, or SEQ ID NO: 8; expressing the nucleic acid in a cell transfected therewith; inducing expression of the nucleic acid encoding the enzyme; and purifying the expressed enzyme from the cell. In various embodiments, the invention includes a non-naturally occurring prokaryotic cell, comprising: an expression vector not found in a wild-type prokaryotic cell, the expression vector having a nucleic acid sequence encoding a polypeptide having the sequence specified by: SEQ ID NO: 2, SEQ ID NO: 3, SEQ ID NO: 4, SEQ ID NO: 5, SEQ ID NO: 6, SEQ ID NO: 7, or SEQ ID NO: 8. It will be appreciated that due to the degeneracy of the genetic code, the recombinant enzyme can be optimized for expression in the particular host organism, as is generally known to those skilled in the art.

In a currently preferred embodiment, the invention relates to a family of α-galactosidases, and more particularly to the use of these to catalyze the removal of substantially all of the immunodominant B antigens on B and AB erythrocytes. The most preferred α-galactosidases are those that are active at a neutral pH, and catalyze removal of the immunodominant B antigens on B and AB erythrocytes and not other lipid-linked straight-chain carbohydrate αGal epitopes such as, P1 antigen (Gal α1,4 Gal β1,4 GlcNAc β1,3 Gal β1,4 Glc β1 ceramide) and Pk antigen (Gal α1,4 Gal β1,4 Glc β1 ceramide, also known as globotriosylceramide (Gb3Cer)/CD77). Particular α-galactosidases from this family are described below as, SEQ ID NO: 2, SEQ ID NO: 3, SEQ ID NO: 4, SEQ ID NO: 5, SEQ ID NO: 6, SEQ ID NO: 7, SEQ ID NO: 8, the fragment SEQ ID NO: 1 and the consensus sequence of SEQ ID NO: 9.

In yet another aspect, this invention provides methods for the screening and selection of enzymes with the above described preferred unique characteristics and methods of purification and amino acid sequencing useful for cloning and expression of the genes encoding these enzymes. These methods provide for bacterial isolates producing such preferred enzymes. Such other applications and features of the invention will be apparent from the detailed description that follows.

In yet another aspect, this invention provides compositions and methods for the enzymatic removal of the immunodominant monosaccharides on tissues, such as a tissue for xenotransplantation. Specifically the present invention provides a novel family of α3-glycosidases (as described above), used for the enzymatic removal of the GaliIi antigen from non-human animal tissues, thereby converting these to non-immunogenic tissues suitable for transplantation. Examples of an α3-galactosidase include, but are not limited to, of any of SEQ ID NO: 2-9.

The method of preparing a tissue for xenotransplantation comprises obtaining a tissue from a non-human animal source, incubating the tissue with a polypeptide having α3-galactosidase activity thereby removing immunodominant α1-3 linked terminal galactose residues from the tissue, and isolating the tissue from the polypeptide and the enzymatically removed galactose, thereby rendering the tissue suitable for xenotransplantation into humans. In one embodiment, the tissue from a non-human animal source is porcine connective tissue. In another embodiment, the porcine connective tissue is a ligament.

In another embodiment, the tissue from a non-human animal source is an organ including liver, kidney, or heart. In yet another embodiment, the tissue from a non-human animal source is non-immunogenic injectable collagen; bone xenografts; soft tissue and proteoglycan-reduced soft tissue xenografts; xenograft heart valves; meniscal xenografts; and tissue matrices, wherein the tissues are α1,3-galactose-deficient tissues that have been modified using an α3-galactosidase. Examples of an α3-galactosidase include, but are not limited to, of any of SEQ ID NO: 2-9.

BRIEF DESCRIPTION OF THE DRAWINGS

FIG. 10 illustrates the alignment of the peptide obtained by Edman sequencing of HPLC fractionated trypsin digest of a novel *Streptomyces griseoplanus* α-galactosidase (SEQ ID NO: 1), with a hypothetical protein from *Streptomyces avermitilis* (GenBank access # BAC74979.1, GI:29610934, SEQ ID NO: 2). The amino acids in SEQ ID NO: 2 that correspond to those of SEQ ID NO: 1 are underlined. The alignment was obtained by blast analysis of the peptide using "search for short, nearly exact matches" against NCBI nr database [(Score=51.5 bits (114), Expect=3e-06; Identities=18/29 (62%), Positives=24/29 (82%), Gaps=0/29 (0%)]. The amino acid sequence is shown in a single-letter code. The identical residues are indicated by bold capital letters, similar residues by plain bold letters, and different residues by small letters.

FIG. 12 illustrates protein sequence alignment of the putative novel α-galactosidase from *Streptomyces avermitills* (SEQ ID NO: 2) with a number of the first protein hits of unknown functions by blasting SEQ ID NO: 2 against NCBI nr databases. The alignment was performed using CLUSTALW multiple alignment (NPS@: Network Protein Sequence Analysis, TIBS 2000: 25; 147-150, Combet C., Blanchet C., Geourjon C. and Deléage G.). Alignment data: Alignment length: 665; Identity (*): 59 is 8.87%; Strongly similar (:): 86 is 12.93%; Weakly similar (.): 42 is 6.32%; Different: 478 is 71.88%. The sequences are as follows: SA (625 residues SEQ ID NO: 2); BTα (568 residues SEQ ID NO: 3); BFα1 (605 residues SEQ ID NO: 4); BFα2 (605 residues SEQ ID NO: 5); BFβ1 (595 residues SEQ ID NO: 6); BFβ2 (595 residues SEQ ID NO: 7); BTβ (615 residues SEQ ID NO: 8). SEQ ID NO: 9 is a consensus sequence of the sequences SEQ ID NOs: 2-8. Designations: SA, BT and BF, the putative α-galactosidases from *Streptomyces avermitilis* MA-4680, *Bacteroides* thetaotaomicron VPI-5482 and *Bacteroides fragilis*, respectively; α and β: 2 different copies of α-galactosidases from *B. thetaotaomicron* VPI-5482; α1 and β1: 2 different copies of α-galactosidases from *B. fragilis* YCH46; α2 and β2: two different copies of α-galactosidases from *B. fragilis* NCTC 9343.

FIG. 14 illustrates a SDS-NuPAGE analysis of α-galactosidase (SEQ ID NO: 2) expressed in *E. coli* (Novex 4-12% Bis-Tris Gel with MOPS buffer, stained with Colloidal Blue Staining kit, Mark12 Unstained Standard, all Invitrogen products). The lystate from each culture was prepared similarly as described in FIG. 13 legend with an increased scale. An aliquot of the each whole lysate was centrifuged at 14,000 g for 5 min. at RT. The supernatant was removed. Twelve μL of whole lysate or supernatant was mixed with 4 μL of 4×LDS buffer, supplemented 10% (v/v) β-mecaptoethanol. The pellet was suspended in 1×LDS sample buffer, supplemented with 2.5% (v/v) β-mecaptoethanol, at a ratio of 16 μL sample buffer/12 μL of whole lysate. All samples were heated at 70° C. for 10 min for SDS-NuPAGE analysis. Designations: WL, whole lysate; Sup, supernatant; PT, pellet; U, sample prepared from un-induced culture; I, sample prepared from induced culture.

FIG. 15 illustrates Multiple ClustalW (BoxShade 3.21) protein sequence alignment of the putative novel α-galactosidase family to identify conserved regions for the design of degenerate primers. Identical residues and conserved substitutions are highlighted in black and dark gray. The aligned sequences are from S. avermitilis MA-4680 (SA SEQ ID NO:2), B. thetaiotaomicron VPI-5482 (BTalpha SEQ ID NO:3; BTbeta SEQ ID NO:8) and B. fragilis NCTC 9343 (BFalphal SEQ ID NO:4; BFbetal SEQ ID NO:6). The two sequences from B. fragilis YCH624, nearly identical to those from B. fragilis NCTC 9343, are not included. The conserved regions used to design a pair of degenerate primers to clone the partial α-galactosidase gene from S. griseoplanus 2357 are indicated with a forward arrow for forward primer and backward arrow for reverse primer.

FIG. 16 illustrates protein sequence of a S. griseoplanus α-galactosidase (SEQ ID NO:28) highlighting the regions corresponding to the primers used for cloning. The forward and reverse primers are colored dark and light gray respectively. Degenerate primers are underlined.

FIG. 20 illustrates the substrate specificity of Bacteroides fragilis α-galactosidases. Enzyme assays were carried out without enzyme (−) and with ~30 ng enzyme (+), ~1.0 mM substrate in 10 μL of 10 mM NaPO4, pH 6.8, 2.5 mM NaCl, supplemented with 0.25 mg/mL BSA. Reactions were monitored by TLC during incubation at 26° C. and the 2 hr time point is shown. Cleavages of the branched blood group B trisaccharide (B-tri) to the H disaccharide (H-di) by BFα2 (FragA) α-galactosidase, and all B structures by BFβ1 (FragB) α-galactosidase, were complete within 5-20 min (not shown), whereas no cleavage of other oligosaccharide substrates were detected after 2 hr incubation. The TLC plates were developed in chloroform/methanol/water (30/60/10, v/v/v) for 15 min and stained by heating with 0.05% Orcinol in 0.5M $H_2SO_4$.

DETAILED DESCRIPTION OF THE INVENTION

Figure 1:
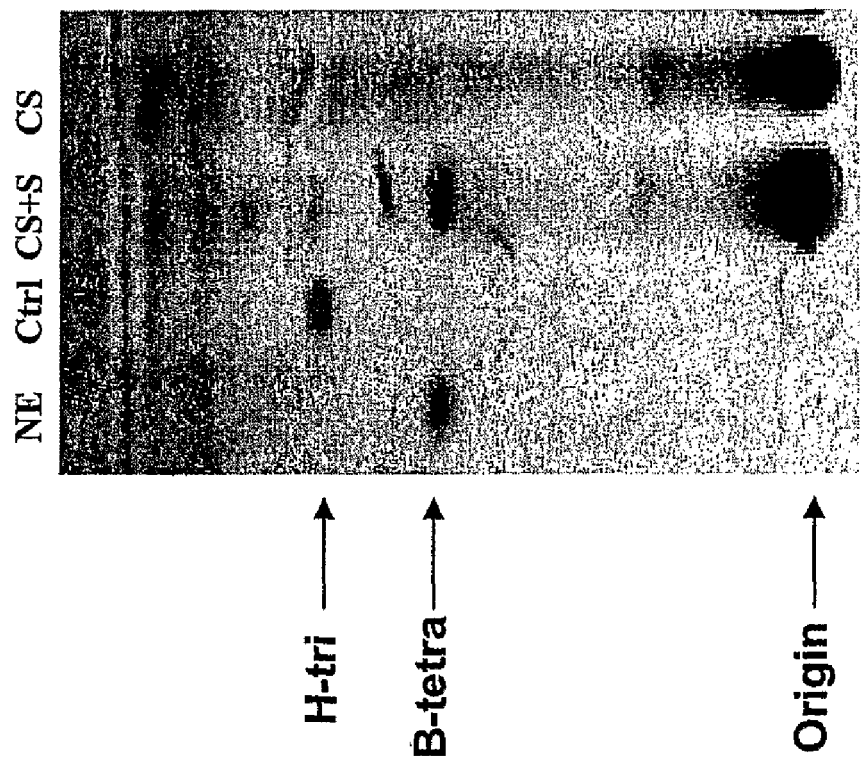
FIG. 1 illustrates HPTLC analysis of α-galactosidase activity in the culture supernatant of *Streptomyces griseoplanus* grown in rich media (See Table II for formulations) with the AMC labeled blood group B tetrasaccharide substrate. The fermentation was carried out in for 1 day in YM and 3 days in BP media, at 30° C., 220 rpm. Assays were performed by mixing equal volumes of the culture supernatant and 0.1 mM B-tetra in 100 mM NaPO4 (pH 6.8), and incubated at room temperature for 1 hr. One μL was sampled from each reaction and quickly applied onto HPTLC. Designations: NE, no enzyme control; Ctrl, positive control reaction by using Coffee bean α-galactosidase; CS, culture supernatant of *S. griseoplanus*; S, substrate, i.e., B tetrasaccharide; B-tetra, B tetrasaccharide; H-tri, H trisaccharide; Origin: the position in HPTLC where samples were applied. The TLC plate was developed in chloroform-methanol-water (vol/vol/vol: 60/35/8). The plate was scanned and photographed by a Bio-Rad Fluor-S MultiImager with Quantity One —4.1.1 software.

This invention is directed to the development and application of a screening and selection strategy for novel α-galactosidases with preferred specificities for the blood group B structures, and with preferred performance in the enzymatic conversion of blood products and animal tissues, over an approximately neutral pH range. Table 1 lists the complex structures of antigens found on blood cells.

For the purpose of this invention, blood group B active oligosaccharide derivatives were synthesized or produced by enzymatic removal of αGal from various substrates. Furthermore, glycosphingolipids with structures 3, 6, 21, and 25 were purified from human erythrocytes or produced therefrom by glycosidase treatments as previously described (Clausen et al., Proc. Natl. Acad. Sci. USA 82(4): 1199-203, 1985, Clausen et al., J Biol. Chem. 261(3): 1380-7, 1986, Clausen et al., Biochemistry 25(22): 7075-85,1986, Clausen et al., J Biol. Chem. 262(29): 14228-34,1987). Thin-layer chromatography assays to quantitatively determine removal of αGal or αGalNAc from the AMC derivatives or glycosphingolipids were developed.

Preferred α-galactosidases have high substrate specificity for blood group B branched saccharide structures, a generally neutral pH optima and can be produced cost-effectively as recombinant proteins in unicellular organisms such as bacteria and yeast. Our prior patent application (U.S. Ser. No. 10/251,271), developed a screening assay for the preferred enzyme activities using B tetrasaccharide AMC derivative substrates, and measured enzyme activities at neutral pH. Further, activities were compared to activities using p-nitrophenyl monosaccharide derivatives in order to identify activities with preference or exclusivity for the complex substrates. In that application, we disclose the use of this screening assay on a large panel of bacterial and fungal isolates (3100), and therein we identified several bacterial isolates expressing α-N-acetylgalactosaminidase or α-galactosidase activities measured with A or B tetrasaccharide AMC substrates, but no or insignificant levels of activity with the corresponding p-nitrophenyl monosaccharide substrates. One of each of these activities was further analyzed after sero- and genotyping these as Streptomyces strains. Analysis of strain #8 was determined to have α-N-acetylgalactosaminidase activity revealed that the activity was insoluble and was associated with the cell mass. Strain #8 was deposited on Feb. 14, 2002 with the American Type Culture Collection (ATCC) and has been assigned ATCC Deposit No. PTA-4076. In contrast, strain #2357 was determined to have α-galactosidase activity, and the activity was determined to be soluble, found in the supernatant of transformed cells lysed by French press. Strain #2357 was deposited on Feb. 14, 2002 with the American Type Culture Collection and was assigned ATCC Deposit No. PTA-4077. Because it is considerable simpler to purify a soluble protein, we chose to initially purify and sequence the protein from strain #2357.

The enzyme that we found in the soluble fraction of strain #2357 was partially purified. Detailed analysis of the substrate specificity of the partially purified α-galactosidase demonstrated an unprecedented fine specificity for the branched B blood group structures, but no linear structures capped by α1-3 or α1-4 galactose residues were cleaved by this enzyme. Analysis of its pH optimum showed the preferred conditions to be pH 5.5 to 7.0. The identified α-galactosidase activity is therefore highly preferred over enzymes known in the prior art due to its restricted substrate specificity, high specific activity for group B structures, and pH optimum. SDS-PAGE analysis of the resulting partially purified crude extract revealed 3-4 protein bands in the 40-80 kDa region having the α-galactosidase activity. Gel filtration analysis of the preparation showed the activity migrated comparable to BSA, indicating a globular protein having a molecular weight of about 40-80 kDa. A single short sequence was obtained:

```
Phe-Ala-Asn-Gly-Leu-Leu-Leu-Thr.    (SEQ ID NO: 1)
```

Subsequent to these studies, and as disclosed in the present invention, we have discovered a new family of polypeptides, having α-galactosidase activities, and have developed methods for their induction, purification, sequencing and cloning. As discussed below, the polypeptide family is distinct from the previously partially purified protein from strain #2357, and notably these family members do not contain the sequence shown as SEQ ID NO: 1. The new induction strategy involves growth of the appropriate bacterium on defined carbon sources and minimal medium, which results in a significant increase in production of the α-galactosidase polypeptides. Known α-galactosides (generally having an acidic pH optimum and substrate specificity for Galα-pNP or other simple monosaccharides) are not secreted in griseoplanus and related Streptomyces strains under the same growth conditions that produces these novel polypeptides.

The present invention therefore provides a novel method for the recombinant expression and purification of certain α-galactoside polypeptides. This purification strategy applied in combination with the novel growth and induction methods resulted in successful purification to apparent homogeneity of the α-galactosidase polypeptides in sufficient quantities for amino acid sequencing, and blood product and tissue conversions.

Figure 4:
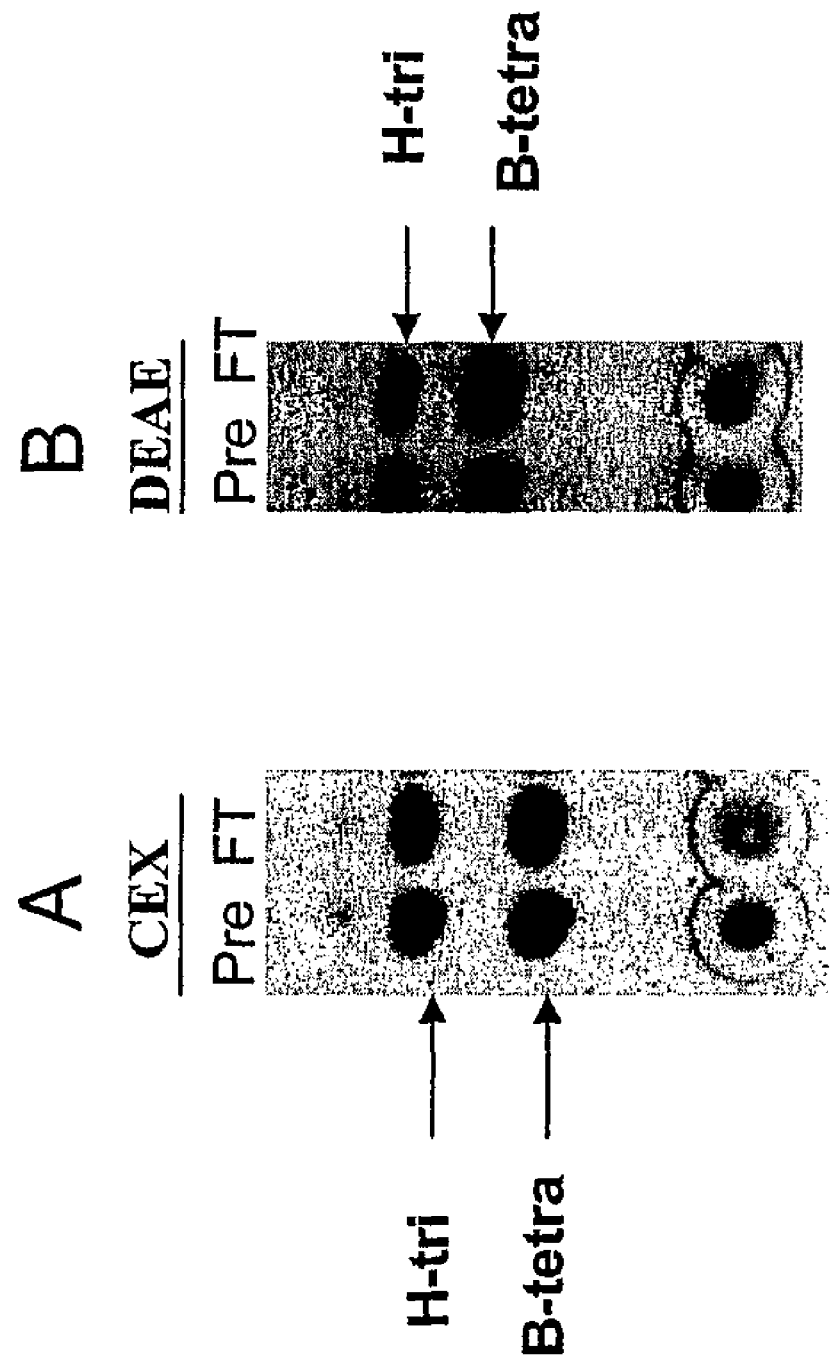
FIG. 4 illustrates an HPTLC analysis of the enzyme assay of α-galactosidase activity in the protein solution after passing CEX or DEAE column with B-tetra substrate. About 450 ml of *Streptomyces griseoplanus* supernatant, harvested from 800 mL of culture in an 1 liter fermenter fermentation grown in minimal media with galactose, stored frozen at −80° C., was thawed at for 24 hrs at 4° C. and centrifuged for 30 min at 4° C., 20,000 rpm. The recovered supernatant was passed through a 15 mL cation exchange chromatography column (CEX) (Macro-Prep High S Support, BioRad, Cat. #156-0031), pre-equilibrated with 40 mM NaPO4, 10 mM NaCl (pH 6.8). The flowthrough containing the enzyme activity was collected. The column was washed sequentially with 40 ml of equilibration buffer, 40 mL of the same buffer with a slightly increased pH (7.3). The flowthrough and washes were pooled and loaded directly onto a 2.5 mL DEAE column (DEAE Sepharose, Sigma, Cat. # DEF100) pre-equilibrated with CEX equilibration buffer and the flowthrough was collected. The column was washed with 50 ml of CEX equilibration buffer to remove the residual enzyme from the column. The pooled protein solution of DEAE flowthrough and wash (~600 mL) was concentrated using Centricon Plus 80 Centrifugal filter devices (Millipore Cat. #UFC5LGC02) and buffer-exchanged into 10 mM NaPO4 (pH 7.0) in the same device to a final volume of 23 mL.
Figure 6:
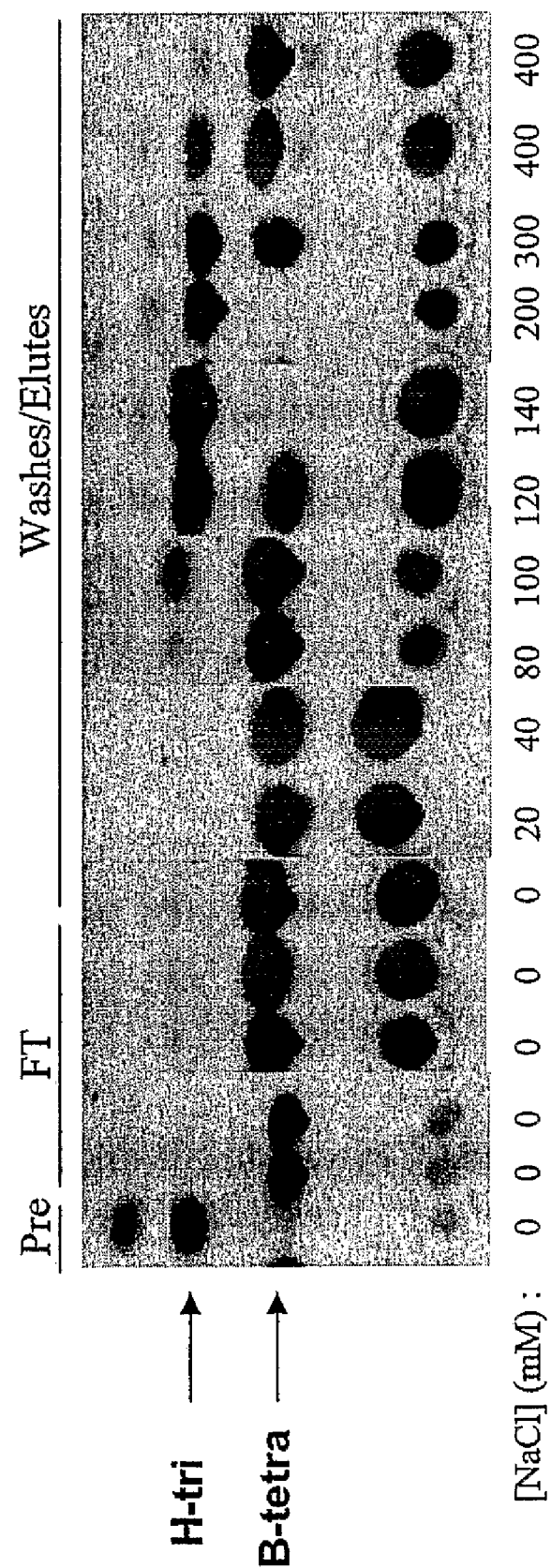
FIG. 6 illustrates HPTLC analysis result of α-galacotosidase activity in fractions from Cibacron Blue 3GA step with B-tetra substrate. The pooled activity fractions from Hydroxyapatite step was diluted 1:1 with H2O and applied onto a 2.5 mL of Cibacron Blue column (Cibacron Blue 3GA, Sigma, Cat. # C-1285), equilibrated with 10 mM Tris (pH 7.5). The column was washed with the equilibration buffer and further washed/eluted with equilibration buffer with increased amount of salt as indicated at the bottom of the panel. The enzyme activity was distributed between 100 and 400 mM NaCl washes. Designations: Pre, protein solution before being loaded onto the column; FT, flowthrough.
Figure 7:
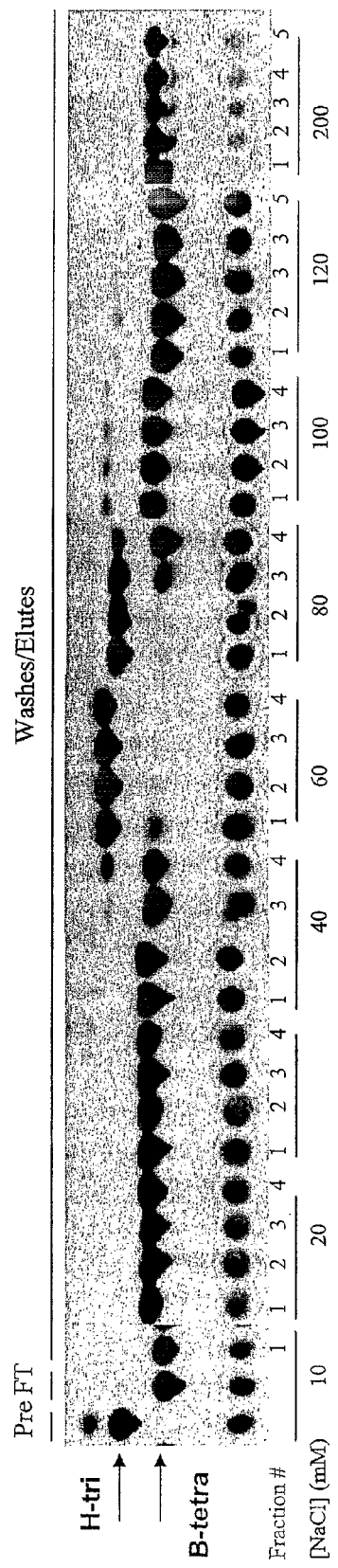
FIG. 7 illustrates HPTLC analysis of α-galacotosidase activity in various fractions from AEX step with B-tetra substrate. The pool of enzyme activity fractions from Cibacron Blue was concentrated and buffer-exchanged into 40 mM Tris, 10 mM NaCl (pH 8.5), to a final volume of 3.7 mL. The protein solution was loaded onto an 1 mL of AEX column (Macro-Prep High Q Support, Bio-Rad Cat. # 156-0051), pre-equilibrated with 40 mM Tris, 10 mM NaCl, pH 8.5. The column was first washed with equilibration buffer and then washed/eluted with the same buffer containing increasing amount of salt as indicated at the bottom of the panel. Designations: Pre, protein solution before being loaded onto the column; FT, flowthrough; Washes/Elutes, column wash and/or elution samples; [NaCl] (mM), the salt concentration in the wash/elution buffer; Fraction #, fractions collected in each wash/elution step; B-tetra, B tetrasaccharide, the substrate; H-tri, H trisaccharide, the product (the faster moving product above H-tri indicates the presence of contaminating fucosidase activity in the protein sample that cause further degradation of H trisaccharide into disacchamide).
Figure 8:
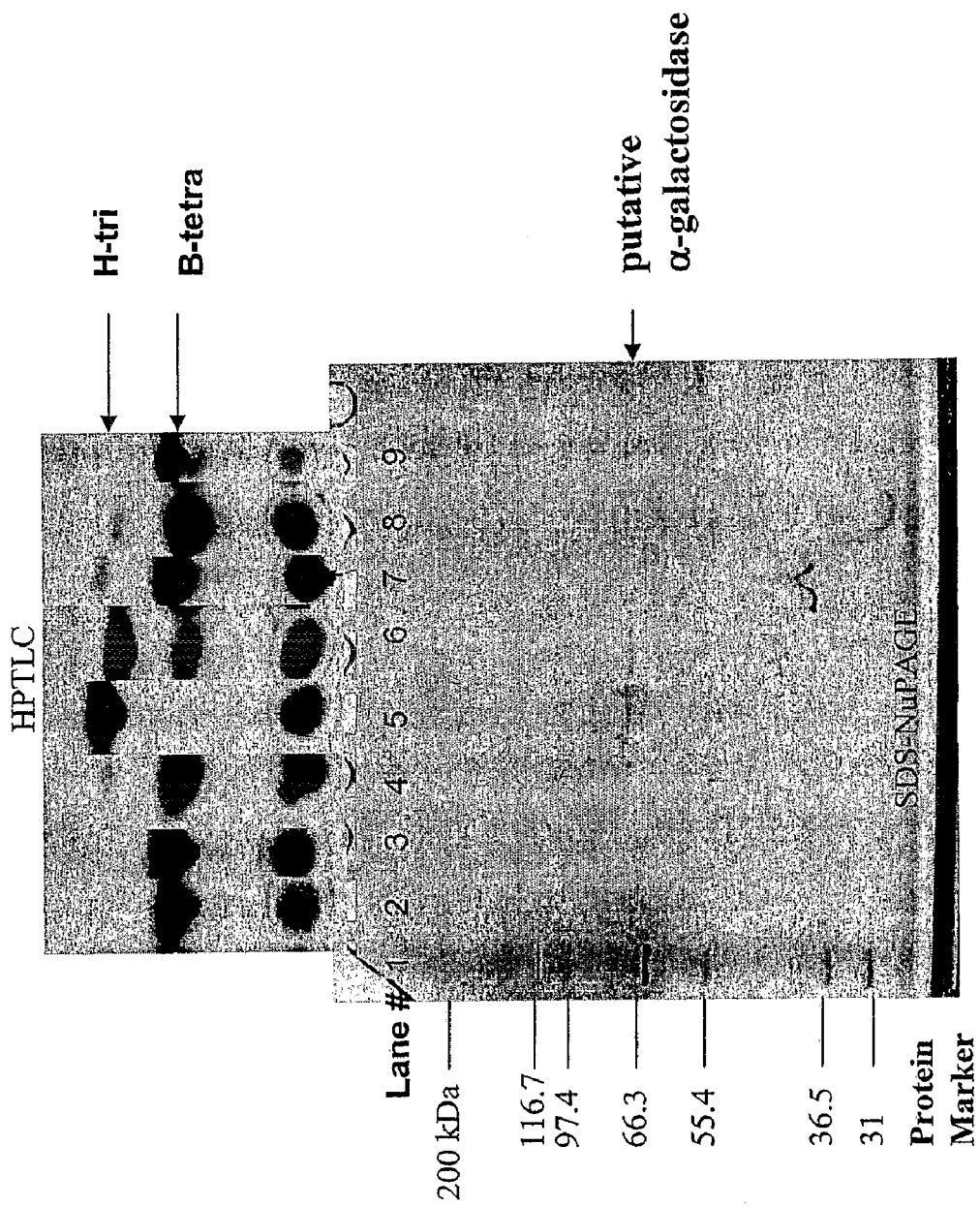
FIG. 8 illustrates a SDS-NuPAGE (Novex 4-12% Bis-Tris Gel with MOPS buffer, stained with SilverQuest Silver Staining kit, Mark12 Unstained Standard, all Invitrogen products) analysis of *Streptomyces griseoplanus* α-galactosidase activity purified by AEX. The HPTLC analysis of enzyme assays of fraction #3 of the wash/elution sample at each salt concentration in the AEX step as shown in FIG. 7, was placed at the top of the gel for easy comparison of the enzyme activity and protein band (s) on the gel. A single protein band, ~70 kDa, indicated by an arrow at right side of the panel labeled with putative α-galactosidase, is shown in the peak α-galactosidase activity. Designations: B-tetra, B tetrasaccharide, the substrate; H-tetra, H trisaccharide, the product.
Figure 9:
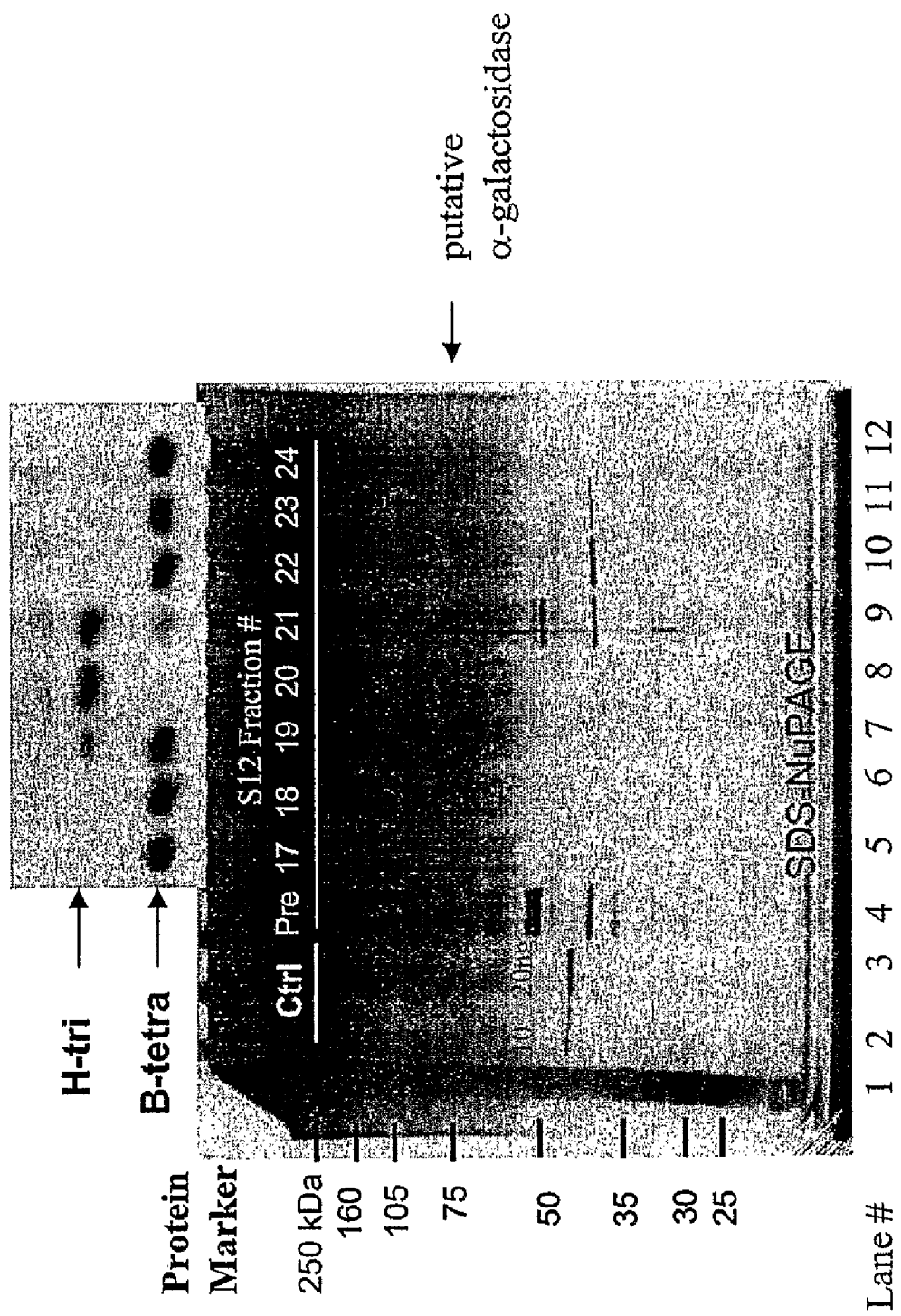
FIG. 9 illustrates comparative analyses of S12 chromatography fractions of partially purified *Streptomyces griseoplanus* α-galactosidase by SDS-NuPAGE and enzyme activity assay using B tetrasaccharide, analyzed by HPTLC. The putative 70 kD α-galactosidase band is indicated by an arrow at right side of the panel using Rainbow Molecular Weight Marker (Amersham, Cat. # RPN800). Designations: Ctrl, NEB A-zyme of known concentration; B-tetra, B tetrasaccharide, the substrate; H-tri, H trisaccharide, the product.

The following successive steps were used to achieve purification to apparent homogeneity: cell broth supernatant derived from cultures of S. griseoplanus #2357 was first passed unbound successively though CEX and DEAE columns (FIG. 4). Subsequently the activity was bound and eluted successively on a Hydroxyapatite column (FIG. 5), a Cibacron Blue column (FIG. 6), and finally an AEX column (FIGS. 7 and 8). Throughout the purification scheme the protein was followed by an analysis of its enzymatic activity in various fractions; the final protein product was also analyzed by SDS-NuPAGE. Identification of the α-galactosidase protein was obtained by comparison of protein banding pattern by SDS-NuPAGE silver staining and AEX and S12 gel filtration chromatographies (FIGS. 8-9). Only one band migrating as 70 kD by SDS-NuPAGE and S12 gel filtration, corresponded with the observed α-galactosidase activity. The protein identified as described, was finally separated by NuPAGE gel electrophoresis and the Coomassie stained 70 kD band was cut out of the gel and submitted for amino acid sequence analysis. Internal amino acid sequence information was obtained by mass spectrometric analysis (MALDI-TOF) and Edman degradation after trypsin digestion. None of the short sequences obtained showed high degree of identity with known sequences in public databases (GenBank). A Blast database search of a 30 amino acid peptide (the longest peptide sequence obtained by internal sequencing and confirmed by MS/MS, using "Search for short, nearly exact matches") identified a putative open reading frame predicted to encode a protein (SEQ ID NO: 2) from the genome sequence of Streptomyces avermitilis (GenBank access # BAC74979.1, GI:29610934). The complete genome of Streptomyces griseoplanus is not available and no related sequences derived from this genus were identified in database searches. Streptomyces avermitilis and Streptomyces griseoplanus are closely related. We therefore tested if Streptomyces avermitilis also contained the identified α-galactosidase activity, which was previously demonstrated to be very rare among bacterial isolates including many Streptomyces isolates.

Figure 11:
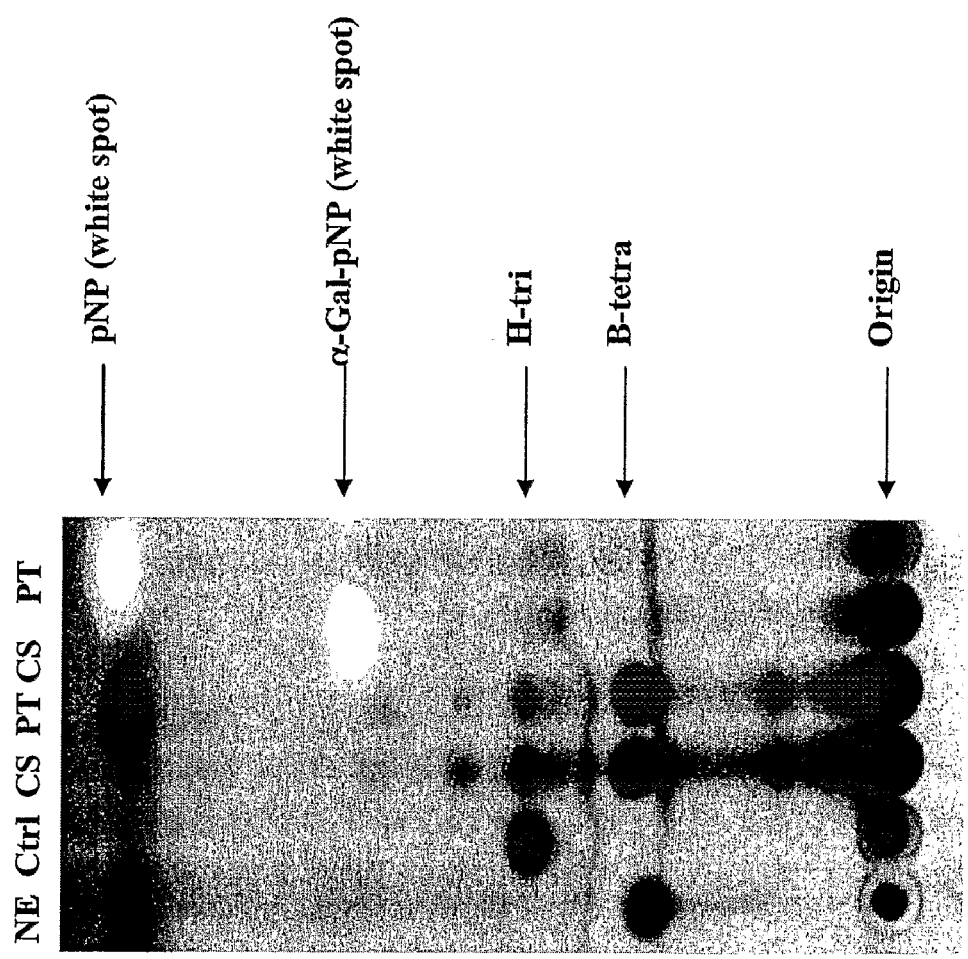
FIG. 11 illustrates an HPTLC analysis of enzyme assays of culture supernatant and pellet lysate of *Streptomyces avermitilis* grown in YM media (See Table II for formulations) with the AMC labeled blood group B tetrasaccharide and 4-methylumbelliferyl α-D-galactopyranoside (α-Gal pNP) substrates. The fermentation was carried out in for 3 days at 30° C., 220 rpm. Assays were performed by mixing equal volumes of the culture supernatant and 0.1 mM B-tetra or 0.5 mM of α-Gal pNP in 100 mM NaPO4 (pH 6.8) and incubated at room temperature overnight. One μL was sampled from each reaction and quickly applied onto HPTLC. Designations: NE, no enzyme control; Ctrl, positive control reaction by using Coffee bean α-galactosidase; CS, culture supernatant of *S. avermitilis*; PT, pellet lysate; B-tetra, B tetrasaccharide; H-tri, H trisaccharide; MU, 4-methylumbelliferone, the cleavage product of α-Gal pNP; Origin: the position in HPTLC where samples were applied. The TLC plate was developed in chloroform-methanol-water (vol/vol/vol: 60/35/8). The plate was scanned and photographed by a Bio-Rad Fluor-S MultiImager with Quantity One-4.1.1 software.

Streptomyces avermitilis (ATCC 31267) culture supernatant was assayed for secreted α-galactosidase and as shown in FIG. 11, clear evidence of the presence of α-galactosidase activities in both culture supernatant and pellet lysate was observed, as determined by digestion of B-tetra oligosaccharide substrates. However, the cleavage of a simple substrate (α-Gal pNP) by the secreted Streptomyces avermitilis α-galactosidase was negligible. In contrast, complete cleavage of α-Gal pNP was observed for the Streptomyces avermitilis α-galactosidase obtained from the cellular fraction. Therefore, the secreted and cellular α-galactosidases are probably not of the same identities. Part of the secreted galactosidase is likely to be the novel α-galactosidase that prefers branched substrate to simple (linear) substrates, while most of the cellular α-galactosidase activities if not all are observed to have conventional glycosidase activities. The similarities of the polypeptide from S. avermitilis (SEQ ID NO: 2) to the α-galactosidase from S. griseoplanus with respect to secretion into culture broth, predicted molecular weight, and the sequence similarities with S. griseoplanus, indicates that the S. avermitilis protein represents a homologue of the originally identified S. griseoplanus derived α-galactosidase.

The identified from S. avermitilis polypeptide (SEQ ID NO: 2) consists of 625 amino acids and showed no significant similarity to any other known proteins. Back searches with SEQ ID NO: 2 identified several novel protein sequences (SEQ ID NO: 3-8) from exclusively prokaryotic genomes, with sequence similarities shown as follows in Table 1A:

TABLE 1A

Identity (overall %) of Bacteroides α-Galactosidases to the S. avermitilis Enzyme.

| SEQ ID NO. | GI NO. | Abbr. | Amino Acids | Identity to SA (%) |
|---|---|---|---|---|
| 2 | gi\|29833810\|ref\|NP_828444.1\| S. avermitilis | SA | 625 | 100 |
| 3 | gi\|29340474\|gb\|AAO78266.1\| Bacteroides thetaiotaomicron VPI-5482 | BTα | 568 | 30.35 |
| 4 | gi\|53715733\|ref\|YP_101725.1\| Bacteroides fragilis YCH46 | BFα1 | 605 | 30.23 |

TABLE 1A-continued

Identity (overall %) of Bacteroides α-Galactosidases to the *S. avermitilis* Enzyme.

| SEQ ID NO. | GI NO. | Abbr. | Amino Acids | Identity to SA (%) |
|---|---|---|---|---|
| 5 | gi\|60495103\|emb\|CAH09922.1\| *Bacteroides fragilis* NCTC 9343 | BFα2 | 605 | 29.30 |
| 6 | gi\|60491830\|emb\|CAH06588.1\| *Bacteroides fragilis* NCTC 9343 | BFβ1 | 595 | 24.30 |
| 7 | gi\|53712216\|ref\|YP_098208.1\| *Bacteroides fragilis* YCH46 | BFβ2 | 595 | 24.30 |
| 8 | gi\|29341569\|gb\|AAO79356.1\| *Bacteroides thetaiotaomicron* VPI-5482 | BTβ | 615 | 22.82 |

All polypeptides identified were analyzed by multiple sequence alignments as shown in FIG. 12; a consensus sequence is provided as SEQ ID NO: 9. These polypeptides represent a new family of novel α-galactosidases, that have unique substrate specificity described in more detail below, and having the common feature of an approximately neutral pH optima.

The gene sequences for these members of this α-galactosidase family have allowed development of recombinant expression systems for these polypeptides, using a variety of prokaryotic or eukaryotic cells and expression systems, and permit purification of recombinant forms of these enzymes using established protein purification procedures (for example HIS tag expression and purification systems).

EXAMPLES

Enzyme Assays

Substrates consisting of a series of complex blood group ABH oligosaccharide structures, such as 7-amino-4-methyl-coumarin derivatives were custom synthesized by Alberta Chemical Research Council (see, U.S. Ser. No. 10/251,271). Other substrates were available from different suppliers (Sigma-Aldrich). All reagents used were of analytical grade or higher. Standard enzyme assays were performed as follows with the different substrates.

Typical assays were performed by the following procedure: Protein samples were incubated with AMC labeled oligosaccharide at 0.05 mM concentration, with MU-labeled monosaccharide at 0.25 mM concentration, in 2.2-10 μL reaction in 50 mM NaPO4 (pH 6.8) for the desired time at 26° C. or room temperature. One μL aliquot was taken at various time points and spotted onto HPTLC to follow product development. The TLC plate was developed in chloroform-methanol-water (vol/vol/vol: 60/35/8). The plate was scanned and photographed by a Bio-Rad Fluor-S MultiImager with Quantity One-4.1.1 software. One unit of enzyme activity is defined as the amount of enzyme required to cleave 1 μmole of substrate per minute under the experimental conditions.

Fermentations:

The formulations of various media were listed in Table II. Fermentations in flask and 50 mL conical tubes were performed under standard conditions: 30° C., 220 rpm for the desired length of time. The fermentation was performed at pH 6.8, 30° C., 300-600 rpm, DO=50%.

TABLE II

Media[1] formulations for growing *Streptomyces griseoplanus* for the production of α-galactosidase polypeptides

| Components | g/L |
|---|---|
| YM Medium | |
| Yeast extract | 3 |
| Malt extract | 3 |
| Bacto Soytone | 5 |
| Glucose | 10 |
| BP Medium | |
| Bacto Soytone | 15 |
| Malt extract | 5 |
| Yeast extract | 5 |
| Pharmamedia | 5 |
| KH2PO4 | 1 |
| MgSO4•7H2O | 1 |
| CaCO3 | 2.5 |
| Glucose | 25 |
| N-Acetylglucosamine[2] | 0.1 |
| Minimal Medium | |
| (NH4)2SO4 | 2 |
| MgSO4•7H2O | 0.6 |
| 0.2M NaH2PO4/K2HPO4 pH 6.8 | 7.5 mL |
| CaCl2 | 0.1 |
| ZnSO4•7H2O | 0.1 |
| FeSO4•7H2O | 0.1 |
| MnCl2•4H2O | 0.1 |
| Carbon source[2] | 5 |
| Trace mineral supplement (ATCC Cat. # MD-TMS)[2] | 10 mL |
| Vitamins supplment (ATCC Cat. # MD-TMS)[2] | 10 mL |

[1]All media without the indicated components were sterilized at 121° C. for 25 min.
[2]Components were sterilized by 0.22 μm filtration and added to the desired recipe after sterilization.

Example 1

Induction of α-Galactosidase Expression in *Streptomyces Griseoplanus*

*S. griseoplanus* was shown in the past to be capable of producing a secreted novel α-galactosidase when grown in proper media, although this enzyme was never purified to homogeneity. A cryostock of this microorganism was inoculated into 5 to 10 volumes of YM media and grown for 24 hrs at 30° C., 220 rpm, in shaking flasks or 50 mL conical tubes depending on the scale of the culture. The YM culture was then inoculated into about 20 volumes of BP media for continuing incubation under the same conditions, to induce production of the galactosidase. The enzyme activity associated with the culture usually peaks in 3 days. The culture supernatant containing the enzyme activity was harvested by centrifugation. FIG. 1 shows a HPTLC analysis of the enzyme assay of a typical spent culture media supernatant with the substrate B-tetra. The identified α-galactosidase was expressed in a very low volumetric yield both in total lysates of cells as well secreted into the medium (approximately ~0.1 U/L culture as analyzed by the B-tetra AMC enzyme assay described under general methods). Therefore, it was largely impossible to isolate sufficient amount of pure protein for sequencing (see, U.S. Ser. No. 10/251,271). The low expression level of the desired protein, the heterogeneity and protein richness of the rich media, were considered to represent the main factors for the difficulty to purify enough activity for protein identification.

It was considered necessary in the present study, to develop a strategy to induce expression and secretion of the enzyme to achieve a higher starting specific activity. One approach was to use an alternative carbon source instead of glucose. Another approach was to reduce the complexity of the media by using homogeneous media with little organic materials in particular the protein content, i.e., the minimal media. The isolation of the enzyme activity from such media was expected to be easier and yields of enzyme at each step were expected to be increased.

Figure 2:
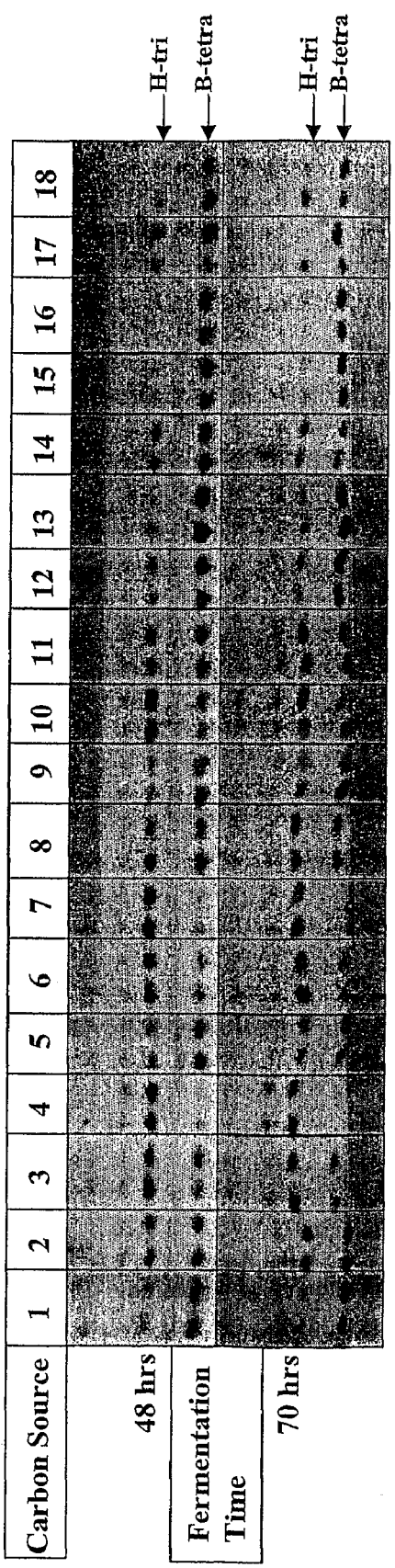
FIG. 2 illustrates a HPTLC analysis of enzyme assays of *Streptomyces griseoplanus* culture supernatants, recovered from cultures grown in minimal media with 18 different carbon sources, with the AMC labeled blood group B tetrasaccharide substrate. Assays were performed by mixing equal volumes of each culture supernatant and 0.025 mM B-tetra in 100 mM NaPO4 (pH 6.8), and incubated at room temperature. One μL was sampled from each reaction at 1 hr and spotted onto TLC plate. The carbon sources, indicated by number 1-18 at the top of the panel, are 18 different sugars used in the fermentation as shown in Table III. Designations: B-tetra: B tetrasaccharide, the substrate; H-tri: H trisaccharide, the product of the B-tetra substrate by α-galactosidase cleavage (The fast moving products above H-tri indicate the presence of fucosidase and β-galactosidase in the culture supernatants that cause further degradation of H trisaccharide into di- and monosaccharrides). Fermentations: Cryostocks of *Streptomyces griseoplanus* were thawed and inoculated into YM (~1:5-10, v/v) and incubated at 30° C., 220 rpm, for 24 hrs. The culture was passed onto BP media (~1:20, v/v) and fermentation was continued for 72 hrs. The mycelia, harvested from 100 mL of BP culture by centrifugation, were washed 3 times using basal minimal media (the minimal media lack of carbon source and trace metal/vitamin additives) to eliminate the rich media as much as possible. The pellet was then re-suspended in 100 mL of 2× basal minimal media with additives. The mycelia suspension was then aliquoted into 50 mL conical tubes at 2.5 mL/tube. Different carbon sources and water were then added to a final concentration of 0.5% and a final volume of 5.5 mL. Each carbon source was tested in duplicate. The 36 cultures of 5.5 mL of each, with 18 different carbon sources were incubated at 30° C., 220 rpm. Aliquot of 0.16 mL of culture was sampled from each tube at 43 and 71 hours.

Considering that the growth of the microorganism in minimal media is very slow and the sensitivity of α-galactosidase production to the growth media composition, *S. griseoplanus* was first grown in rich media following the standard protocol, i.e., 24 hrs in YM, 72 hrs in BP. The mycelia were then harvested from the culture by centrifugation. The pelleted mycelia were washed thoroughly with basal minimal media (minimal media lack of carbon source and additives) to eliminate the residual rich media as much as possible. The mycelia pellet was then re-suspended in minimal media lacking a carbon source, which can be easily distributed for carbon source screening as detailed in FIG. 2. The small scale tube cultures were performed under standard fermentation condition. Small aliquots were sampled at different time points and supernatants were recovered for α-galactosidase analysis. A total of 18 carbon sources were studied as shown in Table III. The HPTLC analysis of enzyme assays of culture supernatants with B-tetra are shown in FIG. 2. The complete disappearance of the substrates using 70 hrs fermentation supernatants in lane 4 and 7 clearly distinguish galactose and lactose from other carbon sources in their ability to produce the α-galactosidase. Under current assay condition, 25 pmol of substrate/μL of protein sample, 50 mM NaPO4 (pH 6.8), 1 hr at room temperature, the volumetric yield of the α-galactosidase activity can be calculated as follows:

25 μmol/(1 μL*60 min)≈0.4 mU/mL or 0.4 U/L.

The yield is much higher than a typical yield obtained from rich media culture (~0.1 U/L). Furthermore, the yield is probably underestimated since lack of time point before 1 hr may have missed the end point of the reactions. The preliminary result shows great potential of using minimal media to facilitate α-galactosidase production and purification.

Figure 3:
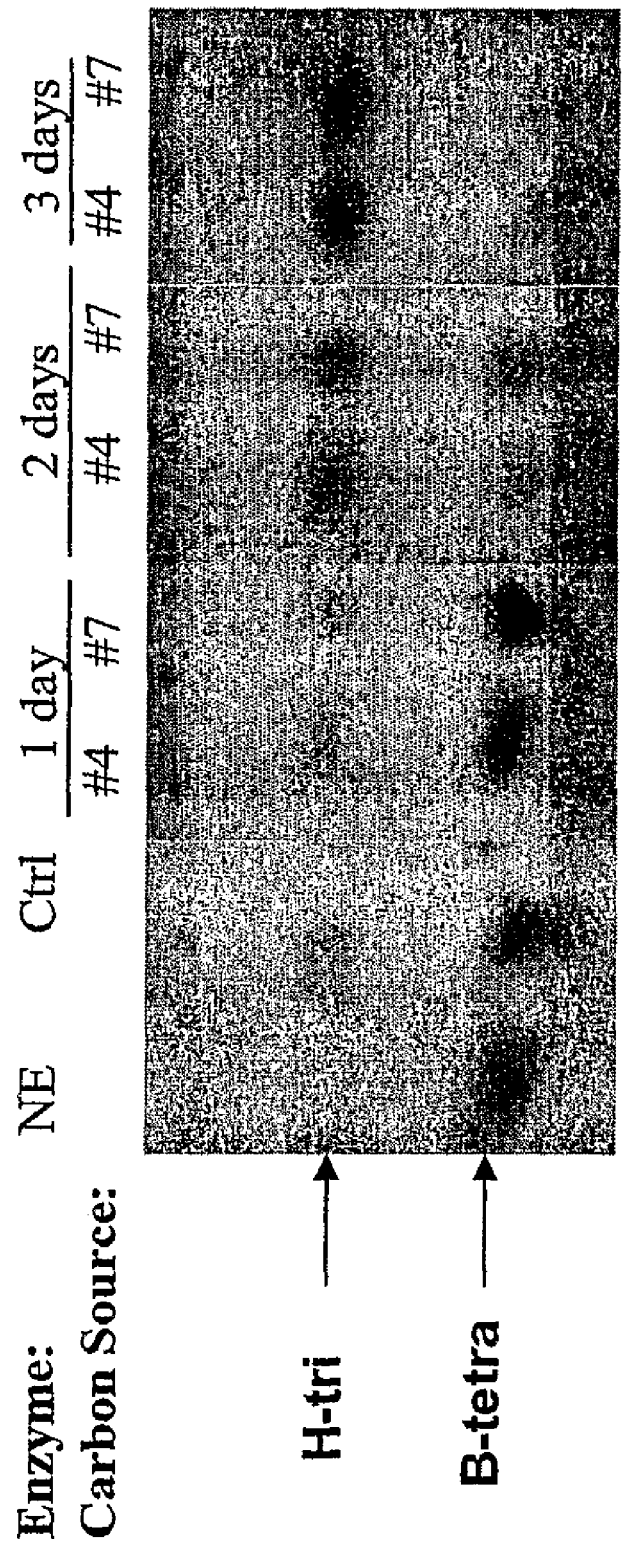
FIG. 3 illustrates an HPTLC analysis of enzyme assays of culture supernatant of *Streptomyces griseoplanus* grown in minimal media with either galactose or lactose as the sole carbon source with the AMC labeled blood group B tetrasaccharide substrate. Assays were performed by mixing equal volumes of each culture supernatant and 0.1 mM B-tetra in 100 mM NaPO4 (pH 6.8), and incubated at room temperature. One μL was sampled from each reaction at 20 min and applied onto a HPTLC plate for analysis. Designations: B-tetra: B tetrasaccharide, the substrate; H-tri: H trisaccharide, the product of the B-tetra substrate by α-galactosidase cleavage (The fast moving products above H-Tri indicate the presence of fucosidase and β-galactosidase in the culture supernatants that cause further degradation of H-Trisaccharide into di- and monosaccharrides); Carbon source: #4, galactose; #7, lactose; NE, no enzyme control; Ctrl, positive control reaction by using Coffee bean α-galactosidase.

To confirm the remarkable observation using minimal media, we re-evaluated the leading carbon source galactose and lactose for the novel α-galactosidase induction. FIG. 3 shows the HPTLC analysis of reaction assays of fermentation samples taken at different time points grown in minimal media with galactose and lactose as carbon sources. About 90% of the substrate was cleaved by 3 day culture samples in 20 min, which translated to about 4 U/L of culture supernatant. Therefore, as shown in FIG. 3, galactose (lane #4) and surprisingly lactose (lane #7) induced significant α-galactosidase activity. Then conditions for growth and induction using galactose identified above were used without further optimization to develop large-scale fermentations of the *Streptomyces* strain #2357 for isolation of the enzyme. As will be evident from the following examples these conditions were essential for the successful isolation and identification of the resultant α-galactosidase protein, which was different from the enzyme originally disclosed by U.S. Ser. No. 10/251,271.

TABLE III

Carbon sources used for screening novel α-galactosidase induction from *Streptomyces griseoplanus* using minimal media.

| Carbon Source # | Carbon Source |
| --- | --- |
| 1 | Carob tree crenel flour |
| 2 | Dextrin from potato starch |
| 3 | D(−) Fructose |
| 4 | D(+) Galactose |
| 5 | D(+) Glucosamine |
| 6 | Glycerol |
| 7 | D(+) Lactose monohydrate |
| 8 | Malt extract |
| 9 | D(+) Maltose monohydrate |
| 10 | D-Mannitol |
| 11 | D(+) Mannose |
| 12 | D(+) Raffinose |
| 13 | L(−) Sorbose |
| 14 | Starch |
| 15 | Sucrose |
| 16 | Xylitol |
| 17 | D(+) Xylose |
| 18 | D(+) Glucose |

Example 2

Purification of a α-Galactosidase Expressed in Streptomyces Griseoplanus Strain #2357

A new purification strategy was developed for the novel enzyme since the starting material was substantially different than that used for the partial purification described previously (see, U.S. Ser. No. 10/251,271). The following steps were used to achieve purification to apparent homogeneity: cell broth supernatant (450 ml), derived from 800 mL of culture carried out in an 1 L fermenter as described in Example 1, was subjected to 30 min's high speed centrifugation at 20,000 rpm, 4° C. The supernatant was applied to a 15 ml CEX column (Macro-Prep High S support, BioRad, Cat. #156-0031), pre-equilibrated with 40 mM NaPO4, 10 mM NaCl (pH 6.8), and washed with 40 ml of the equilibration buffer and 40 mM PO4, 10 mM NaCl (pH 7.3), respectively. The flowthrough and the two washes containing the α-galactosidase activity were pooled (FIG. 4, panel A), and applied onto a second column of 2.5 mL DEAE (DEAE Sepharose, Sigma, Cat. # DEF100) pre-equilibrated with 40 mM NaPO4, 10 mM NaCl (pH 6.8). The column was then washed with 50 ml of the equilibration buffer. A total of 600 ml containing the α-galactosidase activity was collected from the flowthrough and the wash (FIG. 4, panel B). They were pooled, concentrated with a Centricon Plus 80 Centrifugal filter devices (Millipore Cat. # UFC5LGC02), and buffer-exchanged to 10 mM NaPO4 (pH 7.0) in the same device to a final volume of 23 mL.

Figure 5:
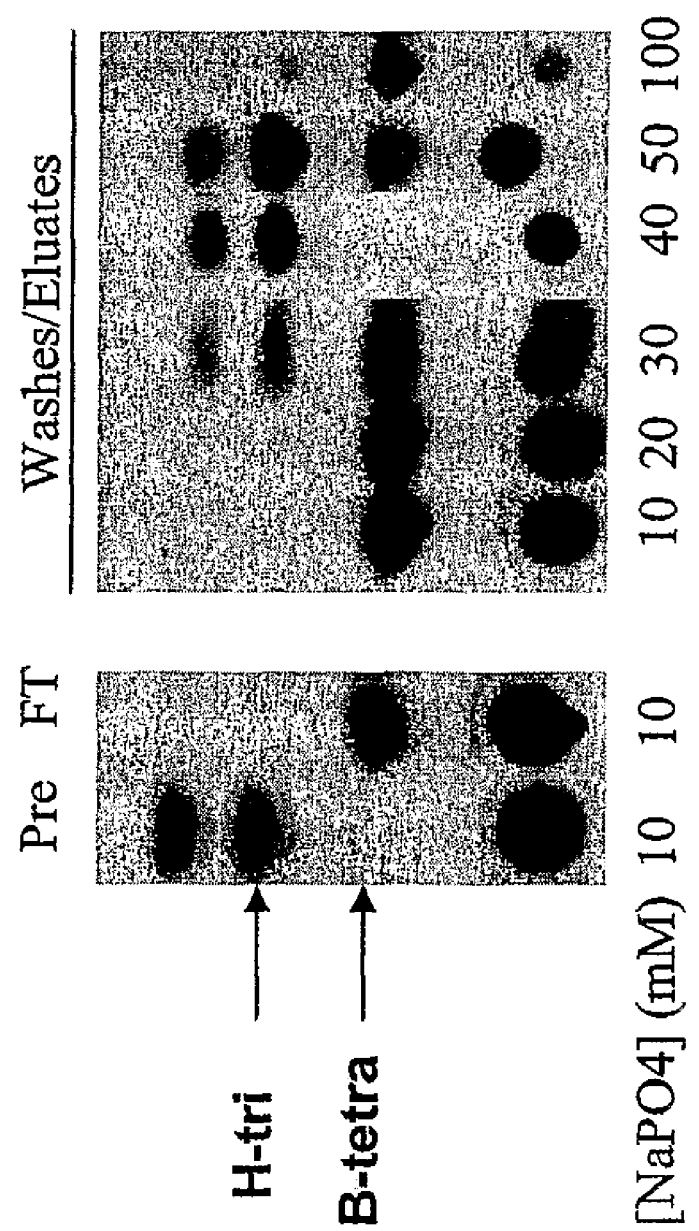
FIG. 5 illustrates HPTLC analysis of α-galacotosidase activity in various fractions from Hydroxyapatite step with B-tetra substrate. The protein sample in 10 mM NaPO4, pH 7.0, was loaded onto a 2.5 mL Hydroxyapatite column (Bio-Gel HT Hydroxyapatite, Bio-Rad Cat. # 130-0150), pre-equilibrated with 10 mM NaPO4 (pH 7.0). The column was washed with equilibration buffer and washed/eluted stepwisely with increasing amount of NaPO4 (10 to 100 mM). No activity can be detected in the flowthrough, indicating the effective binding of the enzyme to the column in the presence of 10 mM NaPO4 (pH 7.0). The appearance of enzyme activity in 30 mM NaPO4 wash and nearly complete lack of activity in 100 mM NaPO4 wash indicate simple elution of the enzyme from the Hydroxyapatite column just by using 30-50 mM NaPO4 (pH 7.0). Designations: Pre, protein solution before being loaded onto the column; FT, flowthrough.

The 23 ml buffer-exchanged sample was applied to a 2.5 ml Hydroxyapatite column (BioRad, Cat. #103-0150) pre-equilibrated with 10 mM NaPO4 (pH 7.0). The column was washed with 5 ml of the equilibration buffer, and the α-galactosidase activity was eluted stepwise with a NaPO4 gradient buffer (10 mM/step) from 20 to 100 mM (pH 7.0). The α-galactosidase activity eluted in fractions with 30-50 mM NaPO4 (FIG. 5). The active fractions were pooled and diluted 1:1 with $H_2O$ and applied to a 2.5 ml Cibacron Blue column (Sigma, Cat. # C-1285) pre-equilibrated with 10 mM Tris (pH 7.5). The column was washed with 10 ml of 10 mM Tris (pH 7.5) and 5 ml of 10 mM Tris, 80 mM NaCl (pH 7,5). The α-galactosidase activity was eluted with 25 ml of elution buffer containing 10 mM Tris (pH 7.5) with increased amount of salt (FIG. 6). The enzyme eluate was concentrated and buffer-exchanged into 40 mM Tris, 10 mM NaCl (pH 8.5)

with Centricon YM10 centrifugal filter devices (Millipore Cat. #4205) to a final volume of 3.7 mL. Finally, the buffer-exchanged eluate was applied to a 1 ml AEX column (Bio-Rad, Cat. #156-0031), pre-equilibrated with 40 mM Tris, 10 mM NaCl (pH 8.5). The column was washed with 5 ml equilibration buffer and the α-galactosidase activity was eluted with a NaCl gradient in 40 mM Tris (FIG. 7).

Analyses of the eluate fractions of the AEX column were performed by SDS-NuPAGE and a single band with apparent molecular weight of 70 kD was observed after silver staining (SilverQuest, Invitrogen, Cat. #LC6070) (FIG. 8). Further verification of the identity of the isolated α-galactosidase was provided by gel filtration chromatography. A S12 column (Superose 12™, Amersham, Cat. #17-5173-01) was equilibrated and run with 150 mM ammonium acetate. Partially purified α-galactosidase as described above was applied (250 μl volume) and 45 fractions (0.5 ml/fraction at 1 ml/min flow rate) were collected (FIG. 9). Fractions #19-21 contained the major protein peak (uv 280 nm). Fractions 19-22 were analysed for α-galactosidase with B-tetra AMC and 10 μl of each was analyzed by a 4-12% gradient SDS-NuPAGE using 10 and 20 ng of NEB A-zyme as controls (lane 2 & 3). As shown in FIG. 9 the peak α-galactosidase activity correlates fully with the 70 kD band by SDS-PAGE.

Example 3

Amino Acid Sequencing of Purified α-Galactosidase from *Streptomyces Griseoplanus* Strain #2357

Approximately 1 μg α-galactosidase protein as estimated by NuPAGE was prepared as described in Example 2. The protein was separated by 4-12% NuPAGE and stained with Colloidal Blue Staining Kit (Invitrogen, Cat. # LC6025). After destaining of the gel with H2O, the stained 70 KD bands were excised and washed with HPLC grade $H_2O$ and 50% acetonitrile in $H_2O$. The sliced gel was subjected to direct sequence analysis at the Harvard Microchemistry Facility, Harvard University. Briefly, gel slices were reduced with DTT and alkylated with iodoacetamide, and then digested with trypsin in 25 mM ammonium bicarbonate buffer. The trypsin digest was analyzed by microcapillary reverse-phase HPLC nano-electrospray tandem mass spectrometry (μLC/MS/MS) on a Finnigan LCQ DECA XP Plus quadrupole ion trap mass spectrometer. Preliminary sequencing of peptides was facilitated by database correlation with the algorithm SEQUEST. MS/MS peptide sequences were then reviewed for consensus with known proteins and the results manually confirmed for fidelity. No sequences from the NCBI nr or est databases correlated with this data.

Several attempts to obtain the N-terminal sequence of the undigested protein had failed to generate any sequencing information, suggesting that the N-terminus was blocked. In order to obtain internal sequence information peptides from the trypsin digest of the NuPAGE gel slices containing ~5 μg of the desired protein was fractionated by HPLC on a 0.3×150 mm C18 column. Three wavelengths were monitored; 205 nm (for amide bonds), 277 nm and 292 nm (for aromatic amino acids Trp and Tyr) via a diode array detector. A few of the best peaks/fractions were screened by MALDI to select peaks for Edman sequencing. Blast database searches using "search for short, nearly exact matches" against the NCBI nr database did not identify any identical sequences with any of the obtained peptide sequences. However, search using a 30 amino acid peptide sequence shown as SEQ ID NO: 12, the longest obtained peptide sequence and confirmed by MS/MS, did identify a candidate putative protein (SEQ ID NO: 2) predicted from the genome sequence of *Streptomyces avermitilis* (GenBank access # BAC74979.1, GI:29610934) that showed weak sequence similarity to SEQ ID NO: 12, the obtained griseoplanus peptide sequence (illustrated in FIG. 10).

SEQ ID NO: 12:   TVIDVTDFGADPSGKADSAAAVSAAMAHAK

The genome of *Streptomyces griseoplanus* is not available and no related sequences were identified in database searches. Notably, this sequence is not shared by the α-galactosidase described in our prior disclosure (and herein as SEQ ID NO: 1). *Streptomyces avermitilis* and *Streptomyces griseoplanus* are closely related. We therefore tested if *Streptomyces avermitilis* also contained the novel α-galactosidase, since the previous α-galactosidase was demonstrated to be very rare among many of the *Streptomyces* isolates tested (see, U.S. Ser. No. 10/251,271).

*Streptomyces avermitilis* (ATCC 31267) was cultured in YM media and the culture supernatant was assayed for secreted α-galactosidase using the AMC labeled B tetrasaccharide and a monosaccharide α-Gal pNP as substrates. As shown in FIG. 11, clear evidence of the presence of α-galactosidase activities in both culture supernatant and pellet lysate as analyzed by B-tetra oligosaccharide. However, the cleavage of a simple substrate α-Gal pNP is negligible by the secreted α-galactosidase activities. In contrast, complete cleavage of α-Gal pNP was observed for the cellular α-galactosidase(s).

The identified putative protein consisted of 625 amino acids (SEQ ID NO: 2) and showed no significant identity to any other known proteins. Back searches with the identified protein sequence identified very few protein sequences with low sequence similarities exclusively from prokaryotic genomes. All sequences identified were analyzed by multiple sequence analysis as shown in FIG. 12.

Example 4

Recombinant Expression and Characterization of Identified α-Galactosidase Gene from *Streptomyces Avermitilis*

The predicted full coding sequence of the identified *Streptomyces avermitilis* gene, 1878 base pairs in length, encoding the putative protein (SEQ ID NO: 2) of 625 amino acids (full length) was amplified by PCR (polymerase chain reaction) using the primer pair AVER1 (5'-GCGAATTC CCATGGCTCACGGATGCTCCGGAGGG-3' SEQ ID NO: 13)/AVER3 (5'-GCCTCGAG AAGCTTCTAGTCCGTGACCACGGAGGTGTTC-3' SEQ ID NO: 14), digested with NcoI/HindIII restriction enzyme (restriction sites in primers underlined), and cloned into the NcoI/HindIII site of the bacterial expression vector pPET28 (Novagen, Cat. No. 70777-3) forming the pZQ-B002a construct. Given the fact that the gene possesses an internal NcoI site at position 1490, insertion of the full-length gene construct was performed using a two-step cloning procedure. The expression construct was sequenced in full for confirmation. The generated full length expression construct pZQ-B002a was used to transform the *E. coli* strain Rosetta (BL21-DE3) pLysS (Novagen Cat. No. 70956-3), and plated out on LB-agar plates in the presence of Chloramphenicol (34 μg/ml) and Kanamycin (50 μg/ml).

Figure 13:
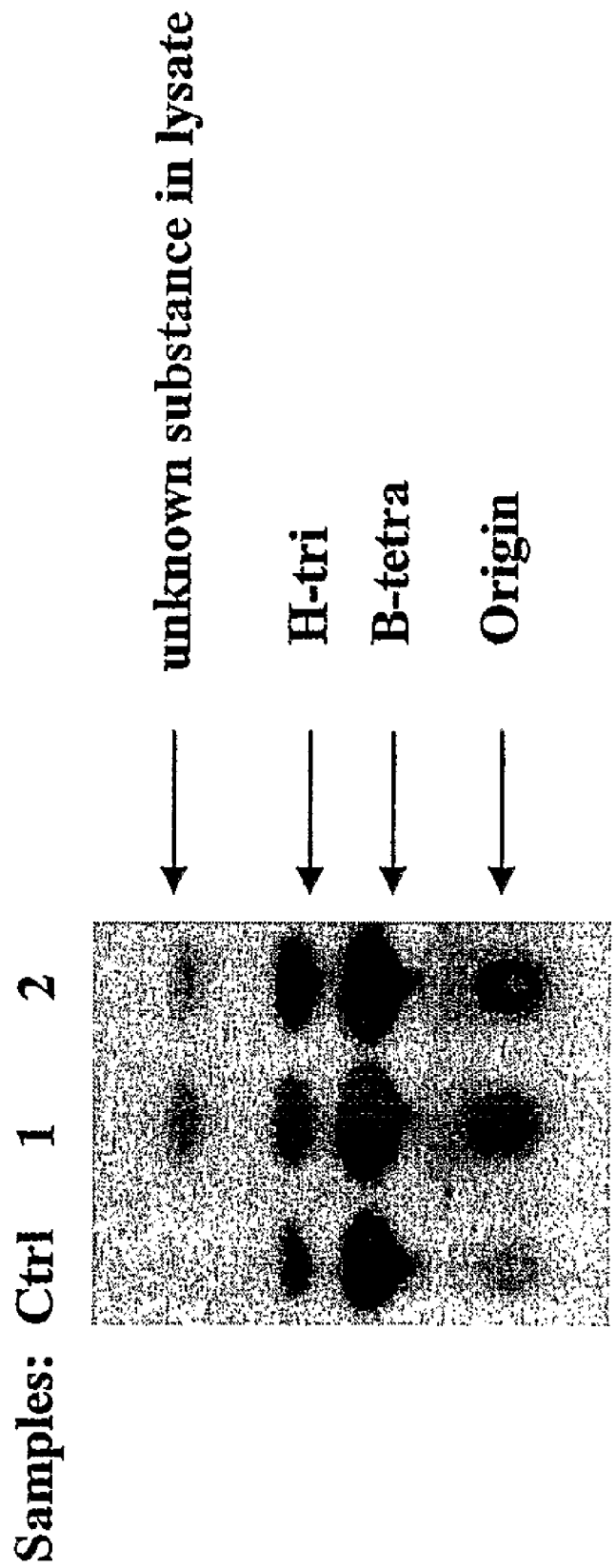
FIG. 13 illustrates an HPTLC analysis of the enzyme activities, of whole cell lysates of the cell pellet from IPTG induced cultures of *E. coli* clones (containing plasmids expressing the recombinant α-galactosidase gene from *Streptomyces avermitilis*), with the AMC labeled blood group B tetrasaccharide substrate. One mL of TB medium with antibiotics (48.2 g of EZmix Terrific Broth, Sigma T-91790, 8 mL of glycerol, 34 mg of Chloamphenicol, and 30 mg of Kanamycin per liter medium) was added to each 1.5 mL microtube containing the agar plug carrying a single colony. The cap was closed and incubation was performed overnight at 37° C., 250 rpm. One half mL of an overnight culture was inoculated into 10 mL of medium in a 50 mL conical tube and the incubation was carried under the same conditions. The cell density reached 0.3-0.6 OD600 nm in about 2 hrs at 220 rpm. The culture was removed from the shaker and kept at room temperature for ~20 min. Meanwhile, the temperature of the incubator was lowered to ~26° C. IPTG was then added to each culture at a concentration of 0.1 mM and all cultures were re-placed in the shaker and agitated at 220 rpm, to start protein induction. A 0.5 mL aliquot was removed aseptically from each tube in 1 hr and the cells pelleted with a bench top centrifuge at the highest setting for 5 min. Twenty μL of lysis buffer (0.9 mL of 40 mM NaPO4, 10 mM NaCl, pH 6.8, 0.1 mL of BugBuster 10×, Novagen 70921-4, 1 mg lysozyme/mL, and 5 μL of benzonase, Novagen 70664-3, per milliliter lysis buffer) was added to each tube to suspend the pellet and lyse the cells, which was assisted by pipetting the suspension up and down a few times. The lysis was completed in 5-10 min. An aliquot (2.2 μL) of the crude whole lysate was analyzed subsequently by mixing with equal volume of a substrate solution containing 0.1 mM of B-tetra in 100 mM NaPO4 (pH 6.8) and incubated at room temperature. One μL of the digestion was removed in 10 min and spotted onto a HPTLC plate. Designations: Ctrl, positive control reaction by using Coffee bean α-galactosidase; 1 and 2: whole lysates from two individual colonies of the same construct expressing the full length novel galactosidase from *Streptomyces avermitilis*; B-tetra, B tetrasaccharide; H-tri, H trisaccharide; Origin: the position in HPTLC where samples were applied. The TLC plate was developed in chloroform-methanol-water (vol/vol/vol: 60/35/8). The plate was scanned and photographed by a Bio-Rad Fluor-S MultiImager with Quantity One-4.1.1 software.
Figure 14:
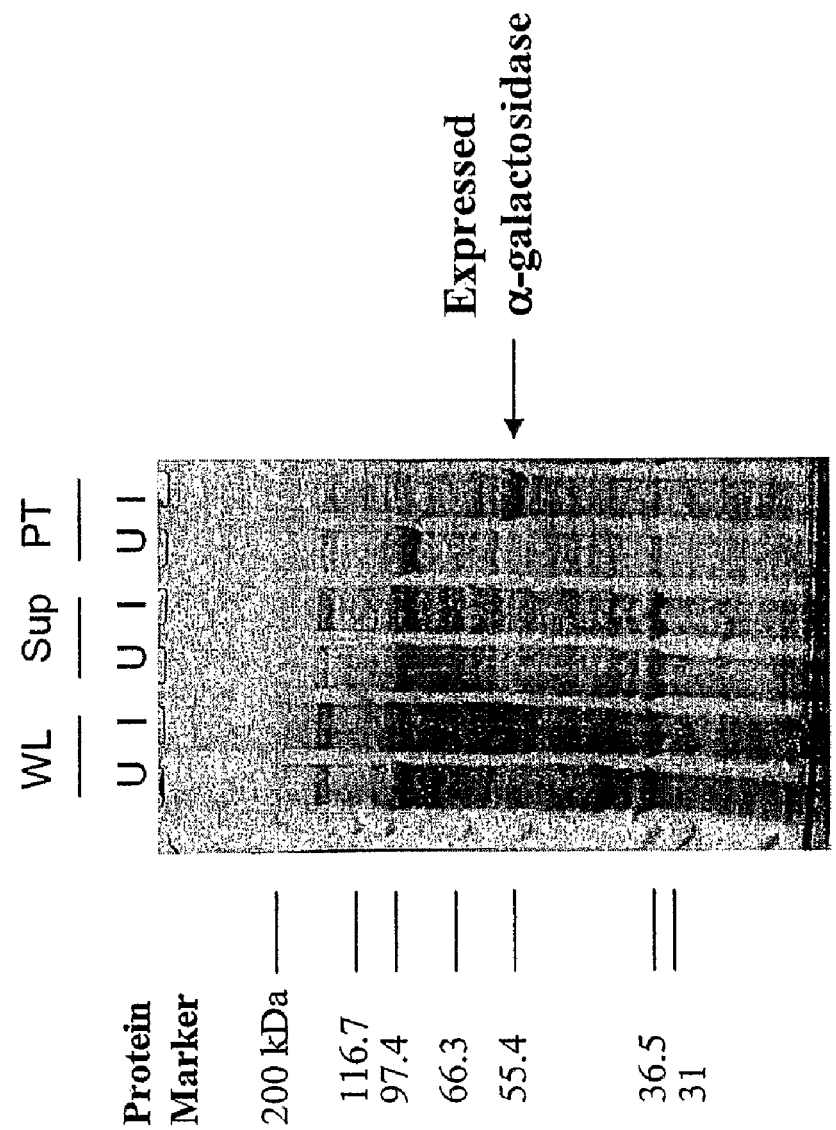
FIG. 14 confirmed that the novel B-zyme can be efficiently expressed in *E. coli*, but as inclusion bodies. Therefore, expression needs to be optimized or an efficient refolding method needs to be developed for the application of this novel B-zyme.

For initial analysis of the protein expression, induction was performed at 26° C. instead of the more common 37° C. with a low concentration of inducer (0.1 mM IPTG), a condition favoring the formation of soluble proteins. The induced cell pellet was lysed by a detergent based chemical method and whole lysate was assayed directly under standard condition for the novel B-zyme activity without being clarified. As shown in FIG. 13, the cleavage of the AMC labeled blood group B tetrasaccharide substrate was readily detectable as indicated by the formation of H trisaccharide using crude lysate generated from cultures induced only for 1 hr. This result unambiguously demonstrates the protein from *Streptomyces avermitills* (SEQ ID NO: 2) is indeed a novel galactosidase, a characteristic activity shared by other members of this family of proteins. FIG. 14 confirms that SEQ ID NO: 2 can be efficiently expressed in *E. coli,* but is recovered in inclusion bodies. Therefore, denaturation, extraction of the enzyme from inclusion bodies, and refolding are first necessary, for producing this polypeptide in *E. coli.*

Example 5

Enzymatic Conversion of B Red Blood Cells to O Phenotype Cells Using Expressed α-Galatosidase as Evaluated by Routine Typing Protocols Conversion Protocol One—Enzymatic conversion reactions were performed in 1 ml reaction mixtures containing 200 mM glycine, pH 6.8, and 3 mM NaCl with 30% packed red blood cells (pRBCs) and enzyme as indicated. Fresh whole blood was obtained from Oklahoma Blood Institute (Oklahoma City, Okla.) and buffy coat removed. RBCs were prewashed 1:1 and 1:4 vol/vol in conversion buffer before addition of enzyme, and reactions incubated for 60 min with gentle mixing at 26° C., followed by four repeat washing cycles with 1:4 vol/vol of saline by centrifugation at 1,000 rpm. The washed enzyme-treated B-ECO RBCs were ABO typed according to standard blood banking techniques using various commercially available monoclonal antibody reagents ((Immucor Gamma Anti-B (Gamma Biologicals/Immucor, Norcross, Ga.); Ortho Anti-B (Ortho Clinical Diagnostics, Raritan, N.J.); and Diagast Anti-B (Diagast Laboratories, France)).

Conversion Protocol Two—B red cells (Beth Israel Deaconess Medical Center, Boston, Mass.) are drawn into EDTA tubes and stored at 4° C. for up to seven days, and are washed three times in PBS (Phosphate Buffered Saline, pH 7.4), and resuspended to 10% in a solution of PBS and 7.5% PEG (pH 7.4). Cells are treated with recombinant α-galactosidase (10-500 U/ml) at 30° C. for 180 min while shaking. Cells are washed three times in 0.9% saline and resuspended to 3-5% in saline for typing.

Conversion Protocol Three—B red cells (Beth Israel Deaconess Medical Center, Boston, Mass.) are drawn into EDTA tubes and leukoreduced B red cells (American Red Cross, New England Region, Dedham, Mass.) are frozen in Glycerolyte 57, (Baxter Healthcare Corporation, Fenwal Division: Deerfield, Ill.) according to the AABB Technical Manual, 13th edition, Method 6.6 and stored at −70° C. Prior to enzyme treatment cells are deglycerolized using 9.0% saline, 2.5% saline, and 0.9% saline (see, Method 125 of Immunohematology Methods by the American Red Cross), then resuspended to a hematocrit of 50% in a solution of PBS and 7.5% PEG (pH 7.4) and recombinant α-galactosidase (200 U/ml) is added. Reactions are incubated at 37° C. with shaking for 4 hours, followed by three washes in 0.9% saline, and final suspension to 3-5% in saline for typing.

Conversion Protocol Four—Origin and storage of cells is the same as described under protocol B. Deglycerolized red cells are washed twice in PCI (pH 7.4) with 150 mM NaCl and resuspended to a hematocrit of 50% in PCI (pH 7.4) with 150 mM NaCl. Cells are treated with recombinant α-galactosidase (200 U/ml) at 37° C. with shaking for 4 hours, followed by three washes in 0.9% saline, and final suspension to 3-5% in saline for typing.

Approved typing reagents used in hemagglutination assays are murine monoclonal antibodies and plant lectins obtained from Ortho Clinical Diagnostics, Raritan, N.J.; Gamma Biologicals/Immucor, Norcross, Ga. Non-FDA approved reagents included murine monoclonal anti-B antibodies to blood group B variants produced by H. Clausen (Clausen et al., Proc. Natl. Acad. Sci. USA 82(4): 1199-203, 1985, Clausen et al., J Biol. Chem. 261(3): 1380-7,1986, Clausen et al., Biochemistry 25(22): 7075-85,1986, Clausen et al., J Biol. Chem. 262(29): 14228-34,1987). Typing reagents are used according to the manufacturers recommendations and other monoclonal antibodies as determined by titrations.

Hemagglutination Assay (room temperature).

A 3-5% suspension of washed red cells in isotonic blood bank saline is prepared. One drop (approx 50 microliters) of anti-B antibody reagent is added. One drop (approx 50 microliters) of the red cell suspension is added. Tubes are mixed and centrifuged for 15 seconds at 3500 rpm. Cells are resuspended by gentle agitation and examined macroscopically for agglutination. The agglutination is graded according to Method 1.8 in the AABB Technical Manual, 13$^{th}$ edition.

As described in the previous examples, preferred enzymes for use in removing blood group B epitopes from red cells are likely to have particularly good kinetic properties with oligosaccharide substrates resembling the blood group B antigens. Such preferred kinetic properties could be represented by preferred or exclusive substrate specificities for the blood group B oligosaccharides, and low or no activity with simple monosaccharide derivatives such as monosaccharide-pNP substrates. Preferred kinetic properties could also be represented by a particularly low Km for relevant substrates. Further preferred kinetic properties consist of neutral pH optimum of reactions with relevant blood group active substrates, and other reaction conditions that are compatible with the integrity and functions of red cells. Other preferred properties of the enzyme such as size, charge, solubility, and other physico-chemical properties may also relate to performance in enzymatic conversion of red cells. The novel α-galactosidase with improved kinetic properties was identified from various bacterial strains as described and provides an enzyme with the above mentioned preferred characteristics, that exhibits superior performance in red cell conversions.

TABLE 3A

Agglutination Results of human red cells converted with FragA or FragB recombinant αgalactosidases.

| Routine Conversion Protocol (200 Glycine, pH 6.8, 3 mM NaCl) | | Immucor Anti-B | | Diagast Anti-B | |
|---|---|---|---|---|---|
| | Dose µg/ml | IS | 4° C. | IS | 4° C. |
| Frag B enzyme | | | | | |
| Human B Cells | 10 | 0 | 0 | 0 | 0 |
| | 5 | 0 | 0 | 0 | 0 |
| | 2.5 | 0 | 0 | 0 | 0 |
| | 1.25 | 0 | 0 | 0 | 0 |
| | 0.625 | 0 | W+ | W+ | 1+ |
| | 0.3125 | 0 | 1+ | 1+ | 1+ |

TABLE 3A-continued

Agglutination Results of human red cells converted with FragA or FragB recombinant αgalactosidases.

| Routine Conversion Protocol (200 Glycine, pH 6.8, 3 mM NaCl) | | Immucor Anti-B | | Diagast Anti-B | |
|---|---|---|---|---|---|
| | Dose µg/ml | IS | 4° C. | IS | 4° C. |
| Frag A enzyme | | | | | |
| Human B Cells | 10 | 0 | 0 | 0 | 0 |
| | 5 | 0 | 0 | 0 | 0 |
| | 2.5 | 0 | 0 | 0 | 0 |
| | 1.25 | 0 | 0 | 0 | 0 |
| | 0.625 | 0 | W+ | W+ | 1+ |
| | 0.3125 | 1+ | 1+ | 1+ | 2+ |

Example 6

Figure 15:
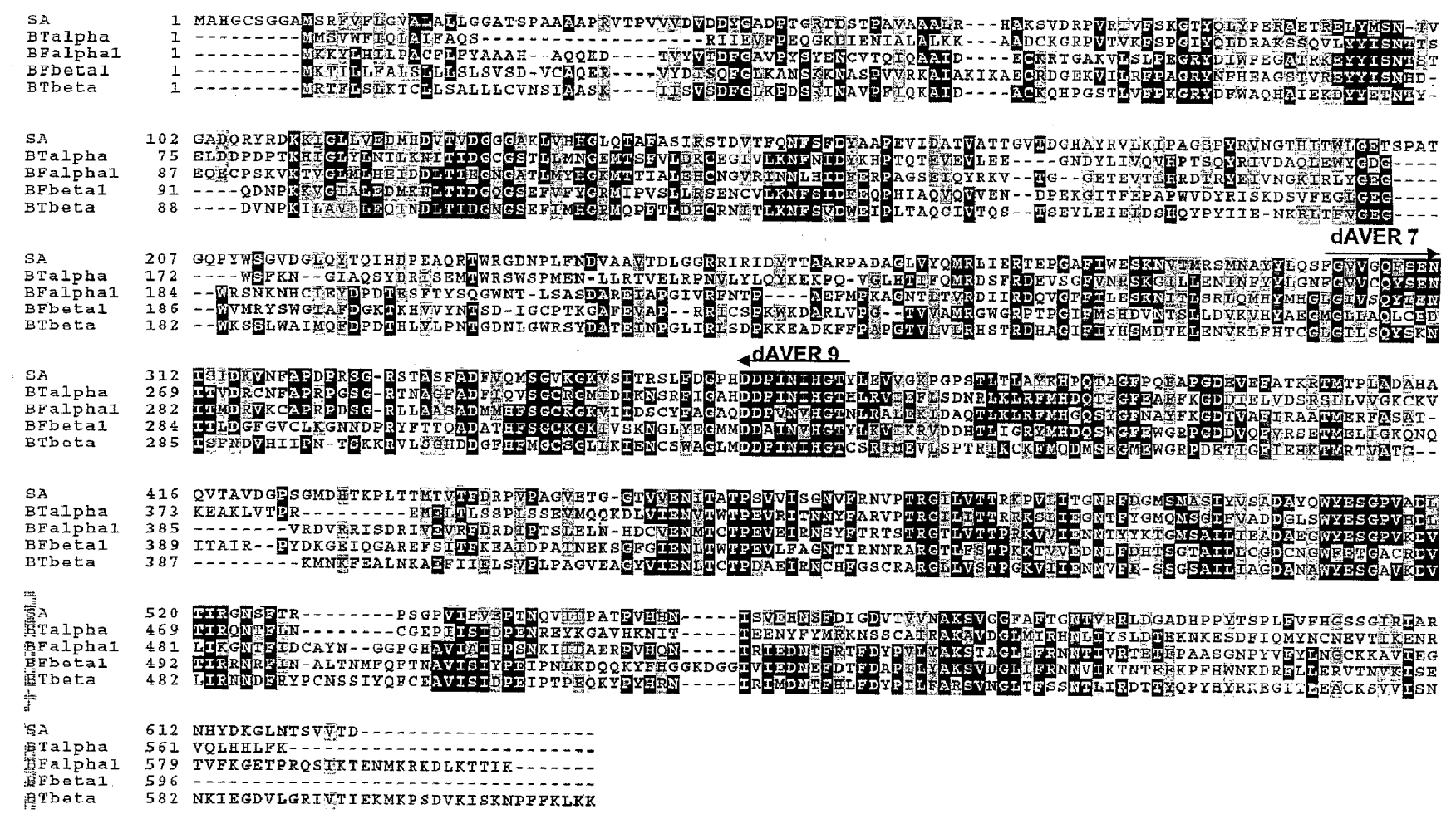

Cloning and DNA Sequencing of α-Galactosidase from Streptomyces Griseoplanus Strain #2357 and Deduction of its Amino Acid Sequence The isolation and purification of the endogenous α-galactosidase from *S. griseoplanus* 2357 was described in Example 2. The partial amino acid sequencing of purified α-galactosidase that generated a 30 amino acid peptide was described in Example 3. Blast search using this peptide against 'nr' database (GenBank) identified a family of putative α-galactosidases. The sequences for the 5 α-galactosidases were submitted to the EMBL/GenBank/DDBJ databases and assigned the following accession numbers: AM109953 (*Streptomyces avermitilis*), AM109954 and AM109955 (*Bacteroides fragilis*), AM109956 and AM109957 (Bacteriodes thetaiotaomicron). Multiple sequence alignment of putative α-galactosidases identified a few conserved regions (FIG. 15). The open reading frame encoding a putative α-galactosidase from *Streptomyces griseoplanus* was cloned based on 5' and 3' rapid amplification of genomic ends (RAGE). Initial degenerate primers were based on the conserved regions determined from multiple sequence alignment of putative α-galactosidase sequences. Degenerate sense and anti-sense primers dAVER7 (5'-TTCGGXGTXGTXKGKCAGTW-CAGXGAGAA-3' SEQ ID NO: 15)/dAVER9 (5'-GTXCCX-TGXATXTTXATXGGXTCXTCGTG-3' SEQ ID NO: 16), where X=inosine and K=G or T, were used to PCR amplify a single 185 bp BZyme specific DNA fragment from *Streptomyces griseoplanus* genomic DNA. PCR product was cloned into pCR4 vector (Invitrogen) and sequenced generating pCR4-dAVER7/9. *Streptomyces griseoplanus* α-galactosidase specific primers GRIS10 (5'-ATCGACTCGGTCACCT-TCAAGGCCGAC-3 SEQ ID NO: 17) and GRIS11 (5'-AA-GACGCTGTTGGTGATGCGTACGGTGC-3' SEQ ID NO: 18) were derived from pCR4-dAVER7/9. *Streptomyces griseoplanus* genomic DNA was endonuclease treated to completion with restriction endonuclease HaeII, size fractionated by 0.8% agarose gel electrophoresis and 2-3 kbp fractionated DNA was purified by Qiagel purification (Qiagen). Purified DNA was ligated to a double stranded HaeII adapter EBRETTE3 (5'-GCG CTCGAAATTAACCCTCACTAAAGGGGGAATTCGG-TACCCTCGAG GCGC-3' SEQ ID NO: 19)/EBRETTE4 (5'-CTCGAGGGTACCGAATTCCGGAA-3' SEQ ID NO: 20) encoding a T7 binding site (underlined) and HaeII restriction overhang (shown in italics). Adapter ligated DNA was used in 5' RAGE using 10 ng adapter ligated DNA, T7/GRIS11 or 3'RAGE using 10 ng T7/GRIS10. Generated 5' and 3' RAGE products were cloned into pCR4 generating 5'-T7/GRIS11-pCR4 and 3'-T7/GRIS10-pCR4 and fully sequenced. The overlapping 5'-T7/GRIS11-pCR4 and 3'-T7/GRIST10-pCR4 sequences represent 1593 bp of the full coding BZyme gene sequence. Remaining 5' and 3' sequence was obtained by repeated RAGE on fractionated BamHI digested *Streptomyces griseoplanus* genomic DNA, BamHI adapter EBRETTE3/6 (5'-GATCGCGCCTCGAGGGTACCGAAT-TCCGGAA-3' SEQ ID NO: 21) ligated (BamHI overhang shown in italics). Complete 5' sequence was obtained using 10 ng adapter ligated DNA and T7/GRIS22 (5'-CGCTTCG-GCGTCCGTTCGGGCCAG-3' SEQ ID NO: 22) and 3' sequence using T7/GRIS24 (5'-CCGGTGCACCG-CAACGTCCTCATC-3' SEQ ID NO: 23). Generated 5' and 3' RAGE products were cloned into pCR4 generating 5'-T7/GRIS22-pCR4 and 3'-T7/GRIS24-pCR4 and fully sequenced. 5'-T7/GRIS22-pCR4 contained a predicted initiating start methionine and 3'-T7/GRIS24-pCR4 contained an in frame stop codon, completing the full 2184 bp coding sequence of *Streptomyces griseoplanus* α-galactosidase gene (SEQ ID NO: 24) encoding a 727 amino acid α-galactosidase (SEQ ID NO: 25). The sequence was submitted to GenBank (accession number AM259273). The regions in protein sequence of the α-galactosidase from which the primers were derived are described in FIG. 16.

Example 7

Recombinant Expression and Characterization of Identified α-Galactosidase Gene from *Bacteroides Fragilis*

FragB α-galactosidase (SEQ ID NO: 6) expression construct was cloned from genomic bacterial DNA by PCR. The FragB α-galactosidase gene, lacking the coding region for the putative amino terminal signal peptide 1-24, was lifted from Bacteroides fragilis genomic DNA (ATCC 25285D) by PCR using primers BFRAGB2 (5'-GCGGGATCCCGGGATGG-GACGTGTTTATGACATTTCCCAGTTTGGC-3' SEQ ID NO: 24)/BFRAGB3 (5'-GCCTCGAGAAGCTTTCACTCT-GAAATCTTCACGTTTGTCACTCG-3' SEQ ID NO: 25) and amplified using Pfu Ultra polymerase (Stratagene). Restriction enzyme overhangs for BamH I and Hind III in the above primers are underlined. After digestion with BamH I and Hind III, the amplified polynucleotide products were inserted into the bacterial expression vector pET28 (Novagen) in frame and downstream of the plasmid encoded 6xHis tag (SEQ ID NO: 29) to generate plasmid pZQ-B006a. For the construction of a non tagged expression vector, the 6xHis tag (SEQ ID NO: 29) in pET28 vector was removed by NcoI/BamHI digestion followed by insertion of a double stranded oligo PETNCBAF (5'-CATGGATCCCAGGCCTC-CGGATG-3' SEQ ID NO: 26)/(GATCCATCCGGAGGC-CTGGGATC-3' SEQ ID NO: 27) creating plasmid pET28-δ-His. The FragB construct described above encoding the His-tagged protein was sub-cloned into the pET28-δ-His BamHI/HindIII site to create plasmid pZQ-B006c for the expression of the untagged FragB α-galactosidase. All constructs were fully sequenced on a 377 ABI Prism instrument (Applied Biosystems). For protein expression, pZQ-B006c was transformed into *E. coli,* Rosetta2 (DE3) (Invitrogen). The *E. coli* clone was grown in 1X Terrific Broth (Sigma), supplemented with 34 µg/mL of Chloramphenicol and 50 µg/mL of Kanamycin at 37° C., 220 rpm to~0.6 OD at 600 nm and IPTG was added to 0.5 mM to induce the target protein expression. The culture was harvested after 3 hrs, by centrifugation at 3000 xg for 30 min. The cell pellet was stored at −20° C. The cell pellet harvested from 350ml culture was lysed using 1X BugBuster (Invitrogen) in 25 mM NaOAc, pH 5.5/10 mM NaCl, supplemented with 5 μL of Benzonase (Invitrogen), and stirred for 1 hr at room temperature. The whole lysate was clarified by centrifugation at 40,000 x g, 5° C., for 30 min. The cell debris, containing over 90% enzyme activity, was re-suspended in 10 mM NaPO4, pH 6.8/400 mM NaCl and stirred at room temperature for 30 min. High speed centrifugation was repeated to recover the supernatant containing the enzyme activity. The resulting supernatant was loaded onto a 5-ml Hydroxyapatite column, pre-equilibrated with 10 mM NaPO4, pH 7.0. The column was washed with 20 mL of equilibration buffer, followed by elution using a NaPO4 gradient, pH 7.0, from 10 to 400 mM. The enzyme activities, eluted between 200-400 mM NaPO4, pH 7.0, were pooled, concentrated and buffer exchanged with an Amicon (Grace) centrifugal device Plus 70, into 10 ml of 40 mM Tris, 400 mM NaCl/pH 7.5. The protein solution was allowed to pass through a 5-ml Phenyl Sepharose High Performance column (Amersham), pre-equilibrated with the dialysis buffer, and the column was washed with 10 mL of dialysis buffer after loading. The flow through and wash were pooled, adjusted to pH 8.5 with 1 M Tris, diluted with equal volume of $H_2O$. The resulting protein solution was subjected to another passage column step, 2.3 mL of Macro-Prep High Q, pre-equilibrated with 40 mM Tris, pH 8.5/10 mM NaCl, and the column was washed with 10 mL of equilibration buffer. The flow through and wash were pooled and buffer exchanged into 7 ml of 10 mM NaPO4, pH 6.8/50 mM NaCl. The protein concentration was determined by Pierce's BCA Protein Assay Kit.

Figure 17:
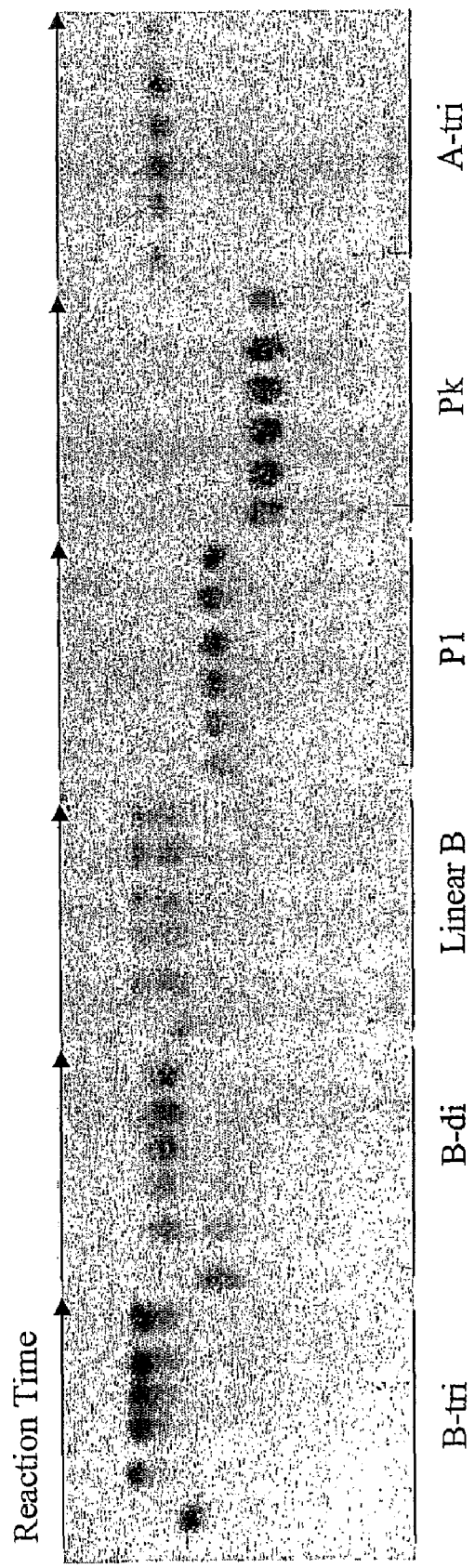
FIG. 17 illustrates a HPTLC analysis of enzyme assays of purified recombinant FragB α-galactosidase with a panel of oligosaccharides of diverse structures. Reactions were performed at room temperature with 10 nmole of substrate and 21 ng of enzyme in 10 μL of 10 mM NaPO4, pH 6.8/2.5 mM NaCl, supplemented with 0.25 mg/mL of BSA. One μL of enzyme assays was removed at desired time points and spotted onto a silica gel-coated TLC plate (EMD Chemicals, NJ), which was developed in chloroform-methanol-water (vol/vol/vol: 30/60/10) for 15 min and product developments were detected by Orcinol/$H_2SO_4$ staining. Designations: Reaction time for each substrate from left to right: 0 (sampled from control reaction containing no enzyme), 5,10, 20, 40 and 80 min. Detailed structures of the substrates are described in Table V. The cleavage of the substrate resulted increased migration as observed for B-tri, B-di and linear B, but not for $P_1$, $P^k$ and A-tri, indicating the lack of cleavages.
Figure 18:
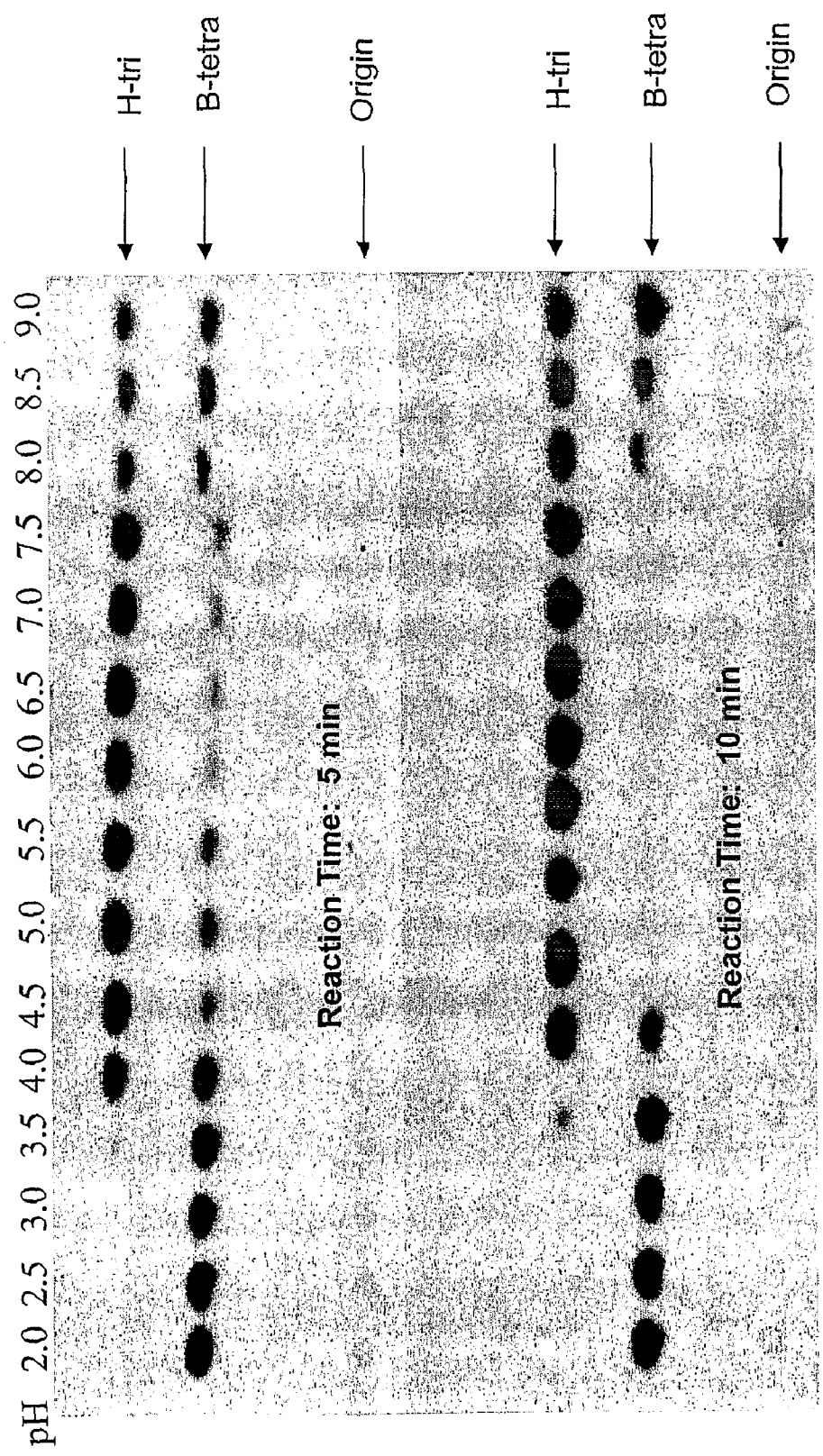
FIG. 18 illustrates a HPTLC analysis of enzyme assays of purified recombinant FragB B-zyme with AMC-B-tetra under different pH. Reactions were performed at room temperature with 1 nmole of substrate and ~8 ng of enzyme in 10 μL of buffer at pH 2.0 to 9.0, supplemented with 0.25 mg/mL of BSA. One μL of enzyme assays was removed at desired time points and spotted onto a HPTLC plate, which was developed in chloroform-methanol-water (vol/vol/vol: 60/35/8). The plate was scanned and photographed by a Bio-Rad Fluor-S Multimager with Quantity One-4.1.1 software. The 1× buffers used in the reactions were derived from 2× buffers described as follows: pH 2.0, 0.1 M citric acid; pH 2.5-5.5, 0.1 M citric acid/0.2 M Na2HPO4; pH 6.0-7.5, 0.2 M NaH2PO4/0.2 M Na2HPO4; pH 8.0-9.0, 0.2 M Tris/HCl. Assay mixtures were sampled at 5 (top panel) and 10 min (bottom panel). Designations: B-tetra, B tetrasaccharide; H-tri, H trisaccharide; Origin: the position in HPTLC where samples were applied.

The purified FragB α-galactosidase was evaluated for its ability to cleave the branched carbohydrate chain substrate B-tetra under standard conditions (1 nmole of substrate in 10 μL of 100 mM $NaPO_4$, pH 6.8/50 mM NaCl), and the purified enzyme demonstrated extremely high specific activity toward the B-tetra substrate: ~5-10 U/mg. The pH optimum of the purified FragB α-galactosidase was evaluated with the B-tetra-AMC substrate across a pH range of 2.0 to 9.0 and the results are shown in FIG. 17. The FragB enzyme has a broad optimal pH range between 4.5 and 7.5. Analysis with the more sensitive/quantitative colorimetric assay gives the similar conclusion as shown in FIG. 18, although the enzyme's activity was seen at the low end of the pH range tested, i.e., activity was observed down to ~pH 4.2, a subtle difference in activity which is not detectable by using the TLC based AMC-B-tetra assay. Therefore, the novel enzyme can be used successfully under acidic conditions to neutral condition and even slightly basic conditions, i.e., about pH 4 to about pH 7.4 or greater. In currently preferred embodiments, the enzyme is used within a pH range of about 6.0 to about 7.5, and more preferably about pH 6.5 to about pH 7.5. The currently most preferred pH range for the novel enzyme are those conditions mimicking the physiological pH of circulating arterial or venous blood, in order to minimize pH effects on the blood cells themselves and not because of pH limitations on enzyme activity and performance.

The FragA α-galactosidase (SEQ ID NO: 5) was cloned similarly by PCR from the same genomic DNA as for FragB α-galactosidase, and expressed similarly as $His_6$ tag (SEQ ID NO: 29) protein at the N-terminus in Rosetta (DE3) pLysS (Novagen). Expressed soluble protein was purified to homogeneity by successive immobilized metal affinity chromatography (IMAC), cation and anion exchange chromatography. The purified protein was shown to be similar to the endogenous S. griseoplanus α-galactosidase (strain 2357) in terms of specific activity for branched substrate, substrate specificity and pH optima. Analysis of activity with a blood group B tetrasaccharide-AMC substrate in the pH range of 2-9 showed that the enzyme has a broad optimum between 5 and 7.5. The substrate specificity of the FragA α-galactosidase was determined with a diverse panel of oligosaccharide structures and a remarkably stringent specificity for α1-3 linked galactose in the branched blood group B structure was found (FIG. 20). The enzyme cleaved neither α4Gal linkages found in P1 and $P^k$ blood group antigens nor the α3Gal linkage in linear B structure without fucose.

Example 8

Bacteroides Fragilis α-Galactosidase Efficiently Cleaves Linear B Oligosaccharides at a Neutral pH Further analysis of the substrate specificity of recombinant purified FragB α-galactosidase surprisingly revealed that this enzyme (in contrast to the earlier purified α-galactosidase from S. griseoplanus) exhibited low activity with the Galα-pNP substrate (~1.6 U/ml using the buffer system 100 mM $NaPO_4$, pH 6.8/50 mM NaCl) (Table IV).

TABLE IV

Comparison of the specific activities (U/mg) of FragB α-Galactosidase and Coffee Bean α-Galactosidase.

| Substrate | Coffee Bean | B. fragilis (FragB)[1] |
|---|---|---|
| Galα-pNP | 32 (pH 6.5)[2] | 1.6 (pH 6.8) |
| Galα1-3(Fucα1-2)Galβ1-4Glc-AMC | 0.017 (pH 5.5)[4] | 9.4 (pH 6.8) |

[1]This work.
[2]Derived from Zhu, A., Monahan, C., Zhang, Z., Hurst, R., Leng, L. & Goldstein, J. (1995) Arch Biochem Biophys 324, 65-70.
[3]not determined.
[4]Derived from U.S. patent application, publication number 20050208655.

Figure 19:
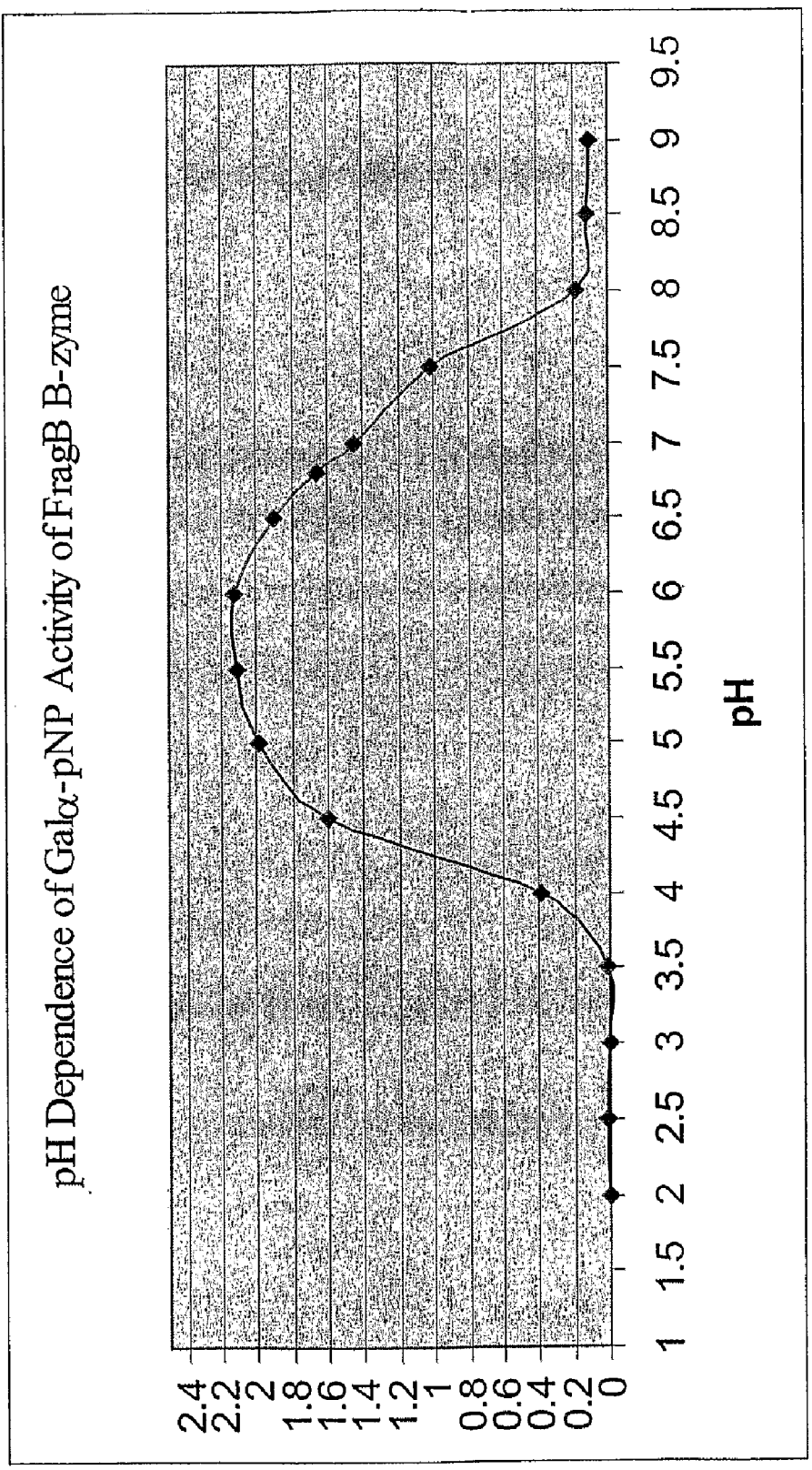
FIG. 19. illustrates the analysis of the enzyme activity under different pH using chromogenic para-nitrophenyl derivative, Galα-pNP. Assays were carried out by using 2.5 mM substrate, 8.5 μg enzyme in 400 μl of buffers between pH 2.0-9.0 as described in the legend of FIG. 17, at 26° C. for 5 min, terminated with 600 μL of 1.0 M $Na_2CO_3$ and, read at 405 nm. A molar extinction coefficient of 18,300 was used to calculate the amount of released nitrophenol. One unit was defined as the amount of enzyme required to cleave 1 μmole of substrate per minute under the experimental condition. The specific activity at each pH was then calculated and plotted versus pH.

This prompted us to test the substrate specificity with substrates having different α1-3Gal and α1-4Gal linkages. As shown in FIG. 19, FragB showed high activity with linear α1-3Gal linkages (B-di and Linear B) in addition to the blood group B oligosaccharide structures. Interestingly, the activity of FragB with the Galα1-3Gal disaccharide was very high (~12 U/mg at pH 6.8) suggesting that this enzyme is suitable for efficient cleavage of the linear B antigen (Galα1-3Galβ1-4GlcNAcβ1-R, where R is any oligosaccharide structure) also known as the Galili antigen (Galili U (2005) Immunol Cell Biol 83:674-86). The Galili antigen is a major xenotransplantation barrier antigen found on most animal tissues except old world monkeys and man (Galili U (2005) Immunol Cell Biol 83:674-86). Xenotransplantation of e.g. pig tissues and cells into man results in hyperacute rejection mainly due to presence of high titers in man of IgG antibodies to the Galili antigen. To date only broadly reactive α-galactosidases such as Coffee bean derived enzymes with acidic pH optimums have been used for cleavage of the Galili antigen from cells and tissues. This may constitute a significant problem since all animal cells express large quantities of e.g. the globoseries $P^k$ glycolipid structure (Galα1-4Galβ1-4Glcβ1-Ceramide). It is more desirable to use α-galactosidase enzymes with higher efficiency, specificity and neutral pH optimum, such as those disclosed herein.

The FragB α-galactosidase was specific for α1-3Gal linkages, and no significant cleavage of several α1-4Gal linkages ($P_1$ and $P^k$) was observed. This is similar to the α-galactosidase obtained from S. griseoplanus, but represents a property that is different from any other known α-galactosidase including the enzyme derived from Coffee bean. The results are summarized in Table V.

TABLE V

Substrate specificity of the α-galactosidases.

| Substrates | Blood Group Specificity | Coffee Bean[1] | S. griseoplanus[1] | B. fragilis[2] (FragB) |
|---|---|---|---|---|
| Galα-pNP | NA[3] | +[4] | −[5] | + |
| Galα1-3Gal | B (B-di) | + | − | + |
| Galα1-3Gaβ1-4GlcNAc | Linear B | + | − | + |
| Galα1-3(Fucα1-2)Gal | B-tri | + | + | + |
| Galα1-4Gal | P₁ | + | − | − |
| Galα1-4Galβ1-4Glc | P^k | + | − | − |
| GalNAcα1-3(Fucα1-2)Gal | A-tri | − | − | − |
| Galα1-3(Fucα1-2)Galβ1-4Glc-AMC | B-tetra | + | + | + |
| GalNAcα1-3(Fucα1-2)Galβ1-4Glc-AMC | A-tetra | − | − | − |

[1]Derived from U.S. patent 20050208655 (Ref.) and Zhu, A., Monahan, C., Zhang, Z., Hurst, R., Leng, L. & Goldstein, J. (1995) Arch Biochem Biophys 324, 65-70.
[2]This work.
[3]Not applicable.
[4]Activity readily detectable under assay conditions.
[5]Activity not readily detectable under assay conditions.

The surprising finding that the FragB α-galactosidase may represent a novel highly efficient enzyme for cleavage of linear B (Galili epitopes) prompted us to test the suitability and efficiency of this enzyme in removing such epitopes from cell surfaces. Rabbit red blood cells contain glycolipids and glycoproteins oligosaccharide chains similar to human red cells, but while oligosaccharide chains in human red cells terminate in ABH structures depending on blood group status, oligosaccharides of rabbit red cells terminate with linear B (Galili epitopes) structures (Galβ1-3Galβ1-4GlcNAc). The lectin Bandeeira (Griffonia) simplicifolia IB4 is generally used to detect linear B (Galili epitopes) structures (Galili U (2005) Immunol Cell Biol 83:674-86), and as shown in Table VI this lectin strongly agglutinates rabbit (but not human) red cells.

TABLE VI

Agglutination of human and rabbit red cells with IB4 lectin and Routine Monoclonal Anti-B Typing Reagents.

| RBC Type | Immucor/Gamma Anti-B | | Diagast Anti-B | | B4 Lectin |
|---|---|---|---|---|---|
| | IS | 4° C. | IS | 4° C. | 10 ug/ml |
| Native Rabbit Cells | 2+ | 4+ | 4+ | 4+ | 4+ |
| Native Human B Cells | 4+ | 4+ | 4+ | 4+ | 4+ |
| Native Human A Cells | 0 | 0 | 0 | 0 | 0 |
| Native Human O Cells | 0 | 0 | 0 | 0 | 0 |

Rabbit red cells therefore serve as an excellent model for analysis of the efficiency of α-galactosidases in the removal of the immunodominant α1-3Gal residue from linear B (Galili epitopes) structures from cell surfaces. Since we have previously developed an efficient conversion process for removal of immunodominant A-type antigens from blood cells using a purified C. meningosepticum α-N-acetylgalactosaminidase enzyme, operative using a Glycine pH 6.8 buffer system, we tested the same conditions for FragB cleavage of rabbit red cells in comparison with human blood group B red cells. As shown in Table VII, FragB efficiently removed IB4 lectin agglutination of rabbit red cells at very low doses, almost comparable to what was required for FragB cleavage of blood group B from human red cells. The agglutination of rabbit red cells by the IB4 lectin was almost completely abolished by the enzyme treatment with 10 g/ml enzyme dose giving only a microscopic reading (M+). Higher concentrations of enzyme or longer incubation complete abolish reactivity. The homologous gene FragA, however, only cleaved blood group B from human red cells.

TABLE VII

Agglutination Results of human and rabbit red cells digested with FragA or FragB glycan modifying enzymes.

| Routine Conversion | | Immucor Anti-B | | Diagast Anti-B | | B4 Lectin |
|---|---|---|---|---|---|---|
| | Dose ug/ml | IS | 4° C. | IS | 4° C. | 10 ug/ml |
| Frag B enzyme | | | | | | |
| Human B Cells | 10 | 0 | 0 | 0 | 0 | 0 |
| | 5 | 0 | 0 | 0 | 0 | 0 |
| | 2.5 | 0 | 0 | 0 | 0 | 0 |
| | 1.25 | 0 | 0 | 0 | 0 | 0 |
| | 0.625 | 0 | W+ | W+ | 1+ | 0 |
| | 0.3125 | 0 | 1+ | 1+ | 1+ | 0 |
| Rabbit Cells | 10 | 0 | 0 | 0 | W+ | M+ |
| | 5 | 0 | 0 | 0 | W+ | Vw+ |
| | 2.5 | 0 | 0 | 0 | W+ | W+ |
| | 1.25 | 0 | 0 | 0 | 1+ | 1+ |
| | 0.625 | 0 | W+ | W+ | 3+ | 1+ |
| | 0.3125 | 0 | 2+ | 4+ | 4+ | 2+ |
| Frag A enzyme | | | | | | |
| Human B Cells | 10 | 0 | 0 | 0 | 0 | 0 |
| | 5 | 0 | 0 | 0 | 0 | 0 |
| | 2.5 | 0 | 0 | 0 | 0 | 0 |
| | 1.25 | 0 | 0 | 0 | 0 | 0 |
| | 0.625 | 0 | W+ | W+ | 1+ | 0 |
| | 0.3125 | 1+ | 1+ | 1+ | 2+ | 0 |
| Rabbit Cells | 10 | 4+ | 4+ | 4+ | 4+ | 3+ |
| | 5 | 4+ | 4+ | 4+ | 4+ | 3+ |
| | 2.5 | 4+ | 4+ | 4+ | 4+ | 3+ |
| | 1.25 | 4+ | 4+ | 4+ | 4+ | 3+ |
| | 0.625 | 4+ | 4+ | 4+ | 4+ | 3+ |
| | 0.3125 | 4+ | 4+ | 4+ | 4+ | 3+ |

This demonstrates that the purified FragB polypeptide isoform described as part of the novel α-galactosidase gene family reported herein, has unique substrate specificities that are different from several other members within this family, including the related genes observed in Streptomyces. Furthermore, that the FragB polypeptide described is suitable for enzymatic removal of immunodominant blood group B antigens from red cells, as well as for removal of the xenotransplantation Galili antigen from blood cells. The purified FragB polypeptide is thus superior to other currently known enzymes, with respect to its pH optimum (most preferably pH 6.5 to pH 7.5), its restricted substrate specificity to Galα1-3 linkages and its observed high specific activity.

Enzymatic removal of the immunodominant α1-3 linked terminal Galactose of the GaIiIi antigens has important applications in the xenotransplantation field. The GaIiIi antigen constitutes the most important barrier for xenotransplantation of organs, tissues, tendons, ligaments and cells from animals to man, and is the primary cause of the hyper-acute rejection phenomenon (Galili U (2005) Immunol Cell Biol 83:674-86). Approximately 10% of normal healthy individuals serum IgG is directed to the GaIiIi antigen. Enzymatic removal of the terminal galactose residue will expose common structures found in man, which may abrogate hyperacute rejection (Galili U (2005) Immunol Cell Biol 83:674-86).

The process described for enzymatic removal of the GaIiIi antigen on rabbit cells in which cells are washed and incubated with the FragB α-galactosidase in a suitable buffer at neutral pH for a period of time results in efficient removal of the GaIiIi epitope (Table VII). A similar process applied to animal organs, tissue, tendons, ligaments and cells, results in efficient removal of exposed GaIiIi antigens.

The preferred process involves contacting the animal tissues or cells with the FragB α-galactosidase (or homologous members of the gene family with similar enzymatic activities) in a suitable buffer such as physiological saline, Glycine or other similar buffer systems described herein, at neutral pH of 5.5 to 8.0 and more preferably 6.5 to 7.5. The enzyme dose and time required for enzymatic removal of the immunodominant α1-3 linked terminal Galactose generally follows the digestion parameters described above for blood cells, but is evaluated empirically, as is determined by lectin and antibody based immunoassays such as immunocytology, immunohistology and ELISA using such suitable lectins such as the IB4 lectin or suitable monoclonal antibodies reactive with the GaIiIi epitope (Galili U (2005) Immunol Cell Biol 83:674-86). When the reaction is complete, the enzyme modified animal organ, tissue, tendon, ligament or cells are washed with an appropriate buffer solution (such as physiological saline) to remove the enzyme solution. The animal tissues or cells lack immunodominant GaIiIi antigens, and can now be used as an appropriate xenotransplant into a human subject in need of such a transplant. An example of this is an antigenically modified porcine ligament, which is used for the reconstruction of ruptured anterior cruciate ligament in a human patient. See for example, U.S. Pat. No. 6,402,783.

Prior to treatment, the outer surface of the xenograft may optionally be pierced to increase permeability to agents used to render the xenograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the xenograft. Piercing may also be performed with a laser. In one embodiment of the invention, one or more straight lines of punctures about three millimeters apart are established circumferentially in the outer surface of the xenograft.

Prior to implantation, the ligament xenograft of the invention may be treated with limited digestion by proteolytic enzymes such as ficin or trypsin to increase tissue flexibility or coated with anticalcification agents, antithrombotic coatings, antibiotics, growth factors, or other drugs which may enhance the incorporation of the xenograft into the recipient knee joint. The ligament xenograft of the invention may be further sterilized using known methods, for example, with additional glutaraldehyde or formaldehyde treatment, ethylene oxide sterilization, propylene oxide sterilization, or the like. The xenograft may be stored frozen until required for use.

The ligament xenograft of the invention, or a segment thereof, may be implanted into a damaged human knee joint by those of skill in the art using known arthroscopic surgical techniques. Specific instruments for performing arthroscopic techniques are known to those of skill in the art, which ensure accurate and reproducible placement of ligament implants. Initially, complete diagnostic arthroscopy of the knee joint is accomplished using known methods. The irreparably damaged ligament is removed with a surgical shaver. The anatomic insertion sites for the ligament are identified and drilled to accommodate a bone plug. The size of the bone plug can be about 9-10 mm in width by about 9-10 mm in depth by about 20-40 mm in length. The xenogeneic ligament is brought through the drill holes and affixed with interference screws. Routine closure is performed.

Using the polypeptides of the present invention thus permits removal of the GaIiIi antigen from many different tissues types, using the modification procedures described herein and as may be further adapted to the particular tissues in view of the teachings provided, by a skilled artisan. These modified tissues are used for a variety of transplant procedures where non-immunogenic xenotransplants are required, as is described in the following: to create e.g. substantially non-immunogenic injectable collagen (see, U.S. Pat. No. 7,064, 187); for bone xenografts (see, U.S. Pat. No. 6,972,041); for soft tissue and proteoglycan-reduced soft tissue xenografts (see, U.S. Pat. Nos. 6,758,865 and 6,455,309); xenograft heart valves (see, U.S. Pat. No. 6,383,732); and meniscal xenografts (see, U.S. Pat. Nos. 6,093,204 and 5,984,858).

In another particularly preferred embodiment, the invention provides for tissue matrices preferably those made from α1,3-galactose-deficient tissues (see, U.S. Pat. No. 6,933,326 and U.S. Patent Application 20050159822 and 20050028228). Methods of making and using these tissue matricies are described in the above patent and applications, and the degalacosylation of the tissues is accomplished using the novel α3 galatosidases as described herein (SEQ ID NO: 2-9, or active fragments or functional equivalents thereof.

We claim:

1. A method of preparing a non-human tissue for xenotransplantation, comprising the steps of:
   (i) incubating the non-human tissue with an enzyme comprising the amino acid sequence of SEQ ID NO:6 and having α-galactosidase activity, thereby cleaving immunodominant α1,3 linked terminal galactose residues from the tissue, and
   (ii) isolating the non-human tissue from the enzyme and the enzymatically-cleaved immunodominant galactose residues,
   thereby rendering the non-human tissue suitable for xenotransplantation into humans.

2. The method of claim 1, wherein the non-human tissue is dermal tissue.

* * * * *